(12) United States Patent
Hamilton

(10) Patent No.: US 8,986,949 B2
(45) Date of Patent: Mar. 24, 2015

(54) ENDOMANNOSIDASES IN THE MODIFICATION OF GLYCOPROTEINS IN EUKARYOTES

(75) Inventor: Stephen Hamilton, Enfield, NH (US)

(73) Assignee: Glycofi, Inc., Lebanon, NH (US)

( * ) Notice: Subject to any disclaimer, the term of this patent is extended or adjusted under 35 U.S.C. 154(b) by 0 days.

(21) Appl. No.: 13/070,946

(22) Filed: Mar. 24, 2011

(65) Prior Publication Data

US 2012/0064568 A1    Mar. 15, 2012

Related U.S. Application Data

(63) Continuation of application No. 12/009,105, filed on Jan. 16, 2008, now abandoned, which is a continuation of application No. 10/695,243, filed on Oct. 27, 2003, now Pat. No. 7,332,299, which is a continuation-in-part of application No. 10/371,877, filed on Feb. 20, 2003, now Pat. No. 7,449,308.

(51) Int. Cl.
| | |
|---|---|
| C12P 21/06 | (2006.01) |
| C07H 21/02 | (2006.01) |
| C07H 21/04 | (2006.01) |
| C12P 21/00 | (2006.01) |
| C12N 9/10 | (2006.01) |
| C12N 9/24 | (2006.01) |

(52) U.S. Cl.
CPC ............. *C12P 21/005* (2013.01); *C12N 9/1051* (2013.01); *C12Y 302/0113* (2013.01); *C12N 9/2488* (2013.01)
USPC .......................... 435/68.1; 435/69.1; 536/23.1

(58) Field of Classification Search
None
See application file for complete search history.

(56) References Cited

U.S. PATENT DOCUMENTS

| | | | |
|---|---|---|---|
| 4,414,329 A | 11/1983 | Wegner | |
| 4,617,274 A | 10/1986 | Wegner | |
| 4,683,293 A | 7/1987 | Craig | |
| 4,775,622 A | 10/1988 | Hitzeman et al. | |
| 4,808,537 A | 2/1989 | Stroman et al. | |
| 4,812,405 A | 3/1989 | Lair et al. | |
| 4,818,700 A | 4/1989 | Cregg et al. | |
| 4,837,148 A | 6/1989 | Cregg | |
| 4,855,231 A | 8/1989 | Stroman et al. | |
| 4,857,467 A | 8/1989 | Sreekrishna et al. | |
| 4,879,231 A | 11/1989 | Stroman et al. | |
| 4,882,279 A | 11/1989 | Cregg | |
| 4,885,242 A | 12/1989 | Cregg | |
| 4,925,796 A | 5/1990 | Bergh et al. | |
| 4,929,555 A | 5/1990 | Cregg et al. | |
| 4,935,349 A | 6/1990 | McKnight et al. | |
| 5,002,876 A | 3/1991 | Sreekrishna et al. | |
| 5,004,688 A | 4/1991 | Craig et al. | |
| 5,032,516 A | 7/1991 | Cregg | |
| 5,032,519 A | 7/1991 | Paulson et al. | |
| 5,047,335 A | 9/1991 | Paulson et al. | |
| 5,122,465 A | 6/1992 | Cregg et al. | |
| 5,135,854 A | 8/1992 | MacKay et al. | |
| 5,166,329 A | 11/1992 | Cregg | |
| 5,272,066 A | 12/1993 | Bergh et al. | |
| 5,324,663 A | 6/1994 | Lowe | |
| 5,595,900 A | 1/1997 | Lowe | |
| 5,602,003 A | 2/1997 | Pierse et al. | |
| 5,683,899 A | 11/1997 | Stuart | |
| 5,707,828 A | 1/1998 | Sreekrishna et al. | |
| 5,766,910 A | 6/1998 | Fukuda et al. | |
| 5,834,251 A | 11/1998 | Maras et al. | |
| 5,844,093 A | 12/1998 | Kettleborough et al. | |
| 5,849,904 A | 12/1998 | Gerardy-Schahn et al. | |
| 5,854,018 A | 12/1998 | Hitzemane et al. | |
| 5,861,293 A | 1/1999 | Kojiri et al. | |
| 5,910,570 A | 6/1999 | Elhammer et al. | |
| 5,945,314 A | 8/1999 | Prieto et al. | |
| 5,945,322 A | 8/1999 | Gotschlich | |
| 5,955,347 A | 9/1999 | Lowe | |
| 5,955,422 A | 9/1999 | Lin | |
| 5,962,294 A | 10/1999 | Paulson et al. | |
| 6,017,743 A | 1/2000 | Tsuji et al. | |
| 6,069,235 A | 5/2000 | Davis et al. | |
| 6,096,512 A | 8/2000 | Elhammer et al. | |
| 6,204,431 B1 | 3/2001 | Prieto et al. | |
| 6,300,113 B1 | 10/2001 | Landry | |
| 6,410,246 B1 | 6/2002 | Zhu et al. | |
| 6,602,684 B1 | 8/2003 | Umana et al. | |

(Continued)

FOREIGN PATENT DOCUMENTS

| | | |
|---|---|---|
| EP | 0 905 232 | 3/1999 |
| EP | 1 054 062 | 11/2000 |

(Continued)

OTHER PUBLICATIONS

Hamilton et al. (Glycobiology, vol. 15. No. 6, pp. 615-624, 2005.*

(Continued)

*Primary Examiner* — Gary Nickol
*Assistant Examiner* — Khatol Shahnan Shah
(74) *Attorney, Agent, or Firm* — Gloria Fuentes; Immac Thampoe

(57) ABSTRACT

The present invention generally relates to methods of modifying the glycosylation structures of recombinant proteins expressed in fungi or other lower eukaryotes, to more closely resemble the glycosylation of proteins from higher mammals, in particular humans. The present invention also relates to novel enzymes and, nucleic acids encoding them and, hosts engineered to express the enzymes, methods for producing modified glycoproteins in hosts and modified glycoproteins so produced.

5 Claims, 19 Drawing Sheets

(56) References Cited

U.S. PATENT DOCUMENTS

| | | | |
|---|---|---|---|
| 6,946,292 | B2 | 9/2005 | Kanda et al. |
| 7,029,872 | B2 * | 4/2006 | Gerngross ............... 435/69.1 |
| 7,064,191 | B2 | 6/2006 | Shinkawa et al. |
| 7,214,775 | B2 | 5/2007 | Hanai et al. |
| 7,259,007 | B2 | 8/2007 | Bobrowicz |
| 7,326,681 | B2 | 2/2008 | Gerngross |
| 7,332,299 | B2 | 2/2008 | Hamilton |
| 7,365,163 | B2 | 4/2008 | Hanna |
| 7,368,531 | B2 * | 5/2008 | Rosen et al. ............... 530/350 |
| 7,449,308 | B2 | 11/2008 | Gerngross |
| 7,465,577 | B2 | 12/2008 | Bobrowicz |
| 7,514,253 | B2 | 4/2009 | Nett |
| 7,517,670 | B2 | 4/2009 | Umana |
| 7,598,055 | B2 | 10/2009 | Bobrowicz |
| 7,625,756 | B2 | 12/2009 | Hamilton |
| 7,629,163 | B2 | 12/2009 | Gerngross |
| 2003/0157108 | A1 | 8/2003 | Presta |
| 2003/0175884 | A1 | 9/2003 | Umana et al. |
| 2004/0191256 | A1 | 9/2004 | Raju |
| 2005/0170452 | A1 | 8/2005 | Wildt et al. |
| 2005/0260729 | A1 | 11/2005 | Hamilton |
| 2005/0265988 | A1 | 12/2005 | Choi et al. |
| 2006/0024292 | A1 | 2/2006 | Gerngross et al. |
| 2006/0024304 | A1 | 2/2006 | Gerngross et al. |
| 2006/0029604 | A1 | 2/2006 | Gerngross et al. |
| 2006/0034828 | A1 | 2/2006 | Gerngross et al. |
| 2006/0034829 | A1 | 2/2006 | Gerngross et al. |
| 2006/0034830 | A1 | 2/2006 | Gerngross et al. |
| 2006/0040353 | A1 | 2/2006 | Davidson et al. |
| 2006/0177898 | A1 | 8/2006 | Gerngross |
| 2006/0257399 | A1 | 11/2006 | Gerngross et al. |
| 2006/0286637 | A1 | 12/2006 | Hamilton |
| 2007/0037248 | A1 | 2/2007 | Bobrowicz et al. |
| 2007/0105127 | A1 | 5/2007 | Gerngross |
| 2007/0154591 | A1 | 7/2007 | Andersen |
| 2008/0274162 | A1 | 11/2008 | Nessa et al. |

FOREIGN PATENT DOCUMENTS

| | | |
|---|---|---|
| EP | 1176195 | 1/2002 |
| EP | 1 211 310 | 6/2002 |
| EP | 1 239 047 | 9/2002 |
| EP | 1297172 | 4/2003 |
| EP | 1522590 | 4/2005 |
| JP | 8-336387 | 12/1996 |
| JP | 11-103158 | 4/1999 |
| WO | WO92/09694 | 6/1992 |
| WO | WO 96/21038 | 7/1996 |
| WO | WO 98/05768 | 2/1998 |
| WO | WO 99/31224 | 6/1999 |
| WO | WO 99/40208 | 8/1999 |
| WO | WO 99/54342 | 10/1999 |
| WO | WO 00/61739 | 10/2000 |
| WO | WO 01/14522 | 3/2001 |
| WO | WO 01/25406 | 4/2001 |
| WO | WO 01/36432 | 5/2001 |
| WO | WO 01/60860 | 8/2001 |
| WO | WO 02/00856 | 1/2002 |
| WO | WO02/00879 | 1/2002 |
| WO | WO 02/00879 | 1/2002 |
| WO | WO 02/097060 | 12/2002 |
| WO | WO 03/011878 | 2/2003 |
| WO | WO 03/025148 | 3/2003 |
| WO | WO 03/031464 | 4/2003 |
| WO | WO 03/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074497 | 9/2004 |
| WO | WO 2004/074498 | 9/2004 |
| WO | WO 2004/074499 | 9/2004 |
| WO | WO 2004/104165 | 12/2004 |
| WO | WO 2005/065019 | 7/2005 |
| WO | WO 2005/090552 | 9/2005 |
| WO | WO 2005/100584 | 10/2005 |
| WO | WO 2005/106010 | 11/2005 |
| WO | WO 2006/014679 | 2/2006 |
| WO | WO 2006/014683 | 2/2006 |
| WO | WO 2006/014685 | 2/2006 |
| WO | WO 2006/014725 | 2/2006 |
| WO | WO 2006/071280 | 7/2006 |
| WO | WO 2006/071856 | 7/2006 |
| WO | WO 2006/014726 | 9/2006 |
| WO | WO 2007/028144 | 3/2007 |
| WO | WO 2007/029054 | 3/2007 |

OTHER PUBLICATIONS

Spiro et al. (The Journal of Biological Chemistry, vol. 272, No. 46, pp. 29356-29363, 1997).*

Herscovics et al. The Journal of Biological Chemistry, vol. 269, No. 13, pp. 9864-9871 Apr. 1994.*

Tefsen, Boris et al., "Galactofuranose in eukaryotes: aspects of biosynthesis and functional impact" Glycobiology 22:456-469 (2012).

Gemmill, Trent R. et al., "Overview of N- and O-linked oligosaccharide structures found in various yeast species" Biochimica et Biophysics Acta 1426:227-237 (1999).

Shibuya Naoto et al., "Binding Properties of a Mannose-specific Lectin from the Snowdrop (Galanthus nivalis) bulb," J. Biol. Chem. 263, 728-734 (1988).

Fouquaert, Elke et al., "Related lectins from snowdrop and maize differ in their carbohydrate-binding specificity" Biochem Biophys Res. Commun. 380:260-265 (2009).

Davidson, Robert C. et al., "Functional analysis of the ALG3 gene encoding the Dol-P-Man: Man5GlcNAc2-PP-Dol mannosyltransferase enzyme of P. pastoris" Glycobiology 14:399-407 (2004).

Ichishima Eliji et al., "Molecular and enzymic properties of recombinant 1,2-α-mannosidase from Aspergillus saitoi overexpressed in Aspergillus oryzae cells" Biochem J. 339:589-597 (1999).

Verostek, Mary Fran et al., "glycoprotein Biosynthesis in the alg3 Saccharomyces cerevisiae Mutant" J. Biol. Chem. 266:12104-12115 (1993).

Lubas, William A. et al., "Golgi Endo-α-D-mannosidase from Rat Liver, a novel N-linked carbohydrate unit processing enzyme" J boil. Chem. 262:3775-3781 (1987).

Dong, Zhizhong et al., "Immunohistochemical evaluation of endomannosidase distribution in rate tissues: evidence for cell type-specific expression" Histochem. Cell. Biol. 114:461-467 (2000).

Dairaku, Katsuryo et al., "Phylogenetic survey of endomannosidase indicates late evolutionary appearance of this N-linked oligosaccharide processing enzyme" Glycobiology 7(4):579-586 (1997).

Hamilton, Stephen R. et al., "Intact α-1,2-endomannosidase is a typical type II membrance protein" Glycobiology 15(6):615-624 (2005).

Stehli, J. et al., "Triple arginines in the cytoplasmic tail of endomannosidase are not essential for type II membrane topology and Golgi localizaiton" Cell. Mol. Life Sci. 65:1609-1619 (2008).

Declaration of Dr. Jari Natunen (BM41), submitted in opposition to EP1597379 (May 2, 2011).

Thesis of Master Science of Mr. Benton James Miller, entitled Cloning and Characterization of the ALG3 homologue in Pichia pastoris: the role of ALG3 mutants in humanizing glycosylation of therapeutic glycoproteins; (May 2003).

Interlocutory decision of Opposition Division in EP 159379 (Dec. 23, 2011).

Written Statement Setting Out the Grounds of Appeal filed by Novartis in Opposition to EP 1597379 (May 2, 2012).

Patentee's Submissions in Opposition to EP 1597379 (Sep. 13, 2011).

Written Submissions by Novartis in Opposition to EP 1597379 (Jul. 20, 2011).

Patentee's Submissions in Opposition to EP 1597379 (Jul. 20, 2011).

Reply of Patentee's to Notice of Opposition to EP 1597379 (Jul. 20, 2010).

(56) References Cited

OTHER PUBLICATIONS

Abeijon et al., "Molecular Cloning of the Golgi apparatus uridine diphosphate-N-acetylglucosamine transporter from *Kluyveromyces lactis*," Proc. Natl. Acad. Sci. USA 93:5963-5968 (1996).

Carninci et al., "Mus Musculus Adult Male Testis cDNA, Riken full length enriched library, clone: 4931438M07 product: mannosidase 2, alpha 2, full insert sequence" GenBank Accession No. AK029913. Electronic record printed on Aug. 9, 2013.

Alani et al., "A Method for Gene Disruption that Allows Repeated Use of URA3 Selection in the Construction of Multiply Disrupted Yeast Strains," Genetics 116, 541-545, Aug. 1987.

Abdel-Salam et al., "Expression of mouse anticreatine kinase (MAK33) monoclonal antibody in the yeast Hansenula Polymorpha", App. Microbiol. Biotechnol. 56:157-164 (2001).

Allison, Daniel S., et al., "Mutations in the Signal Sequence of Prepro-α-Factor Inhibit Both Translocation into the Endoplasmic Reticulum and Processing by Signal Peptide in Yeast Cells," Molecular and Cellular Biology, vol. 9(11):4977-4985 (1989).

Altman et al., "Processing of Asparagine-linked Oligosaccharides in Insect Cells: Evidence for Alpha-Mannosidase II," *Glycoconj. J* 12(2):150-155 (1995).

Altman et al., "Insect cells as hosts for the expression of recombinant glycoproteins," *Glycoconj. J.* 16(2):109-123 (1999).

Al-Rawi et al., (2004) Synthesis and biochemical properties of reversible inhibitors of UDP-N-acetylglucosamine 2-epimerase. Angew. Chem. Int. Ed. Engl. vol. 43, No. 33, pp. 4366-4370.

Altschul et al., "Basic Local Alignment Search Tool", J. Mol. Biol. 215:403-410 (1990).

Altschul et al., "Gapped BLAST and PSI-BLAST: a new generation of protein database search program", Nucleic Acids Res. 25:3389-3402 (1997).

Andersen et al., "The Effect of Cell-Culture Conditions on the Oligosaccharide Structures of Secreted Glycoproteins," *Curr Opin Biotechnol*, 5(5):546-549, Oct. 1994.

Aoki et al., "Expression and activity of chimeric molecules between human UDP-galactose transporter transporter and CMP-sialic acid transporter," *J. Biochem.* (Tokyo), 126(5):940-50, Nov. 1999.

Bardor et al., "Analysis of the N-glycosylation of recombinant glycoproteins produced in transgenic plants," *Trends in Plant Science* 4(9): 376-380 (1999).

Bause and Burbach, "Purification and Enzymatic Properties of Endo-α1,2-Mannosidase from Pig Liver Involved in Oligosaccharide Processing," *Biol. Chem*. 377:639-646 (1996).

Beaudet et al., "High-level expression of mouse Mdr3 P-glycoprotein in yeast Pichia pastoris and characterization of ATPase activity," *Methods Enzymol* 292: 397-413 (1998).

Berka et al., "The development of Aspergillus niger var. awamori as a host for the expression and secretion of heterologous gene products" vol. 19, pp. 681-685 (1991).

Berninsone et al., "The Golgi Guanosine Diphophatase is Required for Transport of GDP-Mannose Into the Lumen of *Saccharomyces cerevisiae* Golgi Vesicles," *J. Biol. Chem*., 269(1):207-211, Jan. 1994.

Berninsone et al., "Regulation of yeast Golgi glycosylation. Guanosine diphosphatase functions as a homodimer in the membrane," *J. Biol. Chem* 270(24): 14564-14567 (1995).

Berninsone et al., "Functional Expression of the Murine Golgi CMP-Sialic Acid Transporter in *Saccharomyces cerevisiae*," *J. Biol. Chem*. 272(19):12616-12619, May 1997.

Bianchi et al., "Transformation of the yeast *Kluyweromyces lactis* by new vectors derived from the 1.6 μm circular plasmid pKD1," *Current Genetics*, 12:185-192, 1987.

Bobrowicz, Piotr et al., Engineering of an artificial glycosylation pathway blocked in core oligosaccharide assembly in the yeast Pichia pastoris: production of complex humanized glycoproteins with terminal galactose,: Glycobiology, vol. 14(9): 757-766 (2004).

Boehm et al., "Disruption of the KEX1 Gene in *Pichia Pastoris* Allows Expression of Full Length Murine and Human Endostatin," *Yeast*, 15:563-572 (1999).

Boeke et al., "A positive selection for mutants lacking orotidine-5'-phosphate decarboxylase activity in yeast: 5-fluoro-orotic acid resistance", Mol. Gen. Genet. 197:345-346 (1984).

Bonneaud et al., "A family of low and high copy replicative, integrative and single-stranded *S. cerevisiae/E. coli* shuttle vectors," *Yeast* 7(6): 609-615 (1991).

Borreback et al., "Human Momoclonal antibodies produced by primary in vitro immunization of peripheral blood lymphocytes", Proc. Natl. Acad. Sci. USa, 85:3995-3999 (1988).

Boutin, "Myristoylation," Cell. Signal. 9(1):15-35 (1997).

Bretthauer et al., "Glycosylation of Pichia pastoris-derived proteins," *Biotechnol Appl Biochem* 30(Pt 3): 193-200 (1999).

Bretthauer et al., "Genetic engineering of Pichia pastoris to humanize N-glycosylation of proteins," *TRENDS in Biochem*, 21(11): 459-462 (2003).

Brockhausen et al., "Control of glycoprotein synthesis. The use of oligosaccharide substrates and HPLC to study the sequential pathway for N-acetylglucosaminyltransferases I, II, III, IV, V and VI in the biosynthesis of highly branched N-glycans by hen oviduct membranes," Biochem. Cell Biol. 66:1134-1151 (1988).

Bucket et al., "Cloning and nucleotide sequence of heavy and light chain cDNAs from a creatine-kinase-specific monoclonal antibody", Gene, 51:13-19 (1987).

Cadwell and Joyce, Randomization of Genes by PCR Mutagenesis:, PCR Methods Applic. 2:28-33 (1992).

Callewaert et al., "Use of HDEL-tagged Trichoderma reesei mannosyl oligosaccharide 1,2-α-D-mannosidase for N-glycan engineering in Pichia pastoris", FEBS Lett. 503(2-3):173-178 (2001).

Cabanes-Macheteau et al., "N-Glycosylation of a mouse IgG expressed in transgenic tobacco plants," Glycobiology, vol. 9, No. 4., pp. 365-372 (1999).

Carninci et al., XP-002293371, AK030141, dated Dec. 5, 2002, Mus musculus adult male testis cDNA . . . : RIKEN full-length library. clone 4932703L02.

Cereghino et al., "Heterologous protein expression in the methylotrophic yeast *Pichia pastoris,*" *FEMS Microbiology Reviews*, 24(1): 45-66 (2000).

Cereghino et al., "New selectable marker/auxotrophic host strain combinations for molecular genetic manipulation of *Pichia pastoris,*" Gene, 263:159-169 (2001).

Chandrasekaran et al., "Purification and Properties of Alpha-D-Mannose:beta-1,2-N-acetylglucosaminyl-transferases and alpha-D-Mannosidases from Human Adenocarcinoma," *Cancer Res*., 44(9):4059-68, Sep. 1984.

Chapman et al., „Effects of glucose starvation and puromycin treatment on lipid-linked oligosaccharide precursors.., Arch. Biochem. Biophys. 260(1):320-333 (1988).

Chen et al., (1995) Effect of retinoic acid on the structure of N-glycans on the surface of human hepatocarcinoma cells and its enzymatic mechanism, J. Cancer Res. Clin. Oncol. vol. 121, No. 7, pp. 397-401.

Chiba et al., "Production of Human Compatible High Mannose-type ($Man_5GlcNAc_2$) Sugar Chains in *Saccharomyces cerevisiae,*" *J. Biol. Chem*., 273(41):26298-26304, Oct. 1998.

Choi et al., "Use of combinatroial genetic libraries to humanize N-linked glycosylation in the yeast *Pichia pastoris,*" Proc. Natl. Acad. Sci. USA 100(9):5022-5027 (2003).

Chui et al., "Genetic Remodeling of Protein Glycosylation in vivo Induces Autoimmune Disease," Proc. Natl. Acad. Sci., USA 98:1142-1147 (2001).

Chui et al., "Alpha-mannosidase-II Deficiency Results in Dyserythropoiesis and Unveils and Alternate Pathway in Oligosaccharide Biosynthesis," *Cell*, Jul. 11, 1997; 90(1):157-67.

Cole, et al., "Modelling the growth, survival and death of microorganisms in foods: the UK food micromodel approach," International Journal of Food Microbiology 23(3-4) 265-275 (1994).

D'Agostaro et al., "Molecular cloning and expression of cDNA encoding the rate UDP-N-acetylglucosamine:alpha-6-D-mannoside beta-1,2-N-acetylglucosaminyltransferase II", J. Biol. Chem, vol. 270, No. 25, pp. 15211-15221 (1995).

Daniel et al, "Mammalian Alpha-Mannosidases—Multiple Forms but a Common Purpose?", *Glycobiology*, 4, 551-566, Oct. 1994.

(56) References Cited

OTHER PUBLICATIONS

Davidson et al., "A PCR-Based Strategy to Generate Integrative Targeting Alleles With Large Regions of Homology," *Microbiology*, 148 (Pt 8):2607-15). (2002).

Davies et al., "Expression of GnTIII in a Recombinant Anti-CD20 CHO Production Cell Line:; Expression of Antibodies with Altered Glycoforms Leads to an Increase in ADCC Through Higher Affinity for FcγRIII", Biotechnol. Bioeng., 74(4):288-294 (2001).

Dempski and Imperiali, "Oligosaccharyl transferase: gatekeeper to the secretory pathway," *Curr. Opin. in Chem. Biol.* 6:844-850 (2002).

Dennis et al., "Protein glycosylation in development and disease", Bioessays, 21(5):412-21 (1999).

Dente, "Human alpha-1-acid glycoprotein genes," Prog. Clin. Biol. Res 300:85-98 (1989).

Duman et al., "O-mannosylation of Pichia pastoris cellular and recombinant proteins", Biotechnology Appl. Biochem., vol. 28, pp. 39-45 (1998).

Duvet et al., "Cytosolic Deglycosylation Process of Newly Synthesized Glycoproteins Generates Oligomannosides Possessing One GlcNAc Residue at the Reducing End," *Biochem J.*, 335, 1998, 389-396.

Eades et al., "Characterization of the Class I alpha-Mannosidase Gene Family in the Filamentous Fungus Aspergillus Nidulans," *Gene*, Sep. 5, 2000; 255(1):25-34.

Eckhardt et al., "Molecular Cloning of the Hamster CMP-Sialic Acid Transporter," *Eur. J. Biochem.*, 248(1):187-192 (1997).

Foster et al., "Cloning and Sequence Analysis of GmII, a Drosophila Melanogaster Homologue of the cDNA Encoding Murine Golgi alpha-Mannosidase II," *Gene* 154 (1995) 183-186.

Fujita et al., Biochem. & Biophys. Res. Comm., vol. 238 (1997), pp. 779-783, "Five crucial carboxyl residues of 1,2-alpha-mannosidase . . . "

Fukuta et al., "Remodeling of sugar chain structures of human interferon-γ", Glycobiology, vol. 10, pp. 421-430 (2000).

Gavel et al., "Sequence differences between glycosylated and non-glycosylated Asn-X-Thr/Ser acceptor sites: implications for protein engineering", Protein Eng., 3:433-43 (1990).

Gerngross, Tillman U., "Advances in the production of human therapeutic proteins in yeasts and filamentous fungi", Nature biotechnology, vol. 22(11):1409-1414 (2004).

Gleeson, Paul A. "Targeting of Proteins to the Golgi Apparatus," *Histochem. Cell Biol.*, 109:517-532 (1998).

Gleeson et al (1983) Control of glycoprotein synthesis. J. Biol. Chem. vol. 258, No. 10, pp. 6162-6173.

Gonzalez, Daniel S et al: "The Alpha-Mannosidases: Phylogeny and Adaptive Diversification" Molecular Biology and Evolution, vol. 17, No. 2, Feb. 2000, pp. 292-300, XP002293609 ISSN: 0737-4038.

Goochee et al., "The Olgosaccharides of Glycoproteins: Bioprocess Factors Affecting Oligosaccharide Structure and Their Effect on Glycoprotein Properties", Biotechnology, 9(12):1347-1355 (1999).

Graham et al., "Compartmental Organization of Golgi-specific Protein Modification and Vacuolar Protein Sorting Events Defined in Yeast *sec*18 (*NSF*) Mutant," *J. Cell. Biol.*, 114(2): 207-218 (1991).

Grard et al., "Oligomannosides or Oligosaccharide-lipids as Potential Substrates for Rat Liver Cytosolic α-D-Mannosidase," *Biochem. J.*, 316: 787-792 (1996).

Grasziano et al., "Construction and Characterization of a Humanized Anti-γ-Ig Receptor Type I (FcγRI) Monoclonal Antibody", J. Immunol., 155(10):4996-5002 (1995).

Guillen et al., "Mammalian Golgi apparatus UDP-*N*-acetylglucosamine transporter: Molecular Cloning by Phenotypic Correction of a Yeast Mutant," *Proc. Natl. Acad. Sci. USA*, 95(14):7888-7892 (1998).

Hamilton et al., "Production of Complex Human Glycoproteins in Yeast," *Science* 301:1244-1246 (2003).

Hamilton, Stephen R. et al., "Humanization of Yeast to Produce Complex Terminally Sialylated Glycoproteins", Science, vol. 313:1441-1443 (2006).

Hard, et al, "Isolation and structure determination of the intact sialylated N-linked carbohydrate chains of recombinant human follitropin expressed in Chinese hamster ovary cells," Eur. J. biochem., vol. 193, No. 1, pp. 263-271 (1990).

Harkki et al., "A Novel Fungal Express System—Secretion of Active Calf Chymosin from the Filamentous Fungus Trichoderma-Reesei," *Bio-Tech* 7:596-603 (1989).

Harris B.R..: "Caenorhabditis Elegans Cosmid F58H1" XP002293610, Protein F58H1.1, Abstract, Databaase EMBL Jul. 13, 1996.

Haworth, Robert S., et al., "Intracellular pH in Schizosaccharomyces pombe—Comparison with *Saccharomyces cerevisiae*", Molecular and Cellular Biochemistry, vol. 124, pp. 131-140 (1993).

Hayes et al., "Carbohydrate Compositions of the Rabbit Plasminogen Isozymes", J. Arch. Biochem. Biophys., 171:651-655 1975).

Hernandez et al., "Structure of the Phosphorylated N-linked Oligosaccharides from the mnn9 and mnn10 Mutants of *Saccharomyces cerevisiae*", The Journal of Biological Chemistry, 264(23):13648-13659 (1989).

Herscovics, Processing glycosidases of *Saccharomyces cerevisiae, Biochim. Biophys. Acta* 1426:275-285 (1999).

Hiraizumi et al., "Characterization of Endomannosidase Inhibitors and Evaluation of Their Effect on *N*-Linked Olligosaccharide Processing during Glycoprotein Biosynthesis," *J. Biol. Chem.* 268(13):9927-9935 (1993).

Hiraizumi et al., "Ligand Affinity Chromatographic Purification of Rat Liver Golgi Endomannosidase," *J. Biol. Chem.* 269(7)4697-4700 (1994).

Huffaker et al., "Yeast mutants deficient in protein glycosylation", Proc. Natl. Acad. Sci. USA, 80(24):7466-70 (1983).

Ichishima et al., "Molecular and Enzymic Properties of Recombinant 1,2-∀-Mannosidase from *Aspergillus saitoi* Overexpressed in *Aspergillus oryzae* Cells," 1999; *Biochem. J.*, 339(Pt 3): 589-597.

Inamori et al., Molecular Cloning and Characterization of Human GnT-IX, a Novel β1,6-N-Acetylglucosaminyltransferase that is specifically expressed in the Brain, J. Biol. Chem., vol. 278, No. 44, pp. 43102-43109 (2003).

Ishida et al., "Molecular Cloning and Characterization of a Novel Isoform of the Human UDP-Galactose Transporter, and of Related Complementary DNAs Belonging to the Nucleotide-Sugar Transporter Gene Family", J. Biochem., (Tokyo) 120(6):1074-1078 (1996).

Ishida et al., "Molecular Cloning and Functional Expression of the Human Golgi UDP-*N*-Acetylglucosamine Transporter," *J. Biochem.*, 126(1):68-77 (1999).

Jarvis et al., "Isolation and Characterization of a Class II alpha-mannosidase cDNA from Lepidopteran Insect Cells," *Glycobiology*, 1997; 7(1):113-127 (1997).

Jarvis et al., "Engineering N-glycosylation pathways in the baculovirus-insect cell system," *Curr Opin Biotechnol* 9(5): 528-33 (1998).

Jungmann et al., Multi-protein complexes in the cis Golgi of *Saccharomyces cerevisiae* with alpha-1,6-mannosyltransferase activity, EMBP J., vol. 17, No. 2, pp. 423-434 (1998).

Juranic et al., Antiproliferative action of water extracts of seeds or pulp of five different raspberry cultivars, Food Chem., vol. 93, pp. 39-45 (2005).

Kainuma et al., "Coexpression of α1,2 galactosyltransferase and UDP-galactose transporter efficiently galatosylates *N*- and *O*-glycan in *Saccharomyces cerevisiae*," Glycobiology, 9(2): 133-141 (1999).

Kaletta et al., "The peptide HDEF as a new retention signal is necessary and sufficient to direct proteins to the endoplasmic reticulum", FEBS Lett., vol. 434, No. 3, pp. 377-381 (1998).

Kalsner et al., "Insertion into *Aspergillus nidulans* of functional UDP-GlcNAc: α3-D-mannoside β-1,2-*N*-acetylglucosaminyl-transferase I, the enzyme catalysing the first committed step from oligomannose to hybrid and complex N-glycans," *Glycoconj. J.*, 12(3):360-370 (1995).

Kawar et al., "Insect Cells Encode a Class II ∀-Mannosidase with Unique Properties," *J. Biol. Chem.*, 276(19):16335-16340 (2001).

Khatra et al., "Some kinetic properties of human milk galactosyltransferase," *Eur. J. Biochem.* 44:537-560 (1974).

Kim, Jae Hong et al., "Nonivasive measurement of the pH of the endoplasmic reticulum at rest and during calcium release", Proc. Natl. Acad. Sci. USA, vol. 95, pp. 2997-3002 (1998).

(56) References Cited

OTHER PUBLICATIONS

Kojima, N. et al., "Characterization of Mouse ST8Sia II (STX) as a neural cell adhesion molecule-specific polysialic acid synthase", The Journal of Biological Chemistry, vol. 271, No. 32, pp. 19457-19463 (1996).

Krezdorn et al., "Human β1,4 galactosyltransferase and α2,6 sialytransferase expressed in *Saccharomyces cerevisiae* are retained as active enzymes in the endoplasmic reticulum," *Eur. J. Biochem.*, 220(3): 809-17 (1994).

Kyte and Doolittle, "A Simple Method for Displaying the Hydropathic Character of a Protein," *J. Mol. Biol.* 157:105-132 (1982).

Lal et al., "Isolation and Expression of Murine and Rabbit cDNAs Encoding an α1,2-Mannosidase Involved in the Processing of Asparagine-Linked Oligosaccharides," *J. Biol. Chem.*, 1994. 269(13): 9872-9881.

Lal et al. "Substrate Specificities of Recombnant Murine Golgi α1,2-Mannosidase IA and IB and Comparison with Endoplasmic Reticulum and Golgi Processing α1,2-Mannosidases," *Glycobiology* 8(10):981-995, 1998.

Lee et al., "Sequential §-integration for the regulated insertion of cloned genes . . . ", Biotechnol. Prog., vol. 13, pp. 368-373 (1997).

Lehle and Tanner, "Membrane-Bound Mannosyl Transferase in Yeast Glycoprotein Biosynthesis," *Biochem. Biophys. Acta*, 350(1): 225-235, 1974.

Leung et al., "A method for random mutagenesis of a defined DNA segment using a modified polymerase chain reacation", Techniqure, 1:11-15 (1989).

Li et al., "Optimization of humanized IgGs in glycoengineered Pichia Pastoris" Nature Biotech., vol. 24, pp. 210-215 (2006).

Liao et al., "Cloning, Expression, Purification, and Characterization of the Human Broad Specificity Lysosomal Acid α-Mannosidase," *J Biol Chem* 271(45): 28348-28358 (1996).

Lifely et al., "Glycosylation and biological activity of CAMPATH-1H expressed in different cell lines . . . ", Glycobiology, vol. 5, pp. 813-822 (1995).

Llopis, J., et al., "Measurement of cytosolic, mitochondrial, and Golgi pH in single living cells with green fluorescent proteins", Proc. Natl. Acad. Sci. USA, vol. 95, pp. 6803-6808 (1998).

Lopez, et al., "Microheterogeneity of the oligosaccharides carried by the recombinant bovine lactoferrin expressed in mamestra brassicae cells," Glycobiology., vol. 7, No. 5, pp. 635-651 (1997).

Lowder et al., "Monoclonal antibodies—therapeutic and diagnostics uses in malignancy", Western J. Med., vol. 143(6), pp. 810-818 (1985).

Lu et al., "Cloning and Disruption of the b-Isopropylmalate Dehydrogenase Gene of *Pichia stipitis* with URA3 and Recovery of the Double Auxotroph," *Appl. Microbiol. Biotechnol.*, 49 (2): 141-146 (1998).

Lubas and Spiro, "Evaluation of the Role of Rat Liver Golgi Endo-α-D-mannosidase in Processing *N*-linked Oligosaccharides," *J. Biol. Chem.* 263(8):3990-3998 (1988).

Lussier et al., "The *KTR* and *MNNI* mannosyltransferase families of *Saccharomyces cerevisiae,*" Biochimica et Biophysica Acta 1426: 323-334 (1999).

Madden et al., "Applications of Network BLAST Server", Meth. Enzymol., 266:131-141 (1996).

Makoto, T., et al., "Trial for Molecular Breeding of Yeast for the production of glycoprotein therapeutics", Trends in Glycoscience and Glycotechnology, vol. 9 (suppl.):S29-S35 (1997).

Malissard et al., "Expression of functional soluble forms of human beta-1, 4-galactosyltransferase I, alpha-2-6-sialyltransferase, and alpha-1, 3-fucosyltransferase VI in the methylotrophic yeast Pichia pastoris," Biochem Biophys Res Commun 267(1): 169-173 (2000).

Maras et al., "In vitro conversion of the carbohydrate moiety of fungal glycoproteins to mammalian-type oligosaccharides," *Eur. J. Biochem.*, 249: 701-707 (1997).

Maras et al., "*Structural characterization of N-linked* oligosaccharides from cellobiohydrolase I . . . ," *Eur. J. Biochem.*, 245: 617-625 (1997).

Maras et al., "Filamentous fungi as production organisms for glycoproteins of bio-medical interest," *Glycoconjugate Journal*, 16:99-107 (1999).

Maras et al., "Molecular Cloning and Enzymatic Characterization of a Trichoderma *reeisi* 1,2-alpha-D-mannosidase," *J. Biotechnol.*, 77(2-3):255-263, 2000.

Maras et al., "In vivo synthesis of complex N-glycans by expression of human N-acetylglucosaminyltransferase..", FEBS Letters, vol. 452, pp. 365-370 (1999).

Martinet et al., "Modification of the protein glycosylation pathway in the methylotrophic yeast *Pichia pastoris,*" *Biotechnology Letters* 20(12): 1171-1177 (1998).

Maruyama et al., "A 1,2-alpha-D-Mannosidase from a Bacillus sp.: Purification, Characterization, and Mode of Action," *Carbohydrate Res.* 251:89-98 (1994.

McClure "Modeling the growth, survival and death of microorganisims in foods: the UK food micromodel approach," *Int. J. Food Microbiol.*, 23(3-4) 265-275 (1994).

McGarvey et al., "Expression of the rabies virus glycoprotein in transgenic tomatoes," *Bio-Technology* 13(13): 1484-1487 (1995).

Merkle et al., "Cloning, Expression, Purification, and Characterixation of the Murine Lysosomal Acid Alpha-Mannosidase," *Biochim Biophys Acta*, 1336(2): 132-46 (1997).

Merriam & Webster online dictionary, (2006) Merriam-Webster, Incorporated, definition of "domain" p. 1.

Miele et al., "Glycosylation Properties of the *Pichia pastoris*-Expressed Recombinant Kringle 2 Domain of Tissue-Type Plasminogen Activator," *Biotechnol. Appl. Biochem.*, 25:151-157 (1997).

Mimura et al., "The influence of glycosylation on the thermal stability and effector function expression of human IgG1-Fc: properties of a series of truncated glycoforms", Molecular Immunology, vol. 37, pp. 697-706 (2000).

Minowa et al., "cDNA cloning and expression of bovine UDP-N-acetylglucosamine: . . . ", J. Biol. Chem., vol. 273, pp. 11556-11562 (1998).

Moens and Vanderleyden, "Glycoproteins in prokaryotes," Arc. Microbiol. 168:169-175 (1997).

Montesino et al., "Characterization of the oligosaccharides assembled on the pichia pastoris-expressed recombinant aspartic protease", Glycobio., pp. 1037-1043 (2000).

Moore and Spiro, "Characterization of the Endomannosidase Pathway for the Processing of *N*-Linked Oligosaccharides in Glucosidase II-deficient and Parent Mouse Lymphoma Cells," *J. Biol. Chem* 267(12):8443-8451 (1992).

Moremen, "Golgi α-mannosidase II deficiency in vertebrate systems: implications for asparagine-linked oligosaccharide processing in mammals," *Biochimica Biophysica Acta*, 1573: 225-235 (2002).

Moremen et al., "Biosynthesis and Modification of Golgi Mannosidase II in HeLa and 3T3 Cells," *J. Biol. Chem.*, 260(11): 6654-6662 (1985).

Moremen et al., "Topology of Mannosidase II in Rat Liver Golgi Membranes and Release of the Catalytic Domain by Selective Proteolysis," *J. Biol. Chem.*, 261(23): 10945-10951 (1986).

Moremen, "Isolation of a Rat Liver Golgi Mannosidase II Clone by Mixed Oligonucleotide-Primed Amplication of cDNA," *Proc. Natl. Acad. Sci.*, USA Jul. 1989;86(14):5276-80.

Moremen et al., "Isolation, Characterization, and Expression of cDNAs Encoding Murine ∀-Mannosidase II, a Golgi Enzyme that Controls Conversion of High Mannose to Complex N-Glycans," *Journal of Cell Biology*, Dec. 1991; 115(6):1521-34.

Moremen et al., "Glycosidases of the Asparagine-Linked Oligosaccharide Processing Pathway," *Glycobiology* 4(2): 113-125 (1994).

Morin-Ganet et al., "Morphogenesis and Dynamics of the Yeast Golgi Apparatus", Traffic, 1(1):56-68 (2000).

Nakanishi-Shindo et al., "Structure of the N-Linked Oligosaccharides That Show the Complete Loss of α-1,6-Polymannose Outer Chain from *och1*, *och1 mnn1*, and *och1 mnn1 alg3* Mutants in *Saccharomyces cerevisiae,*" *J. Biol. Chem.*, 268(35):26338-45 (1993).

Nakayama et al., "OCHl1 Encodes a Novel Membrane Bound Mannosyltransferase: Outer Chain Elongation of Asparagine-Linked Oligosaccharides," *Embo J.*, 11(7):2511-19, 1992.

(56) References Cited

OTHER PUBLICATIONS

Nakayama et al. "Substrate Specificity of ∀-1,6-Mannosylatransferase that Initiates N-Linked Mannose Outer Chain Elongation in *Saccharomyces cerevisiae*", *FEBS Lett.*, 412(3):547-50, 1997.

Narasimhan et al., "Control of Glycoprotein Synthesis", J. Biol. Chem., 257:10235:42 (1982).

Neiman et al., "*Saccharomyces cerevisiae* HOC1, a Supressor of pkc 1, Encodes a Putative glycosyltransferase", Genetics, 145(3):637-645 (1997).

Nikawa et al., "Structural and functional conservation of human and yeast HCP1 genese which can suppress the growth defect of the *Saccharomyces cerevisiae ire15* mutant," Gene 171(1): 107-111 (1996).

Ogawa et al., "Structure and Transcriptional Regulation of Human alpha-Mannosidase IIX (alpha-mannosidase II isotvae) Gene," *Eur. J. Biochem.*, 242(3): 446-453 (1996).

Ogunjimi et al., "High-level secretory expression of immunologically active intact antibody from the yeast pichia pastoris", Biotechnology Letters, 21:561-567 (1999).

Oh-eda et al., "Overexpression of the Golgi-Localized Enzyme ∀-mannosidase IIx in Chinese Hamster ovary Cells Results inthe Conversion of Hexamannosyl-N-acetylchitobiose to Tetramannosyl-N-acetylchitobiose in the N-glycan-processing Pathway," *Eur. J. Biochem.*, 268: 1280-1288 (2001).

Orlandi et al., "Cloning immunolglobulin variable domains for expression by the polymerase chain reaction", Proc. Natl., Acad. Sci. USA, 86:3833 (1988).

Pakula et al., "Monitoring the kinetics of glycoprotein synthesis and secretion in the filamentous fungus Trichoderma reesei . . . " Microbiology, vol. 146, pp. 223-232 (2000).

Papac et al., "A high-throughput microscale method to release N-linked oligosaccharides from glycoproteins for matrix-assisted laser desorption/ionization time-of-flight mass spectrometric analysis," *Glycobiology* 8(5): 445-454 (1998).

Pearson, "Rapid and Sensitive Sequence Comparison with FASTA", Methods Enzymol. 183:63-98 (1990).

Pena, et al., "Proton pumping and the internal pH of yeast cells, measured with pyranine introduced by electroporation", Journal of Bacteriology, vol. 177, No. 4, pp. 1017-1022 (1995).

Perez et al., "Transport of Sugar Nucleotides into the Lumen of Vesicles Derived from Rat Liver Rough Endoplasmic Reticulum and Golgi Apparatus," *Methods in Enzymology*, 138: 709-715 (1987).

Puglielli et al., "Reconstitution, Identification, and Purification of the Rat Liver Golgi Membrane GDP-fucose Transporter," *J. Biol. Chem.* 274(50): 35596-35600 (1999).

Rabouille et al., "The *Drosophila GMII* Gene Encodes Golgi α-mannosidase II," *J. Cell Sci.*, Oct. 1999;112(Pt 19): 3319-30.

Ragu et al., "Species-specific variation in glycosylation of IgG: evidence for the species-specific sialyation and branch-specific galactosylation and importance for engineering recombinant glycoprotein therapeutics", Glycobiology, 10(5):477-486 (2000).

Raju et al., "Analysis of glycoconjugates," Anal Biochem. 283(2): 123-124 (2000).

Raschke et al., "Genetic Control of Yeast Mannan Structure", J. Biol. Chem. 248(13):4660-66 (1973).

Ray et al., A Novel Glycosylation Phenotype Expressed by Lec23, a Chinese Hamster Ovary Mutant Deficient in α-Glucosidase I, *J. Biol. Chem.* 255(34):22818-22825 (1991).

Recinos et al., "Sequences of cDNAs encoding immunoglobulin heavy-and ligh-chain variable regions from two anti-dioxin monoclonal antibodies", Gene, 149:385-386 (1994).

Recinos et al., "Sequences of cDNAs encoding immunoglobulin heavy-and ligh-chain variable regions from two anti-dioxin monoclonal antibodies", Gene, 158:311-312 (1995).

Reichner et al., Recycling cell surface glycoproteins undergo limited ligosaccharide reprocessing in LEC1 mutant Chinese hamster ovary cells, Glycobiology, vol. 8, No. 12, pp. 1173-1182 (1998).

Reidhaar-Olson et al., "Combinatorial Cassett Mutagenesis as a proble of the informational content of protein sequences", Science, 241:53-57 (1988).

Reitman et al., "A Lectin-resistant Mouse Lymphoma Cell Line Is Deficient in Glucosidase II, a Glycoprotein-processing Enzyme," *J. Biol. Chem.* 257(17):10357-10363 (1982).

Ren et al., "Purification and Properties of a Golgi-Derived (alpha 1,2)-mannosidase-I from Baculovirus-infected Lepidopteran Insect Cells (IPLB-SF21AE) with Preferential Activity Toward Mannose6-N-Acetylglucosamine2," *Biochem.*, 34(8): 2489-2495 (1995).

Ripka, et al., "Two Chinese hamster ovary glycosylation mutants affected in the conversion of GDP-mannose to GDP-fucose", Biochemistry and Biophysics, vol. 294, No. 2, pp. 533-545 (1986).

Roberts, D.B.: "Drosophila Melanogaster GMII gene, exons 1-5" XP002293614, Database accession No. AJ132715, Abstract, Database EMBL, 1999.

Romero et al., "Ktr1P is an α-1,2-mannosyltransferase of *Saccharomyces cerevisiae,*" *Biochem. J.*, 321 (Pt 2): 289-295 (1997).

Romero et al., "Mutation of Arg$^{273}$ to Leu Alters the Specificity of the Yeast N-Glycan Processing Class I α1,2-Mannosidase," *J. Biol. Chem*, 275(15):11071-11074 (2000).

Roth et al., "The role of glucosidase II and endomannosidase in glucose trimming of asparagines-linked oligosaccharides," *Biochimie* 85:287-294 (2003).

Rothman et al., "Antibody-dependent cytotoxicity mediated by natural killer cells is enhanced by castonospermine-induced alterations of IgG glycosylation", Molecular Immunology, vol. 26, No. 12 pp. 1113-1123 (1989).

Rothstein et al., "Targeting, Disruption, Replacement and Allele Rescue: Integrative DNA Transformation in Yeast", Methods in Enzymology, 194:281 (1991).

Ruther et al., "c-fos expression interferes with thymus development in transgenic mice," *Cell* 53(6): 847-856 (1988).

Sakamoto et al., Molecular Cloning and Expression of CDNA Encoding Chicken UDP-N-acetyl-D-glucosamine (GlcNAc): GlcNAc β1-6(GlcNAc β1-2)-Man α1-R[GlcNAc) to Man]β1,4N-acetylglucosaminyltransferase VI, J. Biol. Chem. vol. 275, No. 46, pp. 36029-26034 (2000).

Salovuori et al., "Low molecular weight high-mannose type glycans in a secreted protein . . . ", Bio/Technology, vol. 5, pp. 152-156 (1987).

Sasai et al., "UDP-GlcNAc concentration is an important factor in the biosynthesis of β1,6-branched oligosaccharides: regulation based on the kinetic properties of N-acetylglucosaminytransferase V", Glycobiology, vol. 12, No. 2, pp. 119-127 (2002).

Sato et al., "Arabidopsis Thaliana DNA Chromosome 5, BAC clone F2G14 (Essa project)", XP002293613, Database accession No. AL391146, gene "F2G14_70" encoding "alpha-mannosidase-like protein" of protein_id="CACO1814.1" Abstract, Database EMBL Aug. 7, 2000.

Satoh et al., "Ciona intestinalis cDNA clone: ciego014e11, full insert sequence", XP002293611, Database accession No. AK116684, the whole document, Database EMBL (2002).

Schachter et al., "The 'Yellow Brick Road' to Branched Complex N-glycans," *Glycobiology* 1(5): 453-461, 1991.

Schneikert et al., "Characterization of a Novem Mouse Recombinant Processing alpha-mannosidase," *Glycobiology*, 4(4):445-450 (1994).

Schwientek et al., "Golgi Localization in Yeast is Mediated by the Membrane Anchor Region in Rat Liver Sialyltransferase," *J. Biol. Chem.*, 270(10):5483-5489 (1995).

Schwientek et al., "Golgi localization and in vivo activity of a mammalian glycosyltransferase..", J. of Biol. Chem., vol. 271, pp. 3398-3405 (1996).

Schlegel et al., XP-002293375, WO200160860-A2, Aug. 23, 2001, "Human prostate expression marker cDNA 29377".

Segawa et al., "*Schizosaccharomyces pombe* UDP-galatose transporter: identification of its functional form through cDNA cloning and expression in mammalian cells," *FEBS Letters*, 451(3): 295-298 (1999).

Shields, R. et al, "High Resolutin Mapping of the Binding Site on Human IgG1 for FcγRI, FcγRII, FcγRIII, and FcRn and Design of

(56) References Cited

OTHER PUBLICATIONS

IgG1 Variants with improved binding to the FcγR", The Journal of Biological Chemistry, vol. 276, No. 9, pp. 6591-6604 (2001).
Shields, R. et al., "Lack of fucose on human IgG1 N-linked oligosaccharide improves binding to human FcγRIII and antibody-dependent cellular toxicity", The Journal of Biological Chemistry, vol. 277, No. 30, pp. 26733-26740 (2002).
Shiha et al., "Functional characterization of human blood coagulation factor XIa using hybridoma antibodies", J. Biol. Chem. vol. 260, No. 19, pp. 10714-10719 (1985).
Shinkawa, et al., "The Absence of Fucose but not the presence of galactose or bisecting N-Acetylglucosamine of human IgG1 complex-type oligosaccharides shows the critical role of enhancing antibody-dependent cellular cytotoxicity," The Journal of Biological Chemistry, vol. 278, No. 5, pp. 3466-3473 (2003).
Shinn et al: "Arabidopsis Thaliana AT5g14950/F2G14_70 mRNA, complete cds." XP002293612, Database accession No. AY052707, Abstract, Database EMBL (2001).
Shitara, et al, "A new vector for the high level expression of chimeric antibodies in myeloma cells", Journal of Immunological Methods, vol. 167, pp. 271-278 (1994).
Sikorski et al., "A system of shuttle vectors and yeast host strains designed for efficient manipulation of DNA in *Saccharomyces cerevisiae,*" *Genetics* 122(1): 19-27 (1989).
Soderholm et al. "Vector for pop-in/pop-out Gene Replacement in *Pichia pastoris,*" *Biotchniques*, 31 (2):306-312 (2001).
Sommers et al., "Transport of Sugar Nucleotides into Rat Liver Golgi. A New Golgi Marker Activity," *J Biolog Chem*, 257(18): 10811-10817 (1982).
Spiro et al., "Definition of the Lectin-like Properties of the Molecular Chaperone, Calreticulin, and Demonstration of Its Copurification with Endomannosidase from Rat Liver Golgi," *J. Biol. Chem.* 271(19):11588-11594 (1996).
Spiro et al., "Molecular Cloning and Expression of Rat Liver Endo-α-mannosidase, an *N*-linked Oligosaccharide Processing Enzyme," *J. Biol. Chem.* 272(46):29356-29363 (1997).
Spiro and Spiro, "Use of recombinant endomannosidase for evaluation of the processing of *N*-linked oligosaccharides of glycoproteins and their oligosaccharide-lipid precursors," *Glycobiology* 10(5):521-529 (2000).
Spiro, "Glucose residues as key determinants in the biosynthesis and quality control of glycoproteins with N-linked oligosaccharides," Journal of Biological Chemistry, vol. 275, No. 46, pp. 35657-35660 (2000).
Strasser et al., "Molecular basis of N-acetylglucosaminyltransferase I deficiency", Biochem. J., vol. 387, pp. 385-391 (2005).
Stanely et al., "Complementation between mutants of CHO cells resistant to a variety of plant lectins", Somatic Cell Genet 3(4):391-405 (1977).
Staub et al., "High-yield production of a human therapeutic protein in tobacco chloroplasts," *Nature Biotechnology* 18(3): 333-338 (2000).
Stix, "Supercharging Protein Manufacture," Scientific Amer., vol. 290, pp. 32-33 (2004).
Suzuki et al., "Characterizaion of alpha-1,6-mannosyltransferase responsible for the synthesis of branched side chains in candida albicans mannan.", Eur J. Biochem, vol. 240, No. 1, pp. 37-44, (1996).
Svetina et al., "Expression of Catalytic Subunit of Bovine Enterokinase in the Filamentous Fungus Aspergillus Niger," *J. Biotechnol.*, 76(2-3): 245-251 (2000).
Swarnakar et al., XP-002293374, WO200297060-A2, Dec. 5, 2002, "Novel human carbohydrate associated polypeptide, useful in diagnosis, treatment and prevention . . ."
Swiss Prot P11655, dated Oct. 1989.
Swiss Prot P32906, dated Oct. 1993.
Swiss Prot P39107, dated Feb. 1995.
Swiss Prot P50108, dated Oct. 1996.
Swiss Prot P53008, dated Oct. 1996.

Takeuchi, "Trial for molecular breeding of yeast for the production of glycoprotein therapeutics," *Trends in Glycoscience and Glycotechnology* 9:S29-S35 (1997).
Tang et al., XP-002293372, WO2003025148-A2, Mar. 27, 2003, "New Polynucleotides and secreted proteins, useful for treating myeloid or lymphoid cell disorders.."
Tang et al., XP-002293373, WO2003025148-A2, Mar. 27, 2003, "New Polynucleotides and secreted proteins, useful for treating myeloid or lymphoid cell disorders.."
Tatara et al., J. of Biol. Chem., vol. 278 (2003), pp. 25289-25294, "Identification of catalytic residues of Ca2+-independent . . ."
Teixeira et al. (2005) Antifungal susceptibility and pathogenic potential of environmental isolated filamentous fungi compared with colonizing agents in immunocompromised patients. Mycopathologia., vol. 160, No. 2, pp. 129-135 (2005).
Terness et al., "Idiotypic vaccine for treatment of human B-cell lymphoma", Hum. Immunol., 56:17-27 (1997).
Tremblay et al., "Cloning and expression of a specific human α1,2-mannosidase that trims Man9GlcNac2 to Man8GlcNac2 isomer B during N-glycan biosynthesis", Glycobiology, vol. 9, No. 10, pp. 1073-1078 (1999).
Tremblay et al., "Characterization of a cDNA encoding a novel human Golgi α1,2-Mannosidase (IC) involved in N-Glycan Biosynthesis," The Journal of Biological Chemistry, vol. 275, No. 41, pp. 31655-31660 (2000).
Tremblay et al., "Molecular cloning, chromosomal mapping and tissue-specific expression of a novel human α-1,2-mannosidase gene involved in N-glycan maturation", Glycobiology, 8(6):585-595 (1998).
Tsuji-Hayashi et al., "A potential endogenous ligand of annexin IV in the Exocrine pancreas", The Journal of Biological Chemistry, 277(49):47493-47499 (2002).
Tsujikawa et al., "Secretion of a variant of human single-chain urokinase-type plasminogen activator without an N-glycosylation site in the methylotrophic yeast, pichia patoris and characterization of the secreted product:", Yeast, vol. 12, No. 6, pp. 541-553 (1996).
Umana et al., "Tetracycline-Regulated Overexpression of glycosyltransferase in Chinese hamster ovary cells", Biotechnol. Bioeng., 65(5):542-549 (1999).
Umaña et al., "Engineered Glycoforms of an Antineuroblastoma IgG1 with Optimized Antibody-Dependent Cellular Cytotoxic Activity," *Nature Biotechnology*, 17(1):176-80 (1999).
Vervecken et al., "In vivo synthesis of mammalian-like . . . ", Appl. Environ. Microbiol., vol. 70, pp. 2639-2646 (2004).
Voet et al., Biochemistry, John Wiley & Sons (1990), pp. 266-267, Section 10-3. Glycoproteins.
Ware et al., "Expression of Human Platelet Glycoprotein Ib-Alpha in Transgenic Mice," *Thrombosis and Haemostasis* 69(6): p. 1194 (1993).
Weikert et al., "Engineering Chinese Hamster Ovary Cells to Maximize Sialic Acid Content of Recombinant Glycoproteins", *Nature Biotechnology*, 17(11): 1116-1121, Nov. 1999.
Weng et al., "Evaluation of the early processing routes of N-linked oligosaccharides of glycoproteins through the characterization of Man*GlcNAc2 . . . ", Glycobiology, vol. 6, pp. 861-868 (1996).
Welschof et al., "Amino acid sequence based PCR primers for amplification of rearranged human heavy and light chain immunolglobulin variable region genes", J. Immunol. Methods, 179:203-214 (1995).
Werner et al., "Appropriate Mammalian Expression Systems for Biopharmaceuticals," *Arzneimittelforschung*, Aug. 1998;48(8):870-80.
Wikipidia encyclopedia definition (2008): Signal Peptide & Structure Information, pp. 1-4.
Wildt et al., "The Humanization of N-Glycosylation Pathways in Yeast", Nat. Rev. Microbiol., vol. 3, No. 2, pp. 119-128 (2005).
Wiggins et al., "Activity of the yeast MNN1 alpha-1,3-mannosyltransferase requires a notif conserved in many other families of glycosyltransfereases," *Proc. Nat. Acad. Sci. USA* 95(14): 7945-7950 (1998).
Xie, et al., "Direct demonstration of MuSK involvement in acetylcholine receptor clustering through identification of agonist ScFv", Nature Biotechnology, vol. 15, pp. 768-771 (1997).

(56) References Cited

OTHER PUBLICATIONS

Yamane-Ohnuki et al., "Establishment of FUT8 knockout Chinese hamster ovary cells: An ideal host cel line for producing . . . ", Biotech, Bioengin., vol. 87, pp. 614-622 (2004).
Yamashita et al., "An α-Mannosidase purified from Aspergillus Saitoi is specific for α1,2 linkages," Biochemical and Biophysical Research Communications 96(3): 1335-1342 (1980).
Yang et al., "Glycosylation and proteolytic processing of 70 kDa C-terminal recombinant polypeptides of Plasmodium falciparum merozoite surface protein 1 expressed in mammalian cells," Glycobiology, 9(12): (1999) 1347-55.
Yang et al., "Effects of Ammonia on CHO Cell Growth, Erythropoietin Production, and Glycosylation", Biotechnol Bioeng., 68(4): 370-80 (2000).
Yip et al., "Cloning and analysis of the *Saccharomyces cerevisiae* MNN9 and MNN1 genes required for complex glycosylation of secreted proteins," Proc. Natl. Acad. Sci. USA, 91(7): 2723-2727 (1994).
Yoko-o et al., "Schizosaccharomyces Pombe Och1(+) Encodes Alpha-1,6-Mannosyltranferase that is involved in Outer Chain Elongation of N-Linked Oligosaccharides," FEBS Lett., 489(1): 75-80 (2001).
Yoshida et al., "1-2-alpha-D-mannosidase from Penicillium citriunum: molecular and enzymic properties of two isoenzymes," Biochem. J. 290 (Pt2): 349-354 (1993).
Yoshida et al., "Expression and charaterization of rat UDP-N-acetylgluocosamine: α-3-D-mannoside β-1,2-N-acetylglucosaminyltransferase I in *Saccharomyces cerevisiae*," Glycobiology, 9 (1): 53-58 (1999).
Yoshida et al., "Molecular cloning and nucleotide sequence of the genomic DNA for 1-2-alpha-D-mannosidase gene, msdC from Penicillium citriunum," *Biochem. Biophys. Acta*. vol. 1263, No. 2 pp. 159-162 (1995).
Zerangue et al, "Analysis of endoplasmic reticulum trafficking singals by combinatorial screening in mammalian cells", Proc. Natl. Acad. Sci. USA, vol. 98, No. 5, pp. 2431-2436 (2001).
Zhang and Madden, "PowerBLAST: a new network BLAST application for interactive or automated sequence analysis and annotation", Genome Res. 7:649-656 (1997).
Zhu et al., "Structural studies of alpha-N-acetylgalactosaminidase: Effect of glycosylation..", Archives of Biochem. & Biophysics, vol. 352, pp. 1-8 (1998).
Zuber et al., "Golgi Apparatus Immunolocalization of Endomannosidase Suggests Post-Endoplasmic Reticulum Glucose Trimming: Implications for Quality Control," *Mol. Bio. of the Cell*, 11:4227-4240 (2000).
Genbank Accession No. NM 00528, dated Sep. 25, 2005.
Genbank Accession No. AF005034, dated Jul. 10, 1997.
Genbank Accession No. AF106080, dated Apr. 17, 1999.
Genbank Accession No. AK116684, dated Nov. 30, 2002.
Genbank Accession No. D55649, dated Feb. 7, 2003.
Genbank Accession No. NM__073594, dated Aug. 19, 2005.
Genbank Accession No. NM__121499, dated Nov. 4, 2005.
Genbank Accession No. U31520, dated Dec. 13, 1995.
Genbank Accession No. X77652, dated Apr. 24, 1995.
Genbank Accession No. XM__218816, dated Apr. 24, 1995.
Genbank Accession No. NM 002406, dated Sep. 23, 2005.
Genbank Accession No. CAA98114, dated Aug. 9, 2005.
Genbank Accession No. NM__088548 (Genbank AN 6678787), dated Apr. 7, 2003.
Genbank Accession No. NM006715, dated Oct. 18, 2005.
Genbank Accession No. X77652 (1995).
Genbank Accession No. X61172, dated Apr. 18, 2005.
Opposition Brief filed by Novozymes A/S for EP1297172 B1 (English Translation) (2005).
Opposition Brief filed (French) by Glycode SAS for EP1297172 B1 (English Translation) (2006).
Opposition Brief filed by Glycode SAS for EP1297172 B1 (English Translation) (2006).
Preliminary EPO non-binding opinion of the opposition division for EP1297172 B1 (2007).
Pantee's Reply to the Notice of Opposition for EP1297172 B1 (2007).
Applicants response of Apr. 18, 2008 to Office Action re U.S. Appl. No. 11/187,066.
Applicants response to Apr. 11, 2008 to Office Action re U.S. Appl. No. 11/187,196.
Appliants response to Apr. 11, 2008 to Office Action re U.S. Appl. No. 11/187,113.
File History of U.S. Appl. No. 11/249,061 (corresponding case), Oct. 2009.
Opposition Brief filed by Novartis against EP1597379 (Feb. 15, 2010).
Opposition Brief filed by Novozymes A/S for EP1297172 B1 (2007).
Further submission by Patentee in opposition proceeding against EP 1297172B1 (2007).
Opinion of the Opposition Division for EP1297172B1 (2007).
Grounds of Appeal for EP 1297172 B1 (2008).
Response by Glycode to Grounds of Appeal for EP 1297172 B1 (2008) (English Translation of French Document).
Preliminary Opinion of Appeal Board for EP 1297172 B1 (2010).
O'Brian et al., "Mass Spectrometry of Cardiac Calsequestrin Characterizes Microheterogeneity Unique to Heart and Indicative of Complex Intracellular Transit", The Journal of Biological Chemistry, vol. 277, No. 40, pp. 37154-37160 (2002).
Jigami & Kainuma, Protein Nucleic Acid and Enzyme (1998) vol. 43, pp. 2604-2610—Non-English.
Foreign Office Action corresponding to Jigami & Kainuma, Aug. 1999.

* cited by examiner

>gi|20547442|ref|XP_113472.1| (XM_113472) hypothetical protein FLJ12838 [Homo sapiens]
Length = 290

Score = 526 bits (1354), Expect = e-148
Identities = 258/290 (88%), Positives = 276/290 (94%)

```
Query: 162  MKQMRSASIGVLALSMYPPDASDENGEATDYLVPTILDKAHKYNLKVTFHIEPYSNRDDQ  221
            M+QMRSASIGVLALSMYPPD +DENGE TD LVPTILDKAHKYNLKVTFHIEPYSNRDDQ
Sbjct: 1    MRQMRSASIGVLALSMYPPDVNDENGEPTDNLVPTILDKAHKYNLKVTFHIEPYSNRDDQ  60

Query: 222  NMHQNVKYIIDKYGNHPAFYRYKTRMGHSLPMFYIYDSYITKPKTWANLLTPSGSQSVRG  281
            NM++NVKYIIDKYGNHPAFYRYKT+ G++LPMFY+YDSYITKP+ WANLLT SGS+S+R
Sbjct: 61   NMYKNVKYIIDKYGNHPAFYRYKTKTGNALPMFYVYDSYITKPEKWANLLTTSGSRSIRN  120

Query: 282  SPYDGLFIALLVEEKHKYDILQSGFDGIYTYFATNGFTYGSSHQNMNKLKSFCEKNMMIF  341
            SPYDGLFIALLVEEKHKYDILQSGFDGIYTYFATNGFTYGSSHQNW  LK FC+K N+IF
Sbjct: 121  SPYDGLFIALLVEEKHKYDILQSGFDGIYTYFATNGFTYGSSHQNWASLKLFCDKYNLIF  180

Query: 343  IPSVGPGYIDTSIRPWNTQNTRNRINGKYYEVGLSAALQTQPSLISITSFNEWHEGTQIE  401
            IPSVGPGYIDTSIRPWNTQNTRNRINGKYYE+GLSAALQT+PSLISITSFNEWHEGTQIE
Sbjct: 181  IPSVGPGYIDTSIRPWNTQNTRNRINGKYYEIGLSAALQTRPSLISITSFNEWHEGTQIE  240

Query: 402  KAVPKRTANTVYLDYRPHKPSLYLEITRKWSEKYSKERMTYALDQQLPAS  451
            KAVPKRT+NTVYLDYRPHKP LYLE+TRKWSEKYSKER TYALD+QLP S
Sbjct: 241  KAVPKRTSNTVYLDYRPHKPGLYLELTRKWSEKYSKERATYALDRQLPVS  290
```

FIG.3A

>gi|18031878|gb|AAL07306.1| (AY048774) mandaselin short form [Homo sapiens]
Length = 195

Score = 49.7 bits (117), Expect = 9e-06
Identities = 22/23 (95%), Positives = 23/23 (99%)

Query:   1  MRQMRSASIGVLALSWYPPDVND  23
            MRQMRSASIGVLALSWYPPDVN+
Sbjct: 173  MRQMRSASIGVLALSWYPPDVNE  195

FIG.3B

>gi|18031878|gb|AAL07306.1| mandaselin short form [Homo sapiens]
MAKFRRRTCIILALFILFIFSLMMGLKMLRPNTATFGAPFGLDLLPELHQRTIHLGKNFDFQKSDRINSE
TNTKNLKSVEITMKPSKASELNLDELPPLNNYLHVFYYSWYGNPQFDGKYIHMNHPVLEHWDPRIAKNYP
QGRHNPPDDIGSSFYPELGSYSSRDPSVIETHMRQMRSASIGVLALSWYPPDVNE

FIG.3C

```
  1 ATGGCAAAGTTTCGGAGAAGGACTTGCATCATTTGGCACTTTTTATTCTATTTATTTCTCTGATGATGGGTTTAAAAATGCTGAGACCAAA
  1▸ M  A  K  F  R  R  R  T  C  I  L  A  L  F  I  L  F  I  F  S  L  M  M  G  L  K  M  L  R  P  N

96 TACAGCTACTTTTGGAGCTCCTTTTGGACTTGACCTTCTTCCAGAACTTCATCAACGAACTATTCATTGGGAAAAATTTGATTCCAAAGA
 32▸ T  A  T  F  G  A  P  F  G  L  D  L  L  P  E  L  H  Q  R  T  I  H  L  G  K  N  F  D  F  Q  K

191 GTGACAGAATCAACAGTGAAACAAGAATTTAAAAATGTTGAAATCACTATGAAACCTTCCAAAGCCTCTGAACTTAACTTGGATGAA
 64▸ S  D  R  I  N  S  E  T  N  T  K  N  L  K  S  V  E  I  T  M  K  P  S  K  A  S  E  L  N  L  D  E

286 CTACCACCTCTGAACAATTATCTACATGTATTTATTACAGTTGGTAATGGTAAATATACATTGATGTAAATATACATTGGAATCATCCAGT
 96▸ L  P  P  L  N  N  Y  L  H  V  F  Y  Y  S  W  Y  G  N  P  Q  F  D  G  K  Y  I  H  W  N  H  P  V

381 GTTAGAGCATTGGGACCCTAGAATAGCCAAGAATTATCCTCTGTCATAGAAACTCACAGAGACAAATGCGCTCAGCTTCAATTGGTG
127▸ L  E  H  W  D  P  R  I  A  K  N  Y  P  Q  G  R  H  N  P  P  D  D  I  G  S  S  F  Y  P  E  L

476 GAAGTTACAGTTCTCGGATCCTTCTGTCATAGAAACTCACAGAGACAAATGCGCTCAGCTTCAATTGGTGTACTAGCCCTCTCTT
159▸ G  S  Y  S  S  R  D  P  S  V  I  E  T  H  M  R  Q  M  R  S  A  S  I  G  V  L  A  L  S

563 GGTTACCCACCTGATGTAAATGATGAGAACGGAGAACCTACTGATAACTTGGTACCCACTATTTTGGATAAAGCTCATAAATATAACCTAAA
188▸ W  Y  P  P  D  V  N  D  E  N  G  E  P  T  D  N  L  V  P  T  I  L  D  K  A  H  K  Y  N  L  K

654 GGTTACTTTTCACATAGAACCATATAGCAATCGAGATGATCAAAAACATGTACAAAAAATGTCAAGTATATTATAGACAAATATGAAATCATCCGG
218▸ V  T  F  H  I  E  P  Y  S  N  R  D  D  Q  N  M  Y  K  N  V  K  Y  I  I  D  K  Y  G  N  H  P
```

FIG. 4-1

749  CCTTTTACAGGTACAAGACGAAGACTGGCAATGCTCTTCCTATGTTTTATGTCTATGATTCCTATATTACCAAGCCTGAAAAATGGGCCAATCTG
250▶ A  F  Y  R  Y  K  T  K  T  G  N  A  L  P  M  F  Y  V  Y  D  S  Y  I  T  K  P  E  K  W  A  N  L

844  TTAACCACCTCAGGTCTCCGAGTATTCCAATTCTCCTTATGATGGACTGTTTATTGCCCTTCTGGTAGAAGAAAAACATAAGTATGATATTCT
282▶ L  T  T  S  G  S  R  S  I  R  N  S  P  Y  D  G  L  F  I  A  L  L  V  E  E  K  H  K  Y  D  I  L

939  TCAAAGTGGTTTGATGGAATTTACACATATTTTGCCACAAATGGCTTACTTATGGCTCATCACACATCAGAATTGGGCTAGCCTAAAATTAATTT
313▶ Q  S  G  F  D  G  I  Y  T  Y  F  A  T  N  G  F  T  Y  G  S  S  H  Q  N  W  A  S  L  K  L  I

1034 GTGATAAATACAACTTAATATATTATCCCAAGTGTGGGCCCAGGATACATAGATACCAGCATCCGTCCATGGAACACGCAAAACACTCGGAACCGA
345▶ C  D  K  Y  N  L  I  F  I  P  S  V  G  P  G  Y  I  D  T  S  I  R  P  W  N  T  Q  N  T  R  N  R

1129 ATCAAATGGAAGTATTATGAAATTGGTCTGAGTGCCGCACTTCAGACACGCCCAGCTTAATTCTATCACCTCTTTTAATGAGTGGCATGAAGG
377▶ I  N  G  K  Y  Y  E  I  G  L  S  A  A  L  Q  T  R  P  S  L  I  S  I  T  S  F  N  E  W  H  E  G

1224 AACTCAGATTGAAAAAGCTGTTCCCAAAGAACCAGTAATACAGTGTACCTAGATTACGTCCTCATAAACCAGGTCTTTACCTAGAACTGACTC
408▶ T  Q  I  E  K  A  V  P  K  R  T  S  N  T  V  V  L  D  Y  R  P  H  K  P  G  L  Y  L  E  L  T

1319 GCAAGTGGTCTCTGAAAAATACAGTAAGGAAAGAGAGCAACTTATGCATTAGATCGGCCAGCTGCCTGTTTCTTAA
440▶ R  K  W  S  E  K  Y  S  K  E  R  A  T  Y  A  L  D  R  Q  L  P  V  S

FIG. 4-2

1   ATGGCAAAATTTCGAAGAAGGACCTGCATCCTTTTGTCACTTTTTATTCTCATTATTTTTCTGATGATGGGCTTAAAGATGCTGTGGCCAA
1▸  M  A  K  F  R  R  R  T  C  | I  L  L  S  L  F  I  L  F  I  F  S  L  M  M  G  | L  K  M  L  W  P

95  ACGCAGCATCCTTTGGACTCCTTTGACTTGACCTCCTTCCAGAACTTCATCCACTAAATGGGCATTCGGGAAACAAAGCTGACTTCCAAAG
32▸ N  A  A  S  F  G  P  P  F  G  L  D  L  L  P  E  L  H  P  L  N  A  H  S  G  N  K  A  D  F  Q  R

189 GAGTGATAGAATCAACATGGAAACAAACACCAAGGCTTAAAAAGGGCCTGGCATGACTGTGCTGCCAGCCAAAGCCTCTGAGGTGAACCTGGAA
63▸ S  D  R  I  N  M  E  T  N  T  K  A  L  K  G  A  G  M  T  V  L  P  A  K  A  S  E  V  N  L  E

283 GAACTACCTCCTCTGAATTACTTTTTACATGCATTTTATTACAGTTGGTATGGAAATCCACAGTTTGATGGTAAATATACACTGGAATCATC
95▸ E  L  P  P  L  N  Y  F  L  H  A  F  Y  Y  S  W  Y  G  N  P  Q  F  D  G  K  Y  I  H  W  N  H

377 CGGTCCTGGAACACTGGGACCCTCGAGACCCTTCTGTCATAGAAAACTCACAGAAACAATCCCGCTCAGCCTCAATTGGAGTTCTGGCCCCTGTCTTGG
126▸ P  V  L  E  H  W  D  P  R  I  A  K  N  Y  P  Q  G  Q  H  S  P  P  D  D  I  G  S  S  F  Y  P  E

471 GTTAGGAAGTTACAGCTCTCGAGATCCTTCCAGCGTCATAGAAACTCACATGAAGCAAATGCGATCAGCCAGCATTTGGATAAAGCTCATAAATATAATCTGAAGGTCA
157▸ L  G  S  Y  S  S  R  D  P  S  V  I  E  T  H  M  K  Q  M  R  S  A  S  I  G  V  L  A  L  S  W

565 TACCCACCTGATTCAAGGATGACAATGGCAAGCTACTGATCACTTGGTGCCAACCATTTGGATAAAGCTCATAAATATAATCTGAAGGTCA
189▸ Y  P  P  D  S  R  D  D  D  N  G  E  A  T  D  H  L  V  P  T  I  L  D  K  A  H  K  Y  N  L  K  V

659 CTTTTCACATAGAGCCATATAGCAATCGAGATGATCAGAGACAAATGCATCAAAATATCAAGTATATTATAGACAAATATGGAAACCATCCAGCCTT
220▸ T  F  H  I  E  P  Y  S  N  R  D  D  Q  N  M  H  Q  N  I  K  Y  I  I  D  K  Y  G  N  H  P  A  F

FIG.6-1

753  TTATAGATACAAGACCAGGACTGGCATTCTCTGCCATGTTTATGTCTATGATTCTTACATCACAAAGCCTACAATATGGGCCAATCTGTTA
251▶  Y  R  Y  K  T  R  T  G  H  S  L  P  M  F  Y  V  Y  D  S  Y  I  T  K  P  T  I  W  A  N  L  L

847  ACACCCTCGGATCTCAGAGTGTTCGCAGTTCTCTCTCTTTATGATGGATTGTTTATTGCACTCTAGTAGAAGAAAAGCATAAAAATGATATTCTTC
283▶  T  P  S  G  S  Q  S  V  R  S  S  L  Y  D  G  L  F  I  A  L  L  V  E  E  K  H  K  N  D  I  L

941  AGAGTGGTTTTGATGGTATTATACACATATTTGCCACAAATGGCTTACATATGGCTCATCTCATCAGAATTGGAATAACCTGAAATCCTTTG
314▶  Q  S  G  F  D  G  I  Y  T  Y  F  A  T  N  G  F  T  Y  G  S  S  H  Q  N  W  N  N  L  K  S  F  C

1035 TGAAAGAACAACTTGATGTTTATCCCAAGTGTAGGCCCAGGATACATAAGCATCCGACATGGAACACCCGGAACACCCGGAACACAGA
345▶  E  K  N  N  L  M  F  I  P  S  V  G  P  G  Y  I  D  T  S  I  R  P  W  N  T  Q  N  T  R  N  R

1129 GTCAATGGGAAGTATTATGAAGTTGGTCTAAGTGCTGCAGCTCTGCAGACCCACCCCCAGTTTAATTTCCATCACCTCTTCAATGAGTGGCATGAAG
377▶  V  N  G  K  Y  Y  E  V  G  L  S  A  A  L  Q  T  H  P  S  L  I  S  I  T  S  F  N  E  W  H  E

1223 GAACTCAAATTGAAAGGGCTGTCCCAAAAGAACTGTAACACGATATACCTGGATTACCGCCCATAAGCCAAGTCTTTATCTAGAACTAAC
408▶  G  T  Q  I  E  K  A  V  P  K  R  T  A  N  T  I  Y  L  D  Y  R  P  H  K  P  S  L  Y  L  E  L  T

1317 TCGAAAGTGGTCTGAAAAATTCAGTAAGGAAAGAATGACGTATGCATTGGATCAACAGCAGCCTGCTTCATAA
439▶  R  K  W  S  E  K  F  S  K  E  R  M  T  Y  A  L  D  Q  Q  Q  P  A  S

FIG.6-2

| | | |
|---|---|---|
| 1 | MAKFRRTCILALFLFSLMMGLKMLRPNTATFGAPF | hEndo |
| 1 | MAKFRRTCILSLFLFSLMMGLKMLWRNAASFGRPF | mEndo |
| 1 | ---------------MATYSEGMMGCSSVGRCFSSTLSRII | rEndo |
| 41 | GLDLLPELHQRTIHLGKNFDFQKSDRINSETNTKNLKSVE | hEndo |
| 41 | GLDLLPELHPLNAHSGNKADFQRSDRINMETNTKALKGAG | mEndo |
| 31 | TL-VATSMKSTPRVLENKADFQRSDRIDMETNTKDLKGAG | rEndo |
| 81 | ITMKPSKASELNDELPPLNNYLHVFYYSWYGNPQFDGKY | hEndo |
| 81 | MTVLRAKASEVNLEELPPLNYFLHAFYSWYGNPQFDGKY | mEndo |
| 70 | VTVHPPRASEVNLEELPPLNYFVHAFYSWYGNPQFDGKY | rEndo |
| 121 | IHWNHPVLEHWDPRRIAKNYPQGRHNPPDDIGSSFYPELGS | hEndo |
| 121 | IHWNHPVLEHWDPRRIAKNYPQGQHSPPDDIGSSFYPELGS | mEndo |
| 110 | VHWNHPVLEHWDPRRIAKNYPQGRHSPPDDIGSSFYPELGS | rEndo |
| 161 | YSSRDPSVIETHMRQMRSASIGVLALSWYPPDVNDENGEP | hEndo |
| 161 | YSSRDPSVIETHMKQMRSASIGVLALSWYPPDSRDDNGEA | mEndo |
| 150 | YSSRDPSVIETHMKQMRSASIGVLALSWYPPDASQENGEA | rEndo |
| 201 | DNLVPTILDKAHKYNLKVTFHIEPYSNRDDQNMYKNVKY | hEndo |
| 201 | HLVPTILDKAHKYNLKVTFHIEPYSNRDDQNMHQNIKY | mEndo |
| 190 | DYLVPTILDKAHKYNLKVTFHIEPYSNRDDQNMHQNVKY | rEndo |

FIG.7-1

| | | |
|---|---|---|
| 241 IDKYGNHPAFYRKTKTGNALPMFYVYDSYITKPEKWAN | hEndo |
| 241 IDKYGNHPAFYRKTRTGHSLPMFYVYDSYITKPTIWAN | mEndo |
| 230 IDKYGNHPAFYRKTRMGHSLPMFYIYDSYITKPKTWAN | rEndo |

| | |
|---|---|
| 281 LITSGSRSIRNSPYDGLFIALLVEEKHKYDILQSGFDGI | hEndo |
| 281 LLTPSGSQSVRSSLYDGLFIALLVEEKHKNDILQSGFDGI | mEndo |
| 270 LLTPSGSQSVRGSPYDGLFIALLVEEKHKYDILQSGFDGI | rEndo |

| | |
|---|---|
| 321 YTYFATNGFTYGSSHQNWASLKLIGDKYNLIFIPSVGPGY | hEndo |
| 321 YTFATNGFTYGSSHQNWNNLKSFGEKNNLMFIPSVGPGY | mEndo |
| 310 YTYFATNGFTYGSSHQNWNKLKSFGEKNMIFIRSVGPGY | rEndo |

| | |
|---|---|
| 361 IDTSIRPWNTQNTRNRINGKYYEIGLSAALQTRPSLISIT | hEndo |
| 361 IDTSIRPWNTQNTRNRVNGKYYEVGLSAALQTHPSLISIT | mEndo |
| 350 IDTSIRPWNTQNTRNRINGKYYEVGLSAALQTQRPSLISIT | rEndo |

| | |
|---|---|
| 401 SFNEWHEGTQIEKAVPKRTSNTVYLDYRPHKPGLYLELTR | hEndo |
| 401 SFNEWHEGTQIEKAVPKRTANTIYLDYRPHKPSLYLELTR | mEndo |
| 390 SFNEWHEGTQIEKAVPKRTANTVYLDYRPHKPSLYLEITR | rEndo |

| | |
|---|---|
| 441 KWSEKYSKERATYALDRQLPVS | hEndo |
| 441 KWSEKFSKERMTYALDQQPAS | mEndo |
| 430 KWSEKYSKERMTYALDQQLPAS | rEndo |

FIG. 7-2

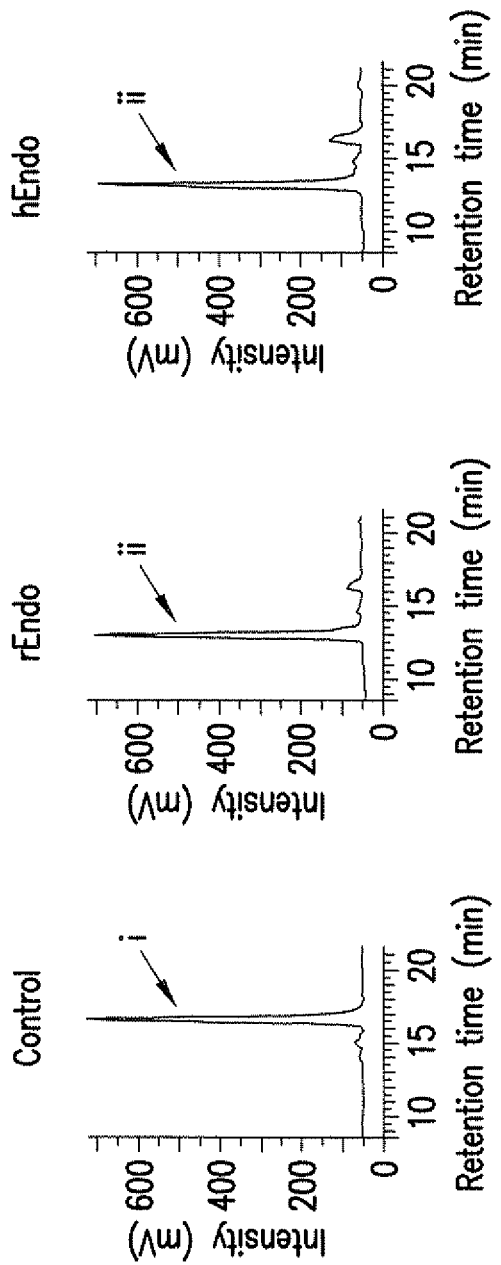

SEQUENCE LISTING

```
<160> NUMBER OF SEQ ID NOS: 29

<210> SEQ ID NO 1
<211> LENGTH: 1389
<212> TYPE: DNA
<213> ORGANISM: Homo sapiens
<220> FEATURE:
<221> NAME/KEY: CDS
<222> LOCATION: (1)..(1386)

<400> SEQUENCE: 1
```

```
atg gca aag ttt cgg aga agg act tgc atc att ttg gca ctt ttt att        48
Met Ala Lys Phe Arg Arg Arg Thr Cys Ile Ile Leu Ala Leu Phe Ile
 1               5                  10                  15 cta ttt att ttc tct ctg atg atg ggt tta aaa atg ctg aga cca aat        96
Leu Phe Ile Phe Ser Leu Met Met Gly Leu Lys Met Leu Arg Pro Asn
            20                  25                  30 aca gct act ttt gga gct cct ttt gga ctt gac ctt ctt cca gaa ctt       144
Thr Ala Thr Phe Gly Ala Pro Phe Gly Leu Asp Leu Leu Pro Glu Leu
        35                  40                  45 cat caa cga act att cat ttg ggg aaa aat ttt gat ttc caa aag agt       192
His Gln Arg Thr Ile His Leu Gly Lys Asn Phe Asp Phe Gln Lys Ser
    50                  55                  60 gac aga atc aac agt gaa aca aat acc aag aat tta aaa agt gtt gaa       240
Asp Arg Ile Asn Ser Glu Thr Asn Thr Lys Asn Leu Lys Ser Val Glu
65                  70                  75                  80 atc act atg aaa cct tcc aaa gcc tct gaa ctt aac ttg gat gaa cta       288
Ile Thr Met Lys Pro Ser Lys Ala Ser Glu Leu Asn Leu Asp Glu Leu
                85                  90                  95 cca cct ctg aac aat tat cta cat gta ttt tat tac agt tgg tat gga       336
Pro Pro Leu Asn Asn Tyr Leu His Val Phe Tyr Tyr Ser Trp Tyr Gly
            100                 105                 110 aat cca caa ttt gat ggt aaa tat ata cat tgg aat cat cca gtg tta       384
Asn Pro Gln Phe Asp Gly Lys Tyr Ile His Trp Asn His Pro Val Leu
        115                 120                 125 gag cat tgg gac cct aga ata gcc aag aat tat cca caa ggg aga cac       432
Glu His Trp Asp Pro Arg Ile Ala Lys Asn Tyr Pro Gln Gly Arg His
    130                 135                 140 aac cct cca gat gac att ggc tcc agc ttt tat cct gaa ttg gga agt       480
Asn Pro Pro Asp Asp Ile Gly Ser Ser Phe Tyr Pro Glu Leu Gly Ser
145                 150                 155                 160 tac agt tct cgg gat cct tct gtc ata gaa act cac atg aga caa atg       528
Tyr Ser Ser Arg Asp Pro Ser Val Ile Glu Thr His Met Arg Gln Met
                165                 170                 175 cgc tca gct tca att ggt gta cta gcc ctc tct tgg tac cca cct gat       576
Arg Ser Ala Ser Ile Gly Val Leu Ala Leu Ser Trp Tyr Pro Pro Asp
            180                 185                 190 gta aat gat gaa aat gga gaa cct act gat aac ttg gta ccc act att       624
Val Asn Asp Glu Asn Gly Glu Pro Thr Asp Asn Leu Val Pro Thr Ile
        195                 200                 205 ttg gat aaa gct cat aaa tat aac cta aag gtt act ttt cac ata gaa       672
Leu Asp Lys Ala His Lys Tyr Asn Leu Lys Val Thr Phe His Ile Glu
    210                 215                 220 cca tat agc aat cga gat gat caa aac atg tac aaa aat gtc aag tat       720
Pro Tyr Ser Asn Arg Asp Asp Gln Asn Met Tyr Lys Asn Val Lys Tyr
225                 230                 235                 240 att ata gac aaa tat gga aat cat ccg gcc ttt tac agg tac aag acg       768
Ile Ile Asp Lys Tyr Gly Asn His Pro Ala Phe Tyr Arg Tyr Lys Thr
                245                 250                 255 aag act ggc aat gct ctt cct atg ttt tat gtc tat gat tcc tat att       816
Lys Thr Gly Asn Ala Leu Pro Met Phe Tyr Val Tyr Asp Ser Tyr Ile
            260                 265                 270 acc aag cct gaa aaa tgg gcc aat ctg tta acc acc tca ggg tct cgg       864
Thr Lys Pro Glu Lys Trp Ala Asn Leu Leu Thr Thr Ser Gly Ser Arg
        275                 280                 285 agt att cgc aat tct cct tat gat gga ctg ttt att gcc ctt ctg gta       912
Ser Ile Arg Asn Ser Pro Tyr Asp Gly Leu Phe Ile Ala Leu Leu Val
    290                 295                 300 gaa gaa aaa cat aag tat gat att ctt caa agt ggt ttt gat gga att       960
Glu Glu Lys His Lys Tyr Asp Ile Leu Gln Ser Gly Phe Asp Gly Ile
```

```
                       305                  310                  315                  320
tac aca tat ttt gcc aca aat ggc ttt act tat ggc tca tca cat cag    1008
Tyr Thr Tyr Phe Ala Thr Asn Gly Phe Thr Tyr Gly Ser Ser His Gln
                325                  330                  335 aat tgg gct agc cta aaa tta att tgt gat aaa tac aac tta ata ttt    1056
Asn Trp Ala Ser Leu Lys Leu Ile Cys Asp Lys Tyr Asn Leu Ile Phe
                340                  345                  350 atc cca agt gtg ggc cca gga tac ata gat acc agc atc cgt cca tgg    1104
Ile Pro Ser Val Gly Pro Gly Tyr Ile Asp Thr Ser Ile Arg Pro Trp
                355                  360                  365 aac acg caa aac act cgg aac cga atc aat ggg aag tat tat gaa att    1152
Asn Thr Gln Asn Thr Arg Asn Arg Ile Asn Gly Lys Tyr Tyr Glu Ile
                370                  375                  380 ggt ctg agt gcc gca ctt cag aca cgc ccc agc tta att tct atc acc    1200
Gly Leu Ser Ala Ala Leu Gln Thr Arg Pro Ser Leu Ile Ser Ile Thr
385                  390                  395                  400 tct ttt aat gag tgg cat gaa gga act cag att gaa aaa gct gtt ccc    1248
Ser Phe Asn Glu Trp His Glu Gly Thr Gln Ile Glu Lys Ala Val Pro
                405                  410                  415 aaa aga acc agt aat aca gtg tac cta gat tac cgt cct cat aaa cca    1296
Lys Arg Thr Ser Asn Thr Val Tyr Leu Asp Tyr Arg Pro His Lys Pro
                420                  425                  430 ggt ctt tac cta gaa ctg act cgc aag tgg tct gaa aaa tac agt aag    1344
Gly Leu Tyr Leu Glu Leu Thr Arg Lys Trp Ser Glu Lys Tyr Ser Lys
                435                  440                  445 gaa aga gca act tat gca tta gat cgc cag ctg cct gtt tct taa        1389
Glu Arg Ala Thr Tyr Ala Leu Asp Arg Gln Leu Pro Val Ser
                450                  455                  460

<210> SEQ ID NO 2
<211> LENGTH: 462
<212> TYPE: PRT
<213> ORGANISM: Homo sapiens

<400> SEQUENCE: 2

Met Ala Lys Phe Arg Arg Arg Thr Cys Ile Ile Leu Ala Leu Phe Ile
 1               5                  10                  15

Leu Phe Ile Phe Ser Leu Met Met Gly Leu Lys Met Leu Arg Pro Asn
                20                  25                  30

Thr Ala Thr Phe Gly Ala Pro Phe Gly Leu Asp Leu Leu Pro Glu Leu
            35                  40                  45

His Gln Arg Thr Ile His Leu Gly Lys Asn Phe Asp Phe Gln Lys Ser
         50                  55                  60

Asp Arg Ile Asn Ser Glu Thr Asn Thr Lys Asn Leu Lys Ser Val Glu
65                  70                  75                  80

Ile Thr Met Lys Pro Ser Lys Ala Ser Glu Leu Asn Leu Asp Glu Leu
                85                  90                  95

Pro Pro Leu Asn Asn Tyr Leu His Val Phe Tyr Ser Trp Tyr Gly Tyr
                100                 105                 110

Asn Pro Gln Phe Asp Gly Lys Tyr Ile His Trp Asn His Pro Val Leu
            115                 120                 125

Glu His Trp Asp Pro Arg Ile Ala Lys Asn Tyr Pro Gln Gly Arg His
        130                 135                 140

Asn Pro Pro Asp Asp Ile Gly Ser Ser Phe Tyr Pro Glu Leu Gly Ser
145                 150                 155                 160

Tyr Ser Ser Arg Asp Pro Ser Val Ile Glu Thr His Met Arg Gln Met
                165                 170                 175
```

```
Arg Ser Ala Ser Ile Gly Val Leu Ala Leu Ser Trp Tyr Pro Pro Asp
            180                 185                 190

Val Asn Asp Glu Asn Gly Glu Pro Thr Asp Asn Leu Val Pro Thr Ile
        195                 200                 205

Leu Asp Lys Ala His Lys Tyr Asn Leu Lys Val Thr Phe His Ile Glu
    210                 215                 220

Pro Tyr Ser Asn Arg Asp Asp Gln Asn Met Tyr Lys Asn Val Lys Tyr
225                 230                 235                 240

Ile Ile Asp Lys Tyr Gly Asn His Pro Ala Phe Tyr Arg Tyr Lys Thr
                245                 250                 255

Lys Thr Gly Asn Ala Leu Pro Met Phe Tyr Val Tyr Asp Ser Tyr Ile
            260                 265                 270

Thr Lys Pro Glu Lys Trp Ala Asn Leu Leu Thr Thr Ser Gly Ser Arg
        275                 280                 285

Ser Ile Arg Asn Ser Pro Tyr Asp Gly Leu Phe Ile Ala Leu Leu Val
    290                 295                 300

Glu Glu Lys His Lys Tyr Asp Ile Leu Gln Ser Gly Phe Asp Gly Ile
305                 310                 315                 320

Tyr Thr Tyr Phe Ala Thr Asn Gly Phe Thr Tyr Gly Ser Ser His Gln
                325                 330                 335

Asn Trp Ala Ser Leu Lys Leu Ile Cys Asp Lys Tyr Asn Leu Ile Phe
            340                 345                 350

Ile Pro Ser Val Gly Pro Gly Tyr Ile Asp Thr Ser Ile Arg Pro Trp
        355                 360                 365

Asn Thr Gln Asn Thr Arg Asn Arg Ile Asn Gly Lys Tyr Tyr Glu Ile
    370                 375                 380

Gly Leu Ser Ala Ala Leu Gln Thr Arg Pro Ser Leu Ile Ser Ile Thr
385                 390                 395                 400

Ser Phe Asn Glu Trp His Glu Gly Thr Gln Ile Glu Lys Ala Val Pro
                405                 410                 415

Lys Arg Thr Ser Asn Thr Val Tyr Leu Asp Tyr Arg Pro His Lys Pro
            420                 425                 430

Gly Leu Tyr Leu Glu Leu Thr Arg Lys Trp Ser Glu Lys Tyr Ser Lys
        435                 440                 445

Glu Arg Ala Thr Tyr Ala Leu Asp Arg Gln Leu Pro Val Ser
    450                 455                 460

<210> SEQ ID NO 3
<211> LENGTH: 1389
<212> TYPE: DNA
<213> ORGANISM: Mus musculus
<220> FEATURE:
<221> NAME/KEY: CDS
<222> LOCATION: (1)..(1386)

<400> SEQUENCE: 3 atg gca aaa ttt cga aga agg acc tgc atc ctt ttg tca ctt ttt att    48
Met Ala Lys Phe Arg Arg Arg Thr Cys Ile Leu Leu Ser Leu Phe Ile
  1               5                  10                  15 cta ttt att ttt tct ctg atg atg ggc tta aag atg ctg tgg cca aac    96
Leu Phe Ile Phe Ser Leu Met Met Gly Leu Lys Met Leu Trp Pro Asn
             20                  25                  30 gca gca tcc ttt gga cct cct ttt gga ctt gac ctc ctt cca gaa ctt   144
Ala Ala Ser Phe Gly Pro Pro Phe Gly Leu Asp Leu Leu Pro Glu Leu
         35                  40                  45 cat cca cta aat gcg cat tcg gga aac aaa gct gac ttc caa agg agt   192
His Pro Leu Asn Ala His Ser Gly Asn Lys Ala Asp Phe Gln Arg Ser
```

-continued

```
                50                      55                      60
gat aga atc aac atg gaa aca aac acc aag gct tta aaa ggc gct ggc        240
Asp Arg Ile Asn Met Glu Thr Asn Thr Lys Ala Leu Lys Gly Ala Gly
 65                  70                  75                  80 atg act gtg ctg cca gcc aaa gcc tct gag gtg aac ctg gaa gaa cta        288
Met Thr Val Leu Pro Ala Lys Ala Ser Glu Val Asn Leu Glu Glu Leu
                 85                  90                  95 cct cct ctg aat tac ttt tta cat gca ttt tat tac agt tgg tat gga        336
Pro Pro Leu Asn Tyr Phe Leu His Ala Phe Tyr Tyr Ser Trp Tyr Gly
            100                 105                 110 aat cca cag ttt gat ggt aaa tat ata cac tgg aat cat ccg gtc ctg        384
Asn Pro Gln Phe Asp Gly Lys Tyr Ile His Trp Asn His Pro Val Leu
        115                 120                 125 gaa cac tgg gac cct cgg ata gcc aag aac tat cca caa gga caa cat        432
Glu His Trp Asp Pro Arg Ile Ala Lys Asn Tyr Pro Gln Gly Gln His
    130                 135                 140 agt cct cca gac gac att ggc tcc agt ttt tat cct gag tta gga agt        480
Ser Pro Pro Asp Asp Ile Gly Ser Ser Phe Tyr Pro Glu Leu Gly Ser
145                 150                 155                 160 tac agc tct cga gac cct tct gtc ata gaa act cac atg aaa caa atg        528
Tyr Ser Ser Arg Asp Pro Ser Val Ile Glu Thr His Met Lys Gln Met
                165                 170                 175 cgc tca gcc tca att gga gtt ctg gcc ctg tct tgg tac cca cct gat        576
Arg Ser Ala Ser Ile Gly Val Leu Ala Leu Ser Trp Tyr Pro Pro Asp
            180                 185                 190 tca agg gat gac aat ggc gaa gct act gat cac ttg gtg cca acc att        624
Ser Arg Asp Asp Asn Gly Glu Ala Thr Asp His Leu Val Pro Thr Ile
        195                 200                 205 ttg gat aaa gct cat aaa tat aat ctg aag gtc act ttt cac ata gag        672
Leu Asp Lys Ala His Lys Tyr Asn Leu Lys Val Thr Phe His Ile Glu
    210                 215                 220 cca tat agc aat cga gat gat caa aac atg cat caa aat atc aag tat        720
Pro Tyr Ser Asn Arg Asp Asp Gln Asn Met His Gln Asn Ile Lys Tyr
225                 230                 235                 240 att ata gac aaa tat gga aac cat cca gcc ttt tat aga tac aag acc        768
Ile Ile Asp Lys Tyr Gly Asn His Pro Ala Phe Tyr Arg Tyr Lys Thr
                245                 250                 255 agg act ggg cat tct ctg ccc atg ttt tat gtc tat gat tct tac atc        816
Arg Thr Gly His Ser Leu Pro Met Phe Tyr Val Tyr Asp Ser Tyr Ile
            260                 265                 270 aca aag cct aca ata tgg gcc aat ctg tta aca ccc tcc gga tct cag        864
Thr Lys Pro Thr Ile Trp Ala Asn Leu Leu Thr Pro Ser Gly Ser Gln
        275                 280                 285 agt gtt cgc agt tct ctt tat gat gga ttg ttt att gca ctt cta gta        912
Ser Val Arg Ser Ser Leu Tyr Asp Gly Leu Phe Ile Ala Leu Leu Val
    290                 295                 300 gaa gaa aag cat aaa aat gat att ctt cag agt ggt ttt gat ggt att        960
Glu Glu Lys His Lys Asn Asp Ile Leu Gln Ser Gly Phe Asp Gly Ile
305                 310                 315                 320 tac aca tat ttt gcc aca aat ggc ttt aca tat ggc tca tct cat cag       1008
Tyr Thr Tyr Phe Ala Thr Asn Gly Phe Thr Tyr Gly Ser Ser His Gln
                325                 330                 335 aat tgg aat aac ctg aaa tcc ttt tgt gaa aag aac aac ttg atg ttt       1056
Asn Trp Asn Asn Leu Lys Ser Phe Cys Glu Lys Asn Asn Leu Met Phe
            340                 345                 350 atc cca agt gta ggc cca gga tac ata gat aca agc atc cga cca tgg       1104
Ile Pro Ser Val Gly Pro Gly Tyr Ile Asp Thr Ser Ile Arg Pro Trp
        355                 360                 365 aac act cag aac acc cgg aac aga gtc aat ggg aag tat tat gaa gtt       1152
```

```
                                           -continued

Asn Thr Gln Asn Thr Arg Asn Arg Val Asn Gly Lys Tyr Tyr Glu Val
    370                 375                 380 ggt cta agt gct gca ctc cag acc cac ccc agt tta att tcc atc acc   1200
Gly Leu Ser Ala Ala Leu Gln Thr His Pro Ser Leu Ile Ser Ile Thr
385                 390                 395                 400 tct ttc aat gag tgg cat gaa gga act caa att gaa aag gct gtc ccc   1248
Ser Phe Asn Glu Trp His Glu Gly Thr Gln Ile Glu Lys Ala Val Pro
                405                 410                 415 aaa aga act gct aac acg ata tac ctg gat tac cgg cct cat aag cca   1296
Lys Arg Thr Ala Asn Thr Ile Tyr Leu Asp Tyr Arg Pro His Lys Pro
            420                 425                 430 agt ctt tat cta gaa cta act cga aag tgg tct gaa aaa ttc agt aag   1344
Ser Leu Tyr Leu Glu Leu Thr Arg Lys Trp Ser Glu Lys Phe Ser Lys
        435                 440                 445 gaa aga atg acg tat gca ttg gat caa cag cag cct gct tca taa       1389
Glu Arg Met Thr Tyr Ala Leu Asp Gln Gln Gln Pro Ala Ser
    450                 455                 460

<210> SEQ ID NO 4
<211> LENGTH: 462
<212> TYPE: PRT
<213> ORGANISM: Mus musculus

<400> SEQUENCE: 4

Met Ala Lys Phe Arg Arg Thr Cys Ile Leu Leu Ser Leu Phe Ile
1               5                   10                  15

Leu Phe Ile Phe Ser Leu Met Met Gly Leu Lys Met Leu Trp Pro Asn
                20                  25                  30

Ala Ala Ser Phe Gly Pro Pro Phe Gly Leu Asp Leu Leu Pro Glu Leu
            35                  40                  45

His Pro Leu Asn Ala His Ser Gly Asn Lys Ala Asp Phe Gln Arg Ser
        50                  55                  60

Asp Arg Ile Asn Met Glu Thr Asn Thr Lys Ala Leu Lys Gly Ala Gly
65                  70                  75                  80

Met Thr Val Leu Pro Ala Lys Ala Ser Glu Val Asn Leu Glu Glu Leu
                85                  90                  95

Pro Pro Leu Asn Tyr Phe Leu His Ala Phe Tyr Tyr Ser Trp Tyr Gly
                100                 105                 110

Asn Pro Gln Phe Asp Gly Lys Tyr Ile His Trp Asn His Pro Val Leu
            115                 120                 125

Glu His Trp Asp Pro Arg Ile Ala Lys Asn Tyr Pro Gln Gly Gln His
        130                 135                 140

Ser Pro Pro Asp Asp Ile Gly Ser Ser Phe Tyr Pro Glu Leu Gly Ser
145                 150                 155                 160

Tyr Ser Ser Arg Asp Pro Ser Val Ile Glu Thr His Met Lys Gln Met
                165                 170                 175

Arg Ser Ala Ser Ile Gly Val Leu Ala Leu Ser Trp Tyr Pro Pro Asp
            180                 185                 190

Ser Arg Asp Asp Asn Gly Glu Ala Thr Asp His Leu Val Pro Thr Ile
        195                 200                 205

Leu Asp Lys Ala His Lys Tyr Asn Leu Lys Val Thr Phe His Ile Glu
    210                 215                 220

Pro Tyr Ser Asn Arg Asp Asp Gln Asn Met His Gln Asn Ile Lys Tyr
225                 230                 235                 240

Ile Ile Asp Lys Tyr Gly Asn His Pro Ala Phe Tyr Arg Tyr Lys Thr
                245                 250                 255
```

```
Arg Thr Gly His Ser Leu Pro Met Phe Tyr Val Tyr Asp Ser Tyr Ile
            260                 265                 270

Thr Lys Pro Thr Ile Trp Ala Asn Leu Leu Thr Pro Ser Gly Ser Gln
        275                 280                 285

Ser Val Arg Ser Ser Leu Tyr Asp Gly Leu Phe Ile Ala Leu Leu Val
    290                 295                 300

Glu Glu Lys His Lys Asn Asp Ile Leu Gln Ser Gly Phe Asp Gly Ile
305                 310                 315                 320

Tyr Thr Tyr Phe Ala Thr Asn Gly Phe Thr Tyr Gly Ser Ser His Gln
                325                 330                 335

Asn Trp Asn Asn Leu Lys Ser Phe Cys Glu Lys Asn Asn Leu Met Phe
            340                 345                 350

Ile Pro Ser Val Gly Pro Gly Tyr Ile Asp Thr Ser Ile Arg Pro Trp
        355                 360                 365

Asn Thr Gln Asn Thr Arg Asn Arg Val Asn Gly Lys Tyr Tyr Glu Val
    370                 375                 380

Gly Leu Ser Ala Ala Leu Gln Thr His Pro Ser Leu Ile Ser Ile Thr
385                 390                 395                 400

Ser Phe Asn Glu Trp His Glu Gly Thr Gln Ile Glu Lys Ala Val Pro
                405                 410                 415

Lys Arg Thr Ala Asn Thr Ile Tyr Leu Asp Tyr Arg Pro His Lys Pro
            420                 425                 430

Ser Leu Tyr Leu Glu Leu Thr Arg Lys Trp Ser Glu Lys Phe Ser Lys
        435                 440                 445

Glu Arg Met Thr Tyr Ala Leu Asp Gln Gln Gln Pro Ala Ser
    450                 455                 460

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgtgttagc ggccgccacc atggcaatca aaccaagaac gaagggcaaa acgtactcc      59

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggcgcgcccg cccctaacgg tcatttgttt taacacaggc                           40

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctaccaatgc ggccgccacc atgggcatgt tttttaattt aaggtcaaat ataagaag       59
```

```
<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggcgcgcccc gacctaccat tttgcgtgga tacaccaatg                          40

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acggttcagc ggccgccacc atgcttattt caaaatctag aatgtttaaa acattttgg    59

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcgcgcccg aattcttgta gtttactaat atcaacggtg gc                      42

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaattcgcca ccatggattt ccaaaagagt gacagaatca acag                    44

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaattcccag aaacaggcag ctggcgatc                                     29

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggcaaagt ttcggagaag gacttgc                                       27

<210> SEQ ID NO 14
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttaagaaaca ggcagctggc gatctaatgc                                        30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atggcaaaat tcgaagaag gacctgcatc                                         30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttatgaagca ggctgctgtt gatccaatgc                                        30

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaattcgcca ccatggactt ccaaaggagt gatcgaatcg acatgg                      46

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaattccctg aagcaggcag ctgttgatcc                                        30

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aatttatgga ctacaaggat gacgacgaca agg                                    33

<210> SEQ ID NO 20
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aattccttgt cgtcgtcatc cttgtagtcc ata                                     33

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcgcgccga cttccaaagg agtgatcgaa tcgacatgg                               39

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccttaattaa ttatgaagca ggcagctgtt gatccaatgc                              40

<210> SEQ ID NO 23
<211> LENGTH: 290
<212> TYPE: PRT
<213> ORGANISM: Rattus norvegicus

<400> SEQUENCE: 23

Met Lys Gln Met Arg Ser Ala Ser Ile Gly Val Leu Ala Leu Ser Trp
  1               5                  10                  15

Tyr Pro Pro Asp Ala Ser Asp Glu Asn Gly Glu Ala Thr Asp Tyr Leu
                 20                  25                  30

Val Pro Thr Ile Leu Asp Lys Ala His Lys Tyr Asn Leu Lys Val Thr
             35                  40                  45

Phe His Ile Glu Pro Tyr Ser Asn Arg Asp Asp Gln Asn Met His Gln
         50                  55                  60

Asn Val Lys Tyr Ile Ile Asp Lys Tyr Gly Asn His Pro Ala Phe Tyr
 65                  70                  75                  80

Arg Tyr Lys Thr Arg Met Gly His Ser Leu Pro Met Phe Tyr Ile Tyr
                 85                  90                  95

Asp Ser Tyr Ile Thr Lys Pro Lys Thr Trp Ala Asn Leu Leu Thr Pro
            100                 105                 110

Ser Gly Ser Gln Ser Val Arg Gly Ser Pro Tyr Asp Gly Leu Phe Ile
        115                 120                 125

Ala Leu Leu Val Glu Glu Lys His Lys Tyr Asp Ile Leu Gln Ser Gly
    130                 135                 140

Phe Asp Gly Ile Tyr Thr Tyr Phe Ala Thr Asn Gly Phe Thr Tyr Gly
145                 150                 155                 160

Ser Ser His Gln Asn Trp Asn Lys Leu Lys Ser Phe Cys Glu Lys Asn
                165                 170                 175

Asn Met Ile Phe Ile Pro Ser Val Gly Pro Gly Tyr Ile Asp Thr Ser
            180                 185                 190
```

```
Ile Arg Pro Trp Asn Thr Gln Asn Thr Arg Asn Arg Ile Asn Gly Lys
            195                 200                 205

Tyr Tyr Glu Val Gly Leu Ser Ala Ala Leu Gln Thr Gln Pro Ser Leu
    210                 215                 220

Ile Ser Ile Thr Ser Phe Asn Glu Trp His Glu Gly Thr Gln Ile Glu
225                 230                 235                 240

Lys Ala Val Pro Lys Arg Thr Ala Asn Thr Val Tyr Leu Asp Tyr Arg
                245                 250                 255

Pro His Lys Pro Ser Leu Tyr Leu Glu Ile Thr Arg Lys Trp Ser Glu
            260                 265                 270

Lys Tyr Ser Lys Glu Arg Met Thr Tyr Ala Leu Asp Gln Gln Leu Pro
    275                 280                 285

Ala Ser
    290

<210> SEQ ID NO 24
<211> LENGTH: 290
<212> TYPE: PRT
<213> ORGANISM: Homo sapiens

<400> SEQUENCE: 24

Met Arg Gln Met Arg Ser Ala Ser Ile Gly Val Leu Ala Leu Ser Trp
1               5                   10                  15

Tyr Pro Pro Asp Val Asn Asp Glu Asn Gly Pro Thr Asp Asn Leu
            20                  25                  30

Val Pro Thr Ile Leu Asp Lys Ala His Lys Tyr Asn Leu Lys Val Thr
        35                  40                  45

Phe His Ile Glu Pro Tyr Ser Asn Arg Asp Asp Gln Asn Met Tyr Lys
    50                  55                  60

Asn Val Lys Tyr Ile Ile Asp Lys Tyr Gly Asn His Pro Ala Phe Tyr
65                  70                  75                  80

Arg Tyr Lys Thr Lys Thr Gly Asn Ala Leu Pro Met Phe Tyr Val Tyr
                85                  90                  95

Asp Ser Tyr Ile Thr Lys Pro Glu Lys Trp Ala Asn Leu Leu Thr Thr
            100                 105                 110

Ser Gly Ser Arg Ser Ile Arg Asn Ser Pro Tyr Asp Gly Leu Phe Ile
        115                 120                 125

Ala Leu Leu Val Glu Glu Lys His Lys Tyr Asp Ile Leu Gln Ser Gly
    130                 135                 140

Phe Asp Gly Ile Tyr Thr Tyr Phe Ala Thr Asn Gly Phe Thr Tyr Gly
145                 150                 155                 160

Ser Ser His Gln Asn Trp Ala Ser Leu Lys Leu Phe Cys Asp Lys Tyr
                165                 170                 175

Asn Leu Ile Phe Ile Pro Ser Val Gly Pro Gly Tyr Ile Asp Thr Ser
            180                 185                 190

Ile Arg Pro Trp Asn Thr Gln Asn Thr Arg Asn Arg Ile Asn Gly Lys
        195                 200                 205

Tyr Tyr Glu Ile Gly Leu Ser Ala Ala Leu Gln Thr Arg Pro Ser Leu
    210                 215                 220

Ile Ser Ile Thr Ser Phe Asn Glu Trp His Glu Gly Thr Gln Ile Glu
225                 230                 235                 240

Lys Ala Val Pro Lys Arg Thr Ser Asn Thr Val Tyr Leu Asp Tyr Arg
                245                 250                 255

Pro His Lys Pro Gly Leu Tyr Leu Glu Leu Thr Arg Lys Trp Ser Glu
```

```
                    260                 265                 270
Lys Tyr Ser Lys Glu Arg Ala Thr Tyr Ala Leu Asp Arg Gln Leu Pro
                275                 280                 285

Val Ser
    290

<210> SEQ ID NO 25
<211> LENGTH: 195
<212> TYPE: PRT
<213> ORGANISM: Homo sapiens

<400> SEQUENCE: 25

Met Ala Lys Phe Arg Arg Thr Cys Ile Ile Leu Ala Leu Phe Ile
  1               5                  10                  15

Leu Phe Ile Phe Ser Leu Met Met Gly Leu Lys Met Leu Arg Pro Asn
                 20                  25                  30

Thr Ala Thr Phe Gly Ala Pro Phe Gly Leu Asp Leu Leu Pro Glu Leu
             35                  40                  45

His Gln Arg Thr Ile His Leu Gly Lys Asn Phe Asp Phe Gln Lys Ser
         50                  55                  60

Asp Arg Ile Asn Ser Glu Thr Asn Thr Lys Asn Leu Lys Ser Val Glu
 65                  70                  75                  80

Ile Thr Met Lys Pro Ser Lys Ala Ser Glu Leu Asn Leu Asp Glu Leu
                 85                  90                  95

Pro Pro Leu Asn Asn Tyr Leu His Val Phe Tyr Tyr Ser Trp Tyr Gly
            100                 105                 110

Asn Pro Gln Phe Asp Gly Lys Tyr Ile His Trp Asn His Pro Val Leu
        115                 120                 125

Glu His Trp Asp Pro Arg Ile Ala Lys Asn Tyr Pro Gln Gly Arg His
    130                 135                 140

Asn Pro Pro Asp Asp Ile Gly Ser Ser Phe Tyr Pro Glu Leu Gly Ser
145                 150                 155                 160

Tyr Ser Ser Arg Asp Pro Ser Val Ile Glu Thr His Met Arg Gln Met
                165                 170                 175

Arg Ser Ala Ser Ile Gly Val Leu Ala Leu Ser Trp Tyr Pro Pro Asp
            180                 185                 190

Val Asn Glu
        195

<210> SEQ ID NO 26
<211> LENGTH: 451
<212> TYPE: PRT
<213> ORGANISM: Rattus norvegicus

<400> SEQUENCE: 26

Met Gly Ala Leu Met Ala Thr Tyr Ser Glu Gly Met Met Gly Cys Ser
  1               5                  10                  15

Ser Val Gly Arg Cys Phe Ser Ser Thr Leu Ser Pro Ile Ile Thr Leu
                 20                  25                  30

Val Ala Thr Ser Met Lys Ser Thr Pro Arg Val Leu Glu Asn Lys Ala
             35                  40                  45

Asp Phe Gln Arg Ser Asp Arg Ile Asp Met Glu Thr Asn Thr Lys Asp
         50                  55                  60

Leu Lys Gly Ala Gly Val Thr Val His Pro Pro Arg Ala Ser Glu Val
 65                  70                  75                  80

Asn Leu Glu Glu Leu Pro Pro Leu Asn Tyr Phe Val His Ala Phe Tyr
```

```
                85                  90                  95
Tyr Ser Trp Tyr Gly Asn Pro Gln Phe Asp Gly Lys Tyr Val His Trp
            100                 105                 110
Asn His Pro Val Leu Glu His Trp Asp Pro Arg Ile Ala Lys Asn Tyr
        115                 120                 125
Pro Gln Gly Arg His Ser Pro Asp Asp Ile Gly Ser Ser Phe Tyr
    130                 135                 140
Pro Glu Leu Gly Ser Tyr Ser Ser Arg Asp Pro Ser Val Ile Glu Thr
145                 150                 155                 160
His Met Lys Gln Met Arg Ser Ala Ser Ile Gly Val Leu Ala Leu Ser
                165                 170                 175
Trp Tyr Pro Pro Asp Ala Ser Asp Glu Asn Gly Glu Ala Thr Asp Tyr
            180                 185                 190
Leu Val Pro Thr Ile Leu Asp Lys Ala His Lys Tyr Asn Leu Lys Val
        195                 200                 205
Thr Phe His Ile Glu Pro Tyr Ser Asn Arg Asp Asp Gln Asn Met His
    210                 215                 220
Gln Asn Val Lys Tyr Ile Ile Asp Lys Tyr Gly Asn His Pro Ala Phe
225                 230                 235                 240
Tyr Arg Tyr Lys Thr Arg Met Gly His Ser Leu Pro Met Phe Tyr Ile
                245                 250                 255
Tyr Asp Ser Tyr Ile Thr Lys Pro Lys Thr Trp Ala Asn Leu Leu Thr
            260                 265                 270
Pro Ser Gly Ser Gln Ser Val Arg Gly Ser Pro Tyr Asp Gly Leu Phe
        275                 280                 285
Ile Ala Leu Leu Val Glu Glu Lys His Lys Tyr Asp Ile Leu Gln Ser
    290                 295                 300
Gly Phe Asp Gly Ile Tyr Thr Tyr Phe Ala Thr Asn Gly Phe Thr Tyr
305                 310                 315                 320
Gly Ser Ser His Gln Asn Trp Asn Lys Leu Lys Ser Phe Cys Glu Lys
                325                 330                 335
Asn Asn Met Ile Phe Ile Pro Ser Val Gly Pro Gly Tyr Ile Asp Thr
            340                 345                 350
Ser Ile Arg Pro Trp Asn Thr Gln Asn Thr Arg Asn Arg Ile Asn Gly
        355                 360                 365
Lys Tyr Tyr Glu Val Gly Leu Ser Ala Ala Leu Gln Thr Gln Pro Ser
    370                 375                 380
Leu Ile Ser Ile Thr Ser Phe Asn Glu Trp His Glu Gly Thr Gln Ile
385                 390                 395                 400
Glu Lys Ala Val Pro Lys Arg Thr Ala Asn Thr Val Tyr Leu Asp Tyr
                405                 410                 415
Arg Pro His Lys Pro Ser Leu Tyr Leu Glu Ile Thr Arg Lys Trp Ser
            420                 425                 430
Glu Lys Tyr Ser Lys Glu Arg Met Thr Tyr Ala Leu Asp Gln Gln Leu
        435                 440                 445
Pro Ala Ser
    450

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide motif
```

-continued

```
<220> FEATURE:
<221> NAME/KEY: MOD_RES
<222> LOCATION: (4)
<223> OTHER INFORMATION: Lys or Arg

<400> SEQUENCE: 27

Asp Phe Gln Xaa Ser Asp Arg Ile Asn
 1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Asp Glu Leu
 1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Asp Glu Leu
 1
```

ENDOMANNOSIDASES IN THE MODIFICATION OF GLYCOPROTEINS IN EUKARYOTES

CROSS REFERENCE TO RELATED APPLICATIONS

This application is a continuation of U.S. application Ser. No. 12/009,105, filed Jan. 16, 2008, now abandoned, which is a continuation of U.S. application Ser. No. 10/695,243, filed Oct. 27, 2003, now U.S. Pat. No. 7,332,299, which is a continuation-in-part of U.S. application Ser. No. 10/371,877, filed on Feb. 20, 2003, now U.S. Pat. No. 7,449,308.

FIELD OF THE INVENTION

The present invention generally relates to methods of modifying the glycosylation structures of recombinant proteins expressed in fungi or other lower eukaryotes, to more closely resemble the glycosylation of proteins from higher mammals, in particular humans. The present invention also relates to novel enzymes and, nucleic acids encoding them and, hosts engineered to express the enzymes, methods for producing modified glycoproteins in hosts and modified glycoproteins so produced.

BACKGROUND OF THE INVENTION

After DNA is transcribed and translated into a protein, further post-translational processing involves the attachment of sugar residues, a process known as glycosylation. Different organisms produce different glycosylation enzymes (glycosyltransferases and glycosidases) and have different substrates (nucleotide sugars) available, so that the glycosylation patterns as well as composition of the individual oligosaccharides, even of one and the same protein, will be different depending on the host system in which the particular protein is being expressed. Bacteria typically do not glycosylate proteins and if so only in a very unspecific manner (Moens and Vanderleyden, *Arch. Microbiol.* 168(3):169-175 (1997)). Lower eukaryotes such as filamentous fungi and yeast add primarily mannose and mannosylphosphate sugars, whereas insect cells such as Sf9 cells glycosylate proteins in yet another way. See R. K. Bretthauer et al., *Biotechnology and Applied Biochemistry* 1999 30:193-200 (1999); W. Martinet, et al., *Biotechnology Letters* 1998 20:1171-1177 (1998); S. Weikert, et al., *Nature Biotechnology* 1999 17: 1116-1121 (1999); M. Malissard, et al., *Biochem. Biophys. Res. Comm.* 2000 267:169-173 (2000); D. Jarvis, et al., *Curr. Op. Biotech.* 1998 9:528-533 (1998); and Takeuchi, *Trends in Glycoscience and Glycotechnology* 1997 9:S29-S35 (1997).

N-linked glycosylation plays a major role in the processing of many cellular and secreted proteins. In eukaryotes, the preassembled oligosaccharide Glc3Man9GlcNAc2 is transferred from dolichol onto the acceptor site of the protein by oligosaccharyltransferase in the endoplasmic reticulum (Dempski and Imperiali, Curr. Opin. Chem. Biol. 6: 844-850 (2002)). Subsequently, the terminal a-1,2-glucose is removed by glucosidase I facilitating the removal of the remaining two a-1,3-glucose residues by glucosidase II (Herscovics, Biochim. Biophys. Acta 1473: 96-107 (1999)). The high mannose glycan remaining is processed by the ER mannosidase, to Man8GlcNAc2, prior to translocation of the glycoprotein to the Golgi, where the glycan structure is further modified. Incorrect processing of the glycan structure in the ER, in turn, can prevent subsequent modification, leading to a disease state. The absence of glucosidase I results in congenital disorder of glycosylation type (CDG) IIb which is extremely rare, with only one reported human case, and leads to early death (Marquardt and Denecke, *Eur. J. Pediatr.* 162: 359-379 (2003)). Isolation of the Chinese hamster ovary cell line Lec23, deficient in glucosidase I, demonstrated that the predominant glycoform present is Glc3Man9GlcNAc2 (Ray et al., *J. Biol. Chem.* 266: 22818-22825 (1991)). The initial stages of glycosylation in yeast and mammals are identical with the same glycan structures emerging from the endoplasmic reticulum. However, when these glycans are processed by the Golgi, the resultant structures are drastically different, thus resulting in yeast glycosylation patterns that differ substantially from those found in higher eukaryotes, such as humans and other mammals (R. Bretthauer, et al., *Biotechnology and Applied Biochemistry* 30:193-200 (1999)). Moreover, the vastly different glycosylation pattern has, in some cases, been shown to increase the immunogenicity of these proteins in humans and reduce their half-life (Takeuchi (1997) supra).

The early steps of human glycosylation can be divided into at least two different phases: (i) lipid-linked Glc3Man9GlcNAc2 oligosaccharides assembled by a sequential set of reactions at the membrane of the endoplasmatic reticulum (ER); and (ii) the transfer of this oligosaccharide from the lipid anchor dolichyl pyrophosphate on to de novo synthesized protein. The site of the specific transfer is defined by an Asparagine residue in the sequence Asn-Xaa-Ser/Thr, where Xaa can be any amino acid except Proline (Y. Gavel et al., *Protein Engineering* 3:433-442 (1990)).

Further processing by glucosidases and mannosidases occurs in the ER before the nascent glycoprotein is transferred to the early Golgi apparatus, where additional mannose residues are removed by Golgi specific a-1,2-mannosidases. Processing continues as the protein proceeds through the Golgi. In the medial Golgi, a number of modifying enzymes, including N-acetylglucosaminyl-transferases (GnT I, GnT II, GnT III, GnT IV GnT V GnT VI), mannosidase II, and fucosyltransferases, add and remove specific sugar residues. Finally, in the trans-Golgi, galactosyltranferases and sialyltransferases produce a structure that is released from the Golgi. The glycans characterized as bi-, tri- and tetra-antennary structures containing galactose, fucose, N-acetylglucosamine and a high degree of terminal sialic acid give glycoproteins their human characteristics.

When proteins are isolated from humans or animals, a significant number of them are post-translationally modified, with glycosylation being one of the most significant modifications. Several studies have shown that glycosylation plays an important role in determining the (1) immunogenicity, (2) pharmacokinetic properties, (3) trafficking, and (4) efficacy of therapeutic proteins. An estimated 70% of all therapeutic proteins are glycosylated and thus currently rely on a production system (i.e., host) that is able to glycosylate in a manner similar to humans. To date, most glycoproteins are made in a mammalian host system. It is thus not surprising that substantial efforts by the pharmaceutical industry have been directed at developing processes to obtain glycoproteins that are as "humanoid" as possible. This may involve the genetic engineering of such mammalian cells to enhance the degree of sialylation (i.e., terminal addition of sialic acid) of proteins expressed by the cells, which is known to improve pharmacokinetic properties of such proteins. Alternatively, one may improve the degree of sialylation by in vitro addition of such sugars by using known glycosyltransferases and their respective nucleotide sugar substrates (e.g. 2,3 sialyltransferase and CMP-Sialic acid).

Further research may reveal the biological and therapeutic significance of specific glycoforms, thereby rendering the ability to produce such specific glycoforms desirable. To date, efforts have concentrated on making proteins with fairly well characterized glycosylation patterns, and expressing a cDNA encoding such a protein in one of the following higher eukaryotic protein expression systems:

1. Higher eukaryotes such as Chinese hamster ovary cells (CHO), mouse fibroblast cells and mouse myeloma cells (R. Werner, et al., Arzneimittel-Forschung-Drug rResearch 1998 48:870-880 (1998));
2. Transgenic animals such as goats, sheep, mice and others (Dente et al., *Genes and Development* 2:259-266 (1988); Cole et al., *J. Cell. Biochem.* 265:supplement 18D (1994); P. McGarvey et al., *Biotechnology* 13:1484-1487 (1995); Bardor et al., *Trends in Plant Science* 4:376-380 (1999));
3. Plants (*Arabidopsis thaliana*, tobacco etc.) (Staub et al., *Nature Biotechnology* 18:333-338 (2000); McGarvey et al., *Biotechnology* 13:1484-1487 (1995); Bardor et al., *Trends in Plant Science* 4:376-380 (1999));
4. Insect cells (*Spodoptera frugiperda* Sf9, Sf21, *Trichoplusia ni*, etc. in combination with recombinant baculorviruses such as *Autographa californica* multiple nuclear polybedrosis virus which infects lepidopteran cells (Altmann, et al., *Glycoconjugate Journal* 16:109-123 (1999)).

While most higher eukaryotes carry out glycosylation reactions that are similar to those found in humans, recombinant human proteins expressed in the above mentioned host systems invariably differ from their "natural" human counterpart (Raju, et al. *Glycobiology* 10:477-486 (2000)). Extensive development work has thus been directed at finding ways to improving the "human character" of proteins made in these expression systems. This includes the optimization of fermentation conditions and the genetic modification of protein expression hosts by introducing genes encoding enzymes involved in the formation of human like glycoforms (Werner et al., *Arzneimittel-Forschung-Drug Res.* 48:870-880 (1998); Weikert et al. *Nature Biotechnology* 17:1116-1121 (1999); Andersen et al., *Current Opinion in Biotechnology* 5:546-549 (1994); Yang et al., *Biotechnology and Bioengineering* 68:370-380 (2000)).

What has not been solved, however, are the inherent problems associated with all mammalian expression systems. Fermentation processes based on mammalian cell culture (e.g. CHO, Murine, or more recently, human cells) tend to be very slow (fermentation times in excess of one week are not uncommon), often yield low product titers, require expensive nutrients and cofactors (e.g. bovine fetal serum), are limited by programmed cell death (apoptosis), and often do not allow for the expression of particular therapeutically valuable proteins. More importantly, mammalian cells are susceptible to viruses that have the potential to be human pathogens and stringent quality controls are required to assure product safety. This is of particular concern since as many such processes require the addition of complex and temperature sensitive media components that are derived from animals (e.g. bovine calf serum), which may carry agents pathogenic to humans such as bovine spongiform encephalopathy (BSE) prions or viruses.

The production of therapeutic compounds is preferably carried out in a well-controlled sterile environment. An animal farm, no matter how cleanly kept, does not constitute such an environment. Transgenic animals are currently considered for manufacturing high volume therapeutic proteins such as: human serum albumin, tissue plasminogen activator, monoclonal antibodies, hemoglobin, collagen, fibrinogen and others. While transgenic goats and other transgenic animals (mice, sheep, cows, etc.) can be genetically engineered to produce therapeutic proteins at high concentrations in the milk, recovery is burdensome since every batch has to undergo rigorous quality control. A transgenic goat may produce sufficient quantities of a therapeutic protein over the course of a year, however, every batch of milk has to be inspected and checked for contamination by bacteria, fungi, viruses and prions. This requires an extensive quality control and assurance infrastructure to ensure product safety and regulatory compliance. In the case of scrapies and bovine spongiform encephalopathy, testing can take about a year to rule out infection. In the interim, trust in a reliable source of animals substitutes for an actual proof of absence. Whereas cells grown in a fermenter are derived from one well characterized Master Cell Bank (MCB), transgenic technology relies on different animals and thus is inherently non-uniform. Furthermore, external factors such as different food uptake, disease and lack of homogeneity within a herd may affect glycosylation patterns of the final product. It is known in humans, for example, that different dietary habits impact glycosylation patterns, and it is thus prudent to expect a similar effect in animals. Producing the same protein in fewer batch fermentations would be (1) more practical, (2) safer, and (3) cheaper, and thus preferable.

Transgenic plants have emerged as a potential source to obtain proteins of therapeutic value. However, high level expression of proteins in plants suffers from gene silencing, a mechanism by which highly expressed proteins are down regulated in subsequent generations. In addition, it is known that plants add xylose and a-1,3 linked fucose, a glycosylation pattern that is usually not found in human glycoproteins, and has shown to lead to immunogenic side effects in higher mammals. Growing transgenic plants in an open field does not constitute a well-controlled production environment. Recovery of proteins from plants is not a trivial matter and has yet to demonstrate cost competitiveness with the recovery of secreted proteins in a fermenter.

Most currently produced therapeutic glycoproteins are therefore expressed in mammalian cells and much effort has been directed at improving (i.e.g., humanizing) the glycosylation pattern of these recombinant proteins. Changes in medium composition as well as the co-expression of genes encoding enzymes involved in human glycosylation have been successfully employed (see, for example, Weikert et al., *Nature Biotechnology* 17:1116-1121 (1999)).

While recombinant proteins similar to their human counterparts can be made in mammalian expression systems, it is currently not possible to make proteins with a humanoid glycosylation pattern in lower eukaryotes (e.g., fungi and yeast). Although the core oligosaccharide structure transferred to the protein in the endoplasmic reticulum is basically identical in mammals and lower eukaryotes, substantial differences have been found in the subsequent processing reactions of the Golgi apparatus of fungi and mammals. In fact, even amongst different lower eukaryotes, there exists a great variety of glycosylation structures. This has prevented the use of lower eukaryotes as hosts for the production of recombinant human glycoproteins despite otherwise notable advantages over mammalian expression systems, such as: (1) generally higher product titers, (2) shorter fermentation times, (3) having an alternative for proteins that are poorly expressed in mammalian cells, (4) the ability to grow in a chemically defined protein free medium and thus not requiring complex animal derived media components, and (5) and the absence of retroviral infections of such hosts.

Various methylotrophic yeasts such as *Pichia pastoris, Pichia methanolica*, and *Hansenula polymorphs*, have played particularly important roles as eukaryotic expression systems since because they are able to grow to high cell densities and secrete large quantities of recombinant protein. However, as noted above, lower eukaryotes such as yeast do not glycosylate proteins like higher mammals. See, for example, U.S. Pat. No. 5,834,251 to Maras et al. (1994). Maras and Contreras have shown recently that *P. pastoris* is not inherently able to produce useful quantities (greater than 5%) of GlcNAcTransferase I accepting carbohydrate. (Martinet et al., *Biotechnology Letters* 20:1171-1177 (1998)). Chiba et al. (*J. Biol. Chem.* 273: 26298-26304 (1998)) have shown that *S. cerevisiae* can be engineered to provide structures ranging from $Man_8GlcNAc_2$ to $Man_5GlcNAc_2$ structures, by eliminating 1,6 mannosyltransferase (OCH1), 1,3 mannosyltransferase (MNN1) and mannosylphosphatetransferase (MNN4) and by targeting the catalytic domain of a-1,2-mannosidase I from *Aspergillus saitoi* into the ER of *S. cerevisiae*, by using a ER retrieval/targeting sequence (Chiba 1998, supra). However, this attempt resulted in little or no production of the desired $Man_5GlcNAc_2$. The model protein (carboxypeptidase Y) was trimmed to give a mixture consisting of 27% $Man_5GlcNAc_2$, 22% $Man_6GlcNAc_2$, 22% $Man_7GlcNAc_2$, 29% $Man_8GlcNAc_2$. As only the $Man_5GlcNAc_2$ glycans are susceptible to further enzymatic conversion to human glycoforms, this approach is very inefficient for the following reasons: In proteins having a single N-glycosylation site, at least 73% of all N-glycans will not be available for modification by GlcNAc transferase I. In a protein having two or three N-glycosylation sites, at least 93% or 98%, respectively, would not be accessible for modification by GlcNAc transferase I. Such low efficiencies of conversion are unsatisfactory for the production of therapeutic agents; given the large number of modifying steps each cloned enzyme needs to function at highest possible efficiency.

A number of reasons may explain the inefficiency in the production of glycan formation mentioned above. This may, in part, be due to the inefficient processing of glycans in the ER either by glucosidase I, II or resident ER mannosidase. A recently evolved class of mannosidase proteins has been identified in eukaryotes of the chordate phylum (including mammals, birds, reptiles, amphibians and fish) that is also involved in glucose removal. These glycosidic enzymes have been defined as endomannosidases. The activity of the endomannosidases has been characterized in the processing of N-linked oligosaccharides, namely, in removing a glucose α1,3 mannose dissacharide. The utility in removing of the glucose and mannose residues on oligosaccharides in the initial steps of N-linked oligosaccharide processing is known to be useful for the production of complex carbohydrates has been well-established. Although endomannosidases were originally detected in the trimming of $GlcMan_9GlcNAc_2$ to $Man_8GlcNAc_2$, they also process other glucosylated structures (FIG. 1). Overall, mono-glucosylated glycans are most efficiently modified although di- and tri-glucosylated glycans may also be processed to a lesser extent (Lubas et al., *J. Biol. Chem.* 263(8):3990-8 (1988)). Furthermore, not only is $GlcMan_9GlcNAc_2$ is the preferred substrate but other monoglucosylated glycans, such as $GlcMan_7GlcNAc_2$ and $GlcMan_5GlcNAc_2$, are trimmed (to $Man_6GlcNAc_2$ and $Man_4GlcNAc_2$, respectively) just as efficiently. The occurrence of this class of proteins so late in evolution suggests that this is a unique requirement to enhance the pronounced trimming of N-linked glycans, as observed in higher eukaryotes. This suggestion is further strengthened by the fact that endomannosidase is located in the Golgi and not the ER where complete deglucosylation has traditionally been reported to occur.

Previous research has shown that glucose excision occurs primarily in the ER through sequential action of glucosidase I and II (Moremen et al., *Glycobiology* 4: 113-125 (1994)). However, more recent research suggests the apparent alternate glucosidase II—independent deglucosylation pathway involving a quality control mechanism in the Golgi apparatus (Zuber et al., *Mol. Biol. Cell.* December; 11(12): 4227-40 (2000)). Studies in glucosidase II-deficient mouse lymphoma cells show evidence of the deglucosylation mechanism by the endomannosidase (Moore et al., *J. Biol. Chem.* 267(12):8443-51 (1992)). Furthermore, a mouse lymphoma cell line, PHAR2.7, has been isolated which has no glucosidase II activity resulting primarily in the production of the glycoforms $Glc_2Man_9GlcNAc_2$ and $Glc_2Man_8GlcNAc_2$ (Reitman et al., *J. Biol. Chem.* 257: 10357-10363 (1982)). Analysis of this latter cell line demonstrated that, despite the absence of glucosidase II, deglucosylated high mannose structures were present, thus, indicating the existence of an alternative processing pathway for glucosylated structures (Moore and Spiro, *J. Biol. Chem.* 267: 8443-8451 (1992)). The enzyme responsible for this glucosidase-independent pathway has been identified as endomannosidase (E.C. 3.2.1.130). Endomannosidase catalyzes the hydrolysis of mono-, di- and tri-glucosylated high mannose glycoforms, removing the glucose residue(s) present and the juxta-positioned mannose (Hiraizumi et al., *J. Biol. Chem.* 268: 9927-9935 (1993); Bause and Burbach, *Biol. Chem.* 377: 639-646 (1996)).

The endomannosidase does not appear to distinguish between differing mannose structures of a glucosylated glycoform, hydrolyzing $Glc_1Man_{9-5}GlcNAc_2$ to $Man_{8-4}GlcNAc_2$ (Lubas and Spiro, *J. Biol. Chem.* 263: 3990-3998 (1988)). To date, the only endomannosidase to have been cloned is from the rat liver. Rat liver endomannosidase encodes a predicted open reading frame (ORF) of 451 amino acids with a molecular mass of 52 kDa (Spiro et al., *J. Biol. Chem.* 272: 29356-29363 (1997)). This enzyme has a neutral pH optimum and does not appear to have any specific cation requirement (Bause and Burbach 1996, supra). Unlike the glucosidase enzymes, which are localized in the ER, the endomannosidase is primarily localized in the Golgi (Zuber et al., *Mol. Biol. Cell* 11: 4227-4240 (2000)), suggesting that it may play a quality control role by processing glucosylated glycoforms leaking from the ER.

Given the utility of modifying glucosylated glycans for the production of human-like glycoproteins, a method for modifying glucosylated glycans by expressing an endomannosidase activity in a host cell would be desirable.

SUMMARY OF THE INVENTION

Methods have been developed for modifying a glucosylated N-glycan by genetically engineering strains of non-mammalian eukaryotes which are able to produce recombinant glycoproteins substantially equivalent to their human counterparts. These cell lines, including yeast, filamentous fungi, insect cells, and plant cells grown in suspension culture, have genetically modified glycosylation pathways allowing them to carry out a sequence of enzymatic reactions which mimic the processing of glycoproteins in humans. As described herein, strains have been developed to express catalytically active endomannosidase genes to enhance the processing of the N-linked glycan structures with the overall goal of obtaining a more human-like glycan structure. In addition, cloning and expression of a novel human and mouse endomannosidase are also disclosed. The method of the present invention can be adapted to engineer cell lines having desired glycosylation structures useful in the production of therapeutic proteins.

BRIEF DESCRIPTION OF THE DRAWINGS

FIG. 3 shows a BLAST analysis of rat endomannosidase to identify homologues. Panel A shows identification of a human sequence (SEQ ID NO:24) showing 88% identity to the C-terminus of rat endomannosidase (SEQ ID NO:23). Panel B (residues 1-23 of SEQ ID NO:24, aligned with resides 173-195 of SEQ ID NO:25, respectively in order of appearance) shows the N-terminus of isolated sequence from Panel A which was used to isolate the 5' region of the human endomannosidase in Panel C. Panel C shows sequence of the potential N-terminus of human endomannosidase (SEQ ID NO:25).

FIG. 4 shows nucleotide and amino acid sequences of human liver endomannosidase. Nucleotide sequence (upper) (SEQ ID NO:1) and one-letter amino acid sequence (lower) (SEQ ID NO:2) of human endomannosidase are shown with residue numbers labeled on the left. The nucleotide region in bold represents the overlapping segments of Genbank sequences gi:18031878 (underlined) and gi:20547442 (regular text) used to assemble the putative full-length human liver endomannosidase. The putative transmembrane domain identified by Kyte and Doolittle analysis (*J. Mol. Biol.* 157: 105-132 (1982)) (see FIG. 5) is highlighted by an open box.

FIG. 6 shows nucleotide and amino acid sequences of mouse endomannosidase (Genbank AK030141). Nucleotide sequence (upper) (SEQ ID NO:3) and one-letter amino acid sequence (lower) (SEQ ID NO:4) of mouse endomannosidase are shown with residue numbers labeled on the left. The putative transmembrane domain identified by Kyte and Doolittle analysis (*J. Mol. Biol.* 157: 105-132 (1982)) is highlighted by an open box.

FIG. 7 shows the alignment of three endomannosidase open-reading frames. The human (SEQ ID NO:2), mouse (SEQ ID NO:4) and rat (SEQ ID NO:26) endomannosidase ORFs were aligned using the Megalign software of the DNASTAR suite of programs. The algorithm chosen for the analysis was the CLUSTAL V version (Higgins and Sharp *Comput. Appl. Biosci.* 5, 151-153 (1989)). Residues displayed by shading represent amino acids that are identical between at least two of the ORFs. The amino acid position of each ORF is presented to the left of the aligned sequence.

FIG. 13 shows a high performance liquid chromatogram in vitro assay for rat and human endomannosidase activity. Panel A shows the hexose 6 standard $GlcMan_5GlcNAc_2$ in BMMY. Panel B shows glycan substrate produced from rat endomannosidase incubated with supernatant from *P. pastoris* YSH13. Panel C shows glycan substrate produced from human endomannosidase incubated with supernatant from *P. pastoris* YSH16. See FIG. 14 for structures corresponding to (i) and (ii).

DETAILED DESCRIPTION OF THE INVENTION

Figure 1:
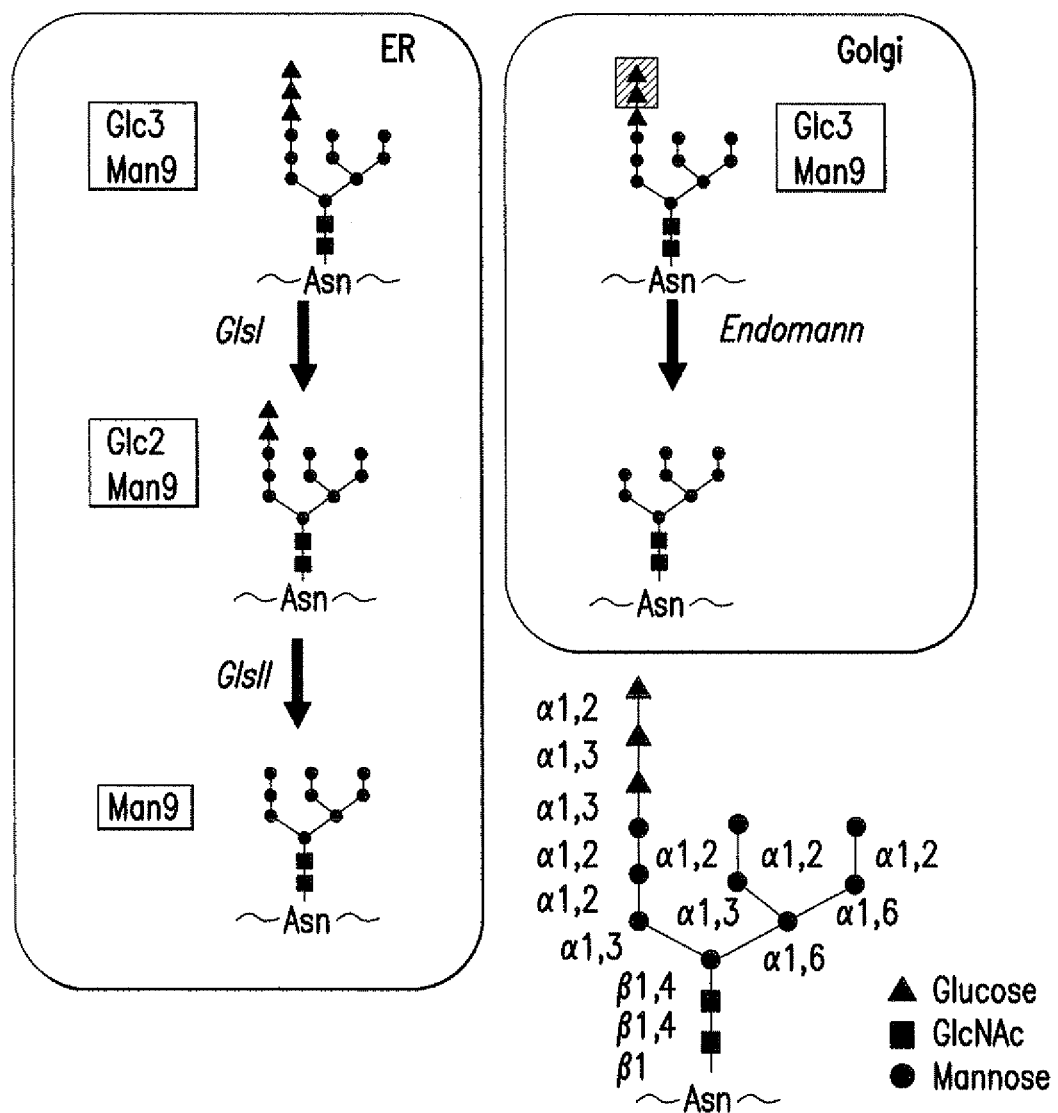
FIG. 1 is a schematic diagram of an endomannosidase modifying mono-, di- and tri-glucosylated glycans in the Golgi in comparison to glucose processing of N-glycans in the ER. Highlighted are additional glucose residues that can be hydrolyzed.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Introduction to Glycobiology, Maureen E. Taylor, Kurt Drickamer, Oxford Univ. Press (2003); Worthington Enzyme Manual, Worthington Biochemical Corp. Freehold, N.J.; Handbook of Biochemistry: Section A Proteins Vol I 1976 CRC Press; Handbook of Biochemistry: Section A Proteins Vol II 1976 CRC Press; Essentials of Glycobiology, Cold Spring Harbor Laboratory Press (1999). The nomenclatures used in connection with, and the laboratory procedures and techniques of, biochemistry and molecular biology described herein are those well known and commonly used in the art.

All publications, patents and other references mentioned herein are incorporated by reference.

The following terms, unless otherwise indicated, shall be understood to have the following meanings:

As used herein, the term "N-glycan" refers to an N-linked oligosaccharide, e.g., one that is attached by an asparagine-N-acetylglucosamine linkage to an asparagine residue of a polypeptide. N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., fucose and sialic acid) that are added to the Man$_3$GlcNAc$_2$ ("Man3") core structure. N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. The "trimannose core" is the pentasaccharide core having a Man3 structure. Complex N-glycans may also have galactose ("Gal") residues that are optionally modified with sialic acid or derivatives ("NeuAc", where "Neu" refers to neuraminic acid and "Ac" refers to acetyl). Complex N-glycans may also have intrachain substitutions comprising "bisecting" GlcNAc and core fucose ("Fuc"). A "hybrid" N-glycan has at least one GlcNAc on the terminal of the 1,3 mannose arm of the trimannose core and zero or more mannoses on the 1,6 mannose arm of the trimannose core.

Abbreviations used herein are of common usage in the art, see, e.g., abbreviations of sugars, above. Other common abbreviations include "PNGase", which refers to peptide N-glycosidase F (EC 3.2.2.18); "GlcNAc Tr (I-III)", which refers to one of three N-acetylglucosaminyltransferase enzymes; "NANA" refers to N-acetylneuraminic acid.

As used herein, the term "secretion pathway" refers to the assembly line of various glycosylation enzymes to which a lipid-linked oligosaccharide precursor and an N-glycan substrate are sequentially exposed, following the molecular flow of a nascent polypeptide chain from the cytoplasm to the endoplasmic reticulum (ER) and the compartments of the Golgi apparatus. Enzymes are said to be localized along this pathway. An enzyme X that acts on a lipid-linked glycan or an N-glycan before enzyme Y is said to be or to act "upstream" to enzyme Y; similarly, enzyme Y is or acts "downstream" from enzyme X.

As used herein, the term "antibody" refers to a full antibody (consisting of two heavy chains and two light chains) or a fragment thereof. Such fragments include, but are not limited to, those produced by digestion with various proteases, those produced by chemical cleavage and/or chemical dissociation, and those produced recombinantly, so long as the fragment remains capable of specific binding to an antigen. Among these fragments are Fab, Fab', F(ab')2, and single chain Fv (scFv) fragments. Within the scope of the term "antibody" are also antibodies that have been modified in sequence, but remain capable of specific binding to an antigen. Example of modified antibodies are interspecies chimeric and humanized antibodies; antibody fusions; and heteromeric antibody complexes, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513), the disclosure of which is incorporated herein by reference in its entirety).

As used herein, the term "mutation" refers to any change in the nucleic acid or amino acid sequence of a gene product, e.g., of a glycosylation-related enzyme.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, (herein incorporated by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2× SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, D. W., et al., *Technique*, 1, pp. 11-15 (1989) and Caldwell, R. C. & Joyce G. F., *PCR Methods Applic.*, 2, pp. 28-33 (1992)); and "oligonucleotide-directed mutagenesis" (a process which enables the generation of site-specific mutations in any cloned DNA segment of interest. See, e.g., Reidhaar-Olson, J. F. & Sauer, R. T., et al., *Science*, 241, pp. 53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide.

Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992, hereby incorporated by reference.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, (1992) Amino Acid and Peptide Synthesis, Oxford University Press; Jung, (1997) Combinatorial Peptide and Nonpeptide Libraries: A Handbook John Wiley; Bodanszky et al., (1993) Peptide Chemistry—A Practical Textbook, Springer Verlag; "Synthetic Peptides: A Users Guide", G. A. Grant, Ed, W. H. Freeman and Co., 1992; Evans et al. *J. Med Chem.* 30:1229 (1987); Fauchere, *J. Adv. Drug Res.* 15:29 (1986); Veber and Freidinger *TINS* p. 392 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99%, 99.5% or 99.9% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, herein incorporated by reference).

The following six groups each contain amino acids that are conservative substitutions for one another: 1) Serine (S), Threonine (T); 2) Aspartic Acid (D), Glutamic Acid (E); 3)

Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST (Altschul, S. F. et al. (1990) *J. Mol. Biol.* 215:403-410; Gish and States (1993) *Nature Genet.* 3:266-272; Madden, T. L. et al. (1996) *Meth. Enzymol.* 266:131-141; Altschul, S. F. et al. (1997) *Nucleic Acids Res.* 25:3389-3402; Zhang, J. and Madden, T. L. (1997) *Genome Res.* 7:649-656), especially blastp or tblastn (Altschul et al., 1997). Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and its embodiments, the word "comprise" or variations such as "comprises" or "comprising", will be understood to refer to the inclusion of a stated integer or group of integers but not the exclusion of any other integer or group of integers.

Nucleic Acid Sequences Encoding Human Endomannosidase Gene

The rat endomannosidase has been cloned (Spiro et al., *J. Biol. Chem.* 272(46):29356-29363 (1997)). Although the rat endomannosidase is the only cloned member of this family to date, genes and ESTs that show significant homology to this ORF, and in particular to the rat endomannosidase catalytic domain, are in databases. By performing a protein BLAST search using the rat endomannosidase protein sequence (Genbank gi:2642187) we identified two hypothetical human proteins in Genbank having regions of significant homology with the rat endomannosidase sequence (Example 2; FIGS. 3A-C). Combining 5' and 3' regions of these two hypothetical proteins into one ORF produced a putative sequence of 462 amino acids (FIG. 4) and a predicted molecular mass of 54 kDa. Alignment of this putative human endomannosidase sequence to the known rat sequence indicated that the C-termini of these proteins are highly conserved but that the N-termini are more varied (FIG. 7). It is likely that the conserved region (i.e., from the motif 'DFQ(K/R)SDRIN' to the C-terminus), corresponds to the catalytic domain in each endomannosidase, or at least to a region essential for activity.

Based on the above-deduced human endomannosidase gene sequence, we constructed primers and amplified an open reading frame (ORF) from a human liver cDNA library by PCR (Example 2). The nucleic acid sequence which encodes that ORF is 77.8% identical across its length to the full-length nucleic acid sequence encoding the rat endomannosidase ORF (sequence pair distances using the Clustal methods with weighted residue weight table). At the amino acid sequence level, the human and rat endomannosidase proteins are predicted to be 76.7% identical overall. In the more conserved region noted above (i.e., from the motif 'DFQ(K/R)SDRIN' to the C-terminus), the proteins are 86.6% identical overall. Unlike the rat protein, the predicted human protein has a very hydrophobic region at the N-terminus (residues 10 to 26) which may be a transmembrane region (FIG. 4, boxed). The human endomannosidase (unlike the rat protein), is predicted to be a type-II membrane protein, as are most other higher eukaryotic mannosidases.

We subcloned the human endomannosidase ORF into various vectors, including a yeast integration plasmid (Example 3), to study the effect of its expression on the N-glycosylation pathway of a lower eukaryotic host cell, *Pichia pastoris*. As described below, engineering the human mannosidase enzyme into the glycosylation pathway of a host cell significantly affects the subsequent glycosylation profile of proteins produced in that host cell and its descendants. Preferably, the host cell is engineered to express a human mannosidase enzyme activity (e.g., from a catalytic domain) in combination with one or more other engineered glycosylation activities to make human-like glycoproteins.

Accordingly, the present invention provides isolated nucleic acid molecules, including but not limited to nucleic acid molecules comprising or consisting of a full-length nucleic acid sequence encoding human endomannosidase. The nucleic acid sequence and the ORF of human endomannosidase are set forth in FIG. 4 and as SEQ ID NO:1. The encoded amino acid sequence is also set forth in FIG. 4 and in SEQ ID NO:2.

In one embodiment, the invention provides isolated nucleic acid molecules having a nucleic acid sequence comprising or consisting of a wild-type human endomannosidase coding sequence (SEQ ID NO:1); homologs, variants and derivatives thereof; and fragments of any of the above. In one embodiment, the invention provides a nucleic acid molecule comprising or consisting of a sequence which is a degenerate variant of the wild-type human endomannosidase coding sequence (SEQ ID NO:1). In a preferred embodiment, the invention provides a nucleic acid molecule comprising or consisting of a sequence which is a variant of the human endomannosidase coding sequence (SEQ ID NO:1) having at least 65% identity to the wild-type gene. The nucleic acid sequence can preferably have at least 70%, 75% or 80% identity to the wild-type human endomannosidase coding sequence (SEQ ID NO:1) (specifically excluding, however, the rat endomannosidase gene, which is about 78% identical overall). Even more preferably, the nucleic acid sequence can have 85%, 90%, 95%, 98%, 99%, 99.9%, or higher, identity to the wild-type human endomannosidase coding sequence (SEQ ID NO:1).

In another embodiment, the nucleic acid molecule of the invention encodes a polypeptide comprising or consisting of the amino acid sequence of SEQ ID NO:2. Also provided is a nucleic acid molecule encoding a polypeptide sequence that is at least 65% identical to SEQ ID NO:2 (specifically excluding, however, the rat endomannosidase polypeptide, which is about 77% identical overall). Typically the nucleic acid molecule of the invention encodes a polypeptide sequence of at least 70%, 75% or 80% identity to SEQ ID NO:2. Preferably, the encoded polypeptide is at least 85%, 90% or 95% identical to SEQ ID NO:2, and the identity can even more preferably be 98%, 99%, 99.9% or even higher.

The invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45 or 50 contiguous nucleotides. Even more preferably, the fragments of the nucleic acid sequences contain at least 60, 70, 80, 90, 100 or more contiguous nucleotides. In a further embodiment of the invention, the nucleic acid sequence is a variant of the fragment having at least 65% identity to the wild-type gene fragment. The nucleic acid sequence can preferably have at least 70%, 75% or 80% identity to the wild-type gene fragment. Even more preferably, the nucleic acid sequence can have 85%, 90%, 95%, 98%, 99%, 99.9% or even higher identity to the wild-type gene fragment.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (*Practical Approach Series*), Schena (ed.), Oxford University Press (1999) (ISBN: 0199637768); *Nature Genet.* 21(1)(suppl):1-60 (1999); *Microarray Biochip: Tools and Technology*, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); *DNA Microarrays: A Practical Approach* (*Practical Approach Series*), Schena (ed.), Oxford University Press (1999) (ISBN: 0199637768); *Nature Genet.* 21(1)(suppl):1-60 (1999); *Microarray Biochip: Tools and Technology*, Schena (ed.), Eaton Publishing Company/BioTechniques Books Division (2000) (ISBN: 1881299376), the disclosures of each of which is incorporated herein by reference in its entirety. In another embodiment, isolated nucleic acid molecules encoding a polypeptide having endomannosidase activity are provided. As is well known in the art, enzyme activities can be measured in various ways. Alternatively, the activity of the enzyme can be followed using chromatographic techniques, such as by high performance liquid chromatography. Chung and Sloan, *J. Chromatogr.* 371:71-81 (1986). Other methods and techniques may also be suitable for the measurement of enzyme activity, as would be known by one of skill in the art.

In another embodiment, the nucleic acid molecule of the invention encodes a polypeptide having the amino acid sequence of SEQ ID NO:2. The nucleic acid sequence of the invention encodes a polypeptide having at least 77% identity to the wild-type rat endomannosidase gene (Genbank AF023657). In another embodiment, the nucleic acid sequence has at least 87% identity to the wild-type rat endomannosidase catalytic domain. In an even more preferred embodiment, the nucleic acid sequence can have 90%, 95%, 98%, 99%, 99.9% or even higher identity to the wild-type rat endomannosidase gene.

Polypeptides encoded by the nucleic acids of the invention, especially peptides having a biological (e.g., catalytic or other) and/or immunological activity, are also provided by the invention.

Nucleic Acid Sequences Encoding Mouse Endomannosidase Gene

The mouse endomannosidase gene is cloned by designing primers that complement the putative homologous regions between the mouse and human endomannosidase genes and PCR amplifying to generate a probe which can be used to pull out a full-length cDNA encoding mouse endomannosidase (Example 2). The nucleotide and predicted amino acid sequence of the mouse endomannosidase open reading frame (ORF) is set forth in FIG. 6 and as SEQ ID NOs:3 and 4, respectively.

The mouse ORF shows substantial homology to the known rat endomannosidase and the human liver endomannosidase of the present invention (FIG. 7). Specifically, the nucleic acid sequence which encodes the mouse endomannosidase ORF is 86.0% and 84.2% identical across its length to the full-length nucleic acid sequence encoding the rat and the human endomannosidase ORFs, respectively (sequence pair distances using the Clustal methods with weighted residue weight table). At the amino acid sequence level, the mouse and rat endomannosidase proteins are predicted to be 82.3% identical, and the mouse and human endomannosidase proteins are predicted to be 84.9% identical overall. In the more conserved region noted above (i.e., from the motif 'DFQ(K/R)SDRIN' to the C-terminus), the mouse and rat proteins are 92.3% identical, and the mouse and human proteins are 86.1% identical, overall.

Accordingly, the present invention further provides isolated nucleic acid molecules and variants thereof encoding the mouse endomannosidase. In one embodiment, the invention provides an isolated nucleic acid molecule having a nucleic acid sequence comprising or consisting of the gene encoding the mouse endomannosidase (SEQ ID NO:3), homologs, variants and derivatives thereof.

Accordingly, the present invention provides isolated nucleic acid molecules, including but not limited to nucleic acid molecules comprising or consisting of a full-length nucleic acid sequence encoding mouse endomannosidase. The nucleic acid sequence and the ORF of mouse endomannosidase are set forth in FIG. 6 and as SEQ ID NO:3. The encoded amino acid sequence is also set forth in FIG. 6 and in SEQ ID NO:4.

In one embodiment, the invention provides isolated nucleic acid molecules having a nucleic acid sequence comprising or consisting of a wild-type mouse endomannosidase coding sequence (SEQ ID NO:3); homologs, variants and derivatives thereof; and fragments of any of the above. In one embodiment, the invention provides a nucleic acid molecule comprising or consisting of a sequence which is a degenerate variant of the wild-type mouse endomannosidase coding sequence (SEQ ID NO:3). In a preferred embodiment, the invention provides a nucleic acid molecule comprising or consisting of a sequence which is a variant of the mouse endomannosidase coding sequence (SEQ ID NO:3) having at least 65% identity to the wild-type gene. The nucleic acid sequence can preferably have at least 70%, 75%, 80% or 85% identity to the wild-type human endomannosidase coding sequence (SEQ ID NO:3) (specifically excluding, however, the rat endomannosidase gene, which is about 86% identical overall). Even more preferably, the nucleic acid sequence can have 90%, 95%, 98%, 99%, 99.9%, or higher, identity to the wild-type mouse endomannosidase coding sequence (SEQ ID NO:3).

In another embodiment, the nucleic acid molecule of the invention encodes a polypeptide comprising or consisting of the amino acid sequence of SEQ ID NO:4. Also provided is a nucleic acid molecule encoding a polypeptide sequence that is at least 65% identical to SEQ ID NO:4 (specifically excluding, however, the rat endomannosidase polypeptide, which is about 82% identical overall). Typically the nucleic acid molecule of the invention encodes a polypeptide sequence of at least 70%, 75% or 80% identity to SEQ ID NO:4. Preferably, the encoded polypeptide is at least 85%, 90% or 95% identical to SEQ ID NO:4, and the identity can even more preferably be 98%, 99%, 99.9% or even higher.

The invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45 or 50 contiguous nucleotides. Even more preferably, the fragments of the nucleic acid sequences contain at least 60, 70, 80, 90, 100 or more contiguous nucleotides. In a further embodiment of the invention, the nucleic acid sequence is a variant of the fragment having at least 65% identity to the wild-type gene fragment. The nucleic acid sequence can preferably have at least 70%, 75% or 80% identity to the wild-type gene fragment. Even more preferably, the nucleic acid sequence can have 85%, 90%, 95%, 98%, 99%, 99.9% or even higher identity to the wild-type gene fragment.

In another embodiment, the nucleic acid molecule of the invention encodes a polypeptide comprising or consisting of the amino acid sequence of SEQ ID NO:4. Also provided is a nucleic acid molecule encoding a polypeptide sequence that is at least 65% identical to SEQ ID NO:4 (specifically excluding, however, the rat endomannosidase polypeptide, which is about 82% identical overall). Typically the nucleic acid molecule of the invention encodes a polypeptide sequence of at least 70%, 75% or 80% identity to SEQ ID NO:4. Preferably, the encoded polypeptide is at least 85%, 90% or 95% identical to SEQ ID NO:4, and the identity can even more preferably be 98%, 99%, 99.9% or even higher.

In a preferred embodiment, the nucleic acid molecule of the invention encodes a polypeptide having at least 83% identity to the wild-type rat endomannosidase gene (Genbank AF023657). In another embodiment, the nucleic acid sequence encoding an amino acid sequence has at least 93% identity to the wild-type rat endomannosidase catalytic domain. In an even more preferred embodiment, the nucleic acid sequence can have 94%, 95%, 98%, 99%, 99.9% or even higher identity to the wild-type rat endomannosidase gene.

Polypeptides encoded by the nucleic acids of the invention, especially peptides having a biological (e.g., catalytic or other) and/or immunological activity, are also provided by the invention.

Characterization of Encoded Endomannosidase Products

The human liver endomannosidase and the putative mouse endomannosidase are the second and third members of a newly developing family of glycosidic enzymes, with the rat endomannosidase enzyme being the first such member. Sequence comparison of the human, mouse and rat ORFS (FIG. 7) demonstrates high homology from the motif 'DFQ (K/R)SDRI' to the C-termini of the sequences suggesting that this region encodes an essential fragment of the protein, and potentially, the catalytic domain. In contrast, the lower homology within the N-termini of the proteins demonstrates evolutionary divergence. Like the majority of glycosidases and glycosyltransferases, the mouse and human enzymes have a hydrophobic region indicative of a transmembrane domain. Such a domain would facilitate the orientation and localization of the enzyme in the secretory pathway. In contrast, the rat endomannosidase does not have a transmembrane domain but does have a glycine residue at position 2 (Spiro 1997, supra). This penultimate glycine residue has the potential to be myristoylated which in turn provides a mechanism for membrane localization (Boutin, *Cell Signal* 9: 15-35 (1997)). Alternatively, myristoylation may not be the means of rat endomannosidase localization to the Golgi (Zuber 2000, supra)—protein-protein interactions may be the determining mechanism.

Like the rat endomannosidase, both the human and mouse isoforms are predicted to localize to the Golgi based on the activity of this class of proteins. Traditionally, the removal of glucose from N-glycans was thought to occur in the ER by glucosidases I and II. However, the characterization of endomannosidase and its localization to the cis and medial cisternae of the Golgi demonstrates that glucose trimming does occur subsequent to glucosidase localization (Roth et al. *Biochimie* 85: 287-294 (2003)).

The specific role that endomannosidase fulfills is currently uncertain. Affinity-purification of rat endomannosidase demonstrated the co-purification with calreticulin suggesting its role in the quality control of N-glycosylation (Spiro et al., *J. Biol. Chem.* 271: 11588-11594 (1996)). Alternatively, endomannosidase may provide the cell with the ability to recover and properly mature glucosylated structures that have by-passed glucosidase trimming. Thus, removing the glucose-α1,3-mannose dimer from a glucosylated high mannose structure presents a substrate for the resident Golgi glycosidic and glycosyltransferase enzymes, enabling the maturation of the N-glycans.

We analyzed the tissue distribution of human endomannosidase and, like the rat isoform (Spiro (1997)), it was widespread in the tissues examined (FIG. 8) (Example 6). The liver and kidney demonstrated high expression levels but the pattern in the remainder of the tissues was significantly different. Interestingly, in contrast to the human endomannosidase, the rat isoform shows high expression levels in both the brain and lung (Spiro (1997)). The widespread expression of both isoforms of this enzyme in rat and human suggests that endomannosidase may play a house-keeping role in the processing of N-glycans.

Figure 9:
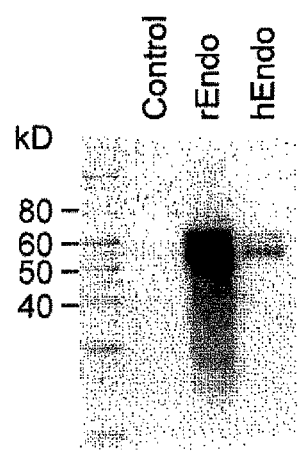
FIG. 9 depicts a Western blot analysis of prepurification on Ni-resin of secreted N-terminal tagged endomannosidase, samples from control (GS115) (A), rEndo (YSH89) (B) and hEndo (YSH90) (C) strains. The samples were detected using anti-FLAG M2 antibody (Stratagene, La Jolla, Calif.).

Expression in *P. pastoris* of the human endomannosidase of the invention confirms that the isolated ORF has activity. Interestingly, the rat isoform, though highly homologous at the nucleotide and protein levels, is expressed at levels at least five-fold higher than the human protein as seen on Western Blots (FIG. 9). It is possible that rat enzyme is inherently more stable during expression or in the culture medium.

Both recombinantly expressed endomannosidase enzymes were processed at their C-termini. In the case of the human enzyme, C-terminal processing appeared to be complete (based on apparent total conversion of the 59 kDa band to the 54 kDa form, presumably due to the lower expression level). In contrast, though the majority of the rat isoform was the 54 kDa form, some of the 59 kDa band remained (Example 7). Likewise, when the rat endomannosidase was expressed in *Escherichia coli*, the protein was proteolytically processed at the C-terminus over time (Spiro 1997, supra). Furthermore, affinity chromatographic purification of the rat isoform from rat liver demonstrated the presence of two forms, 56 and 60 kDa (Hiraizumi et al., *J. Biol. Chem.* 269: 4697-4700 (1994)). Together, these data indicate that both the human and rat endomannosidase proteins are susceptible to proteolytic processing. Based on the similar sizes of the two enzymes following proteolysis, the cleavage site is likely the same. Whether the cleavage site in the bacterial, yeast and mammalian systems is the same remains to be determined. Further characterization of the endomannosidase shows an optimal activity at about pH 6.2 (Example 9) and a temperature optimum of about 37° C. (Example 9).

The isolation and characterization of the human endomannosidase and the identification of the mouse homologue expands this family of glycosidases from a solitary member consisting of the rat isoform. This in turn has allowed us to characterize further this family of proteins. Indeed, this has allowed us to demonstrate that, while the C-terminal sequences of these proteins are highly conserved, variations in the N-terminal architecture occur. A previously reported phylogenetic survey of endomannosidase indicated that this protein has emerged only recently during evolution and is restricted to members of the chordate phylum, which includes mammals, birds, reptiles, amphibians and bony fish, with the only exception being that it has also been identified in Mollusca (Dairaku and Spiro, *Glycobiology* 7: 579-586 (1997)). Therefore, the isolation of more diversified members of this family of proteins will expectedly demonstrate further variations in endomannosidase structure and, potentially, activity.

Utility of Endomannosidase Expression

Figure 2:
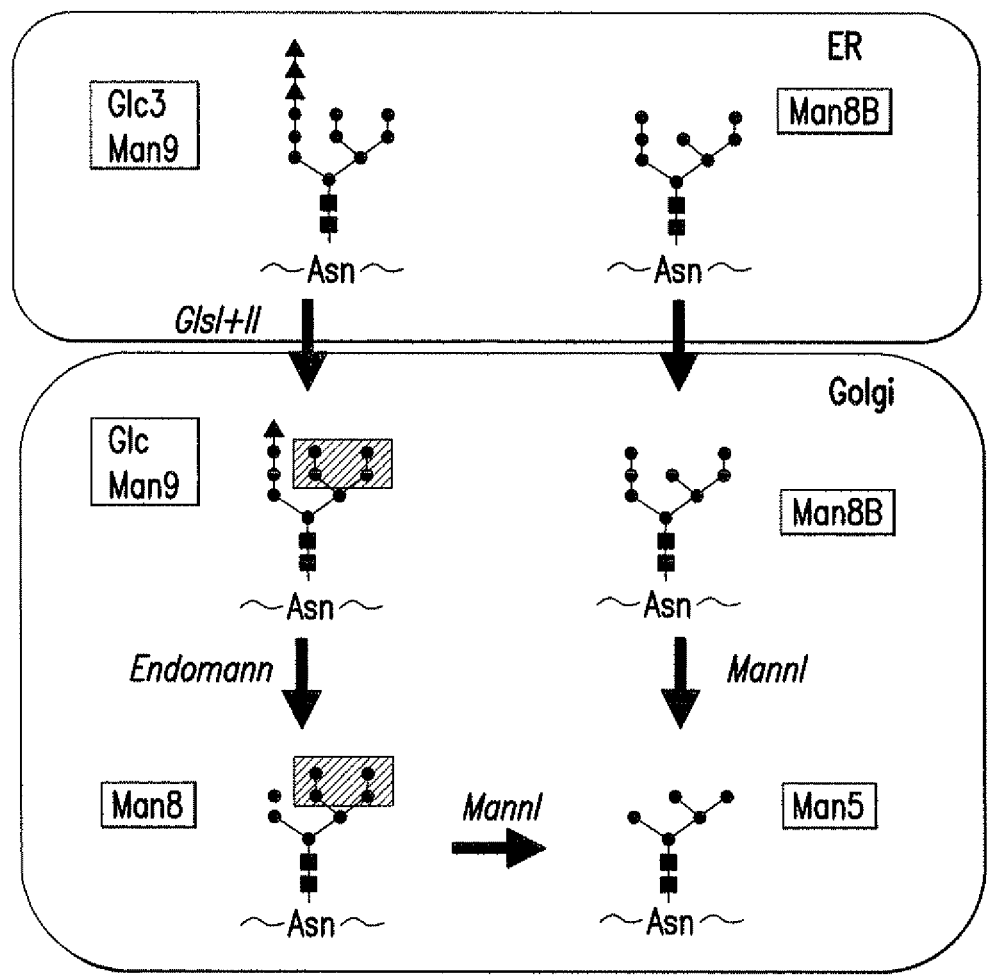
FIG. 2 is a schematic diagram of an endomannosidase processing the glucosylated structure $Glc_3Man_9GlcNAc_2$ to $Man_5GlcNAc_2$ glycans in the Golgi. Highlighted mannose residues represent constituents which, in various combinations, produce various types of high mannan glycans that may be substrates for the endomannosidase.
Figure 5:
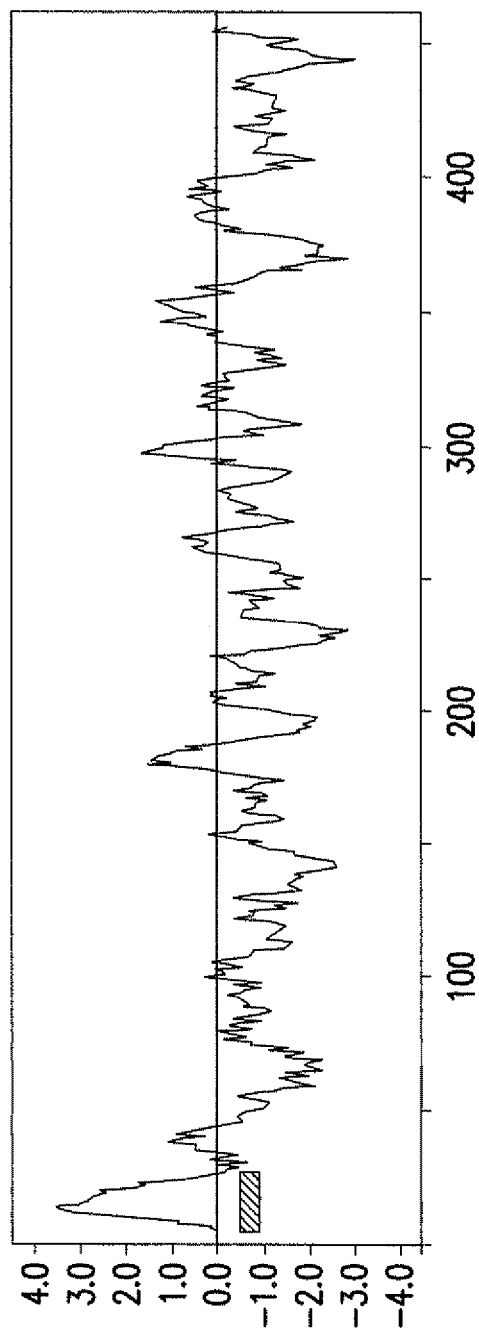
FIG. 5 shows the hydropathy plot of the amino acid sequence of the human endomannosidase, produced according to the method of Kyte and Doolittle ((1982) supra), using the web-based software GREASE and a window of 11 residues. The filled-in box represents an N-terminal region of high hydrophobicity, suggesting the presence of a putative transmembrane domain. This region is also represented in FIG. 4 by an open box (amino acid residues 10-26).

The human and mouse endomannosidase enzymes or catalytic domains (and nucleic acid molecules of the invention encoding such activities) will each be useful, e.g., for modifying certain glycosylation structures, in particular, for hydrolyzing a composition comprising at least one glucose residue and one mannose residue on a glucosylated glycan structure (FIG. 1 and FIG. 2). In one embodiment, the encoded enzyme catalyzes the cleavage of a di- tri-, or tetra-saccharide composition comprising at least one glucose residue and one mannose residue of glucosylated glycan precursors (FIG. 1). In another embodiment, the encoded enzyme also modifies a number of glucosylated structures, including $Glc_{1-3}Man_{9-5}GlcNAc_2$ (FIG. 2). One or more nucleic acids and/or polypeptides of the invention are introduced into a host cell of choice to modify the glycoproteins produced by that host cell.

Cellular Targeting of Endomannosidase in Vivo

Although glucosidases act upon high mannan glycans in the ER, some mannans escape the ER without proper modification and, thus, mannans with undesired glycosylations move through the secretory pathway. Previous studies suggest that in higher eukaryotes a fraction of glucosylated mannose structures does bypass the quality control of the ER, and that endomannosidase is present in the subsequent compartment to recover this fraction. Accordingly, in a feature of the present invention, the endomannosidase modifies the glucosylated mannose structures that have bypassed the ER. In a preferred embodiment, the endomannosidase enzyme encoded by the nucleic acid of the present invention is localized in the Golgi, trans Golgi network, transport vesicles or the ER. The enzymes are involved in the trimming of glucosylated high mannan glycans in yeast. For example, the glucosylated structure GlcMan$_9$GlcNAc$_2$, which has bypassed the ER glucosidase I and II enzymes, is modified by the endomannosidase in which at least a glucose-mannose residue is hydrolyzed producing Man$_8$GlcNAc$_2$. The endomannosidase enzymes of the present invention act as a quality control step in the Golgi, recovering the glucosylated high mannan glycans and removing a composition comprising at least one glucose residue and one mannose residue.

Combinatorial Nucleic Acid Library Encoding

Endomannosidase Catalytic Domains

In another aspect of the invention, one or more chimeric nucleic acid molecules encoding novel endomannosidase proteins is constructed by forming a fusion protein between an endomannosidase enzyme and a cellular targeting signal peptide, e.g., by the in-frame ligation of a DNA fragment encoding a cellular targeting signal peptide with a DNA fragment encoding an endomannosidase enzyme or catalytically active fragment thereof. Preferably, one or more fusion proteins are made in the context of an endomannosidase combinatorial DNA library. See generally WO 02/00879 and the publication of U.S. application Ser. No. 10/371,877 (filed Feb. 20, 2003); each of which is incorporated herein by reference in nits entirety. The endomannosidase DNA library comprises a wide variety of fusion constructs, which are expressed in a host cell of interest, e.g., by using an integration plasmid such as the pRCD259 (Example 5).

Targeting Peptide Sequence Sub-Libraries

Another useful sub-library includes nucleic acid sequences encoding targeting signal peptides that result in localization of a protein to a particular location within the ER, Golgi, or trans Golgi network. These targeting peptides may be selected from the host organism to be engineered as well as from other related or unrelated organisms. Generally such sequences fall into three categories: (1) N-terminal sequences encoding a cytosolic tail (ct), a transmembrane domain (tmd) and part or all of a stem region (sr), which together or individually anchor proteins to the inner (lumenal) membrane of the Golgi; (2) retrieval signals which are generally found at the C-terminus such as the HDEL or KDEL tetrapeptide; and (3) membrane spanning regions from various proteins, e.g., nucleotide sugar transporters, which are known to localize in the Golgi.

In the first case, where the targeting peptide consists of various elements (cytosolic tail (ct), transmembrane domain (tmd) and stem region (sr)), the library is designed such that the ct, the tmd and various parts of the stem region are represented. Accordingly, a preferred embodiment of the sub-library of targeting peptide sequences includes ct, tmd, and/or sr sequences from membrane-bound proteins of the ER or Golgi. In some cases it may be desirable to provide the sub-library with varying lengths of sr sequence. This may be accomplished by PCR using primers that bind to the 5' end of the DNA encoding the cytosolic region and employing a series of opposing primers that bind to various parts of the stem region.

Still other useful sources of targeting peptide sequences include retrieval signal peptides, e.g. the tetrapeptides HDEL or KDEL, which are typically found at the C-terminus of proteins that are transported retrograde into the ER or Golgi. Still other sources of targeting peptide sequences include (a) type II membrane proteins, (b) the enzymes with optimum pH, (c) membrane spanning nucleotide sugar transporters that are localized in the Golgi, and (d) sequences referenced in Table 1.

TABLE 1

Sources of useful compartmental targeting sequences

| Gene or Sequence | Organism | Function | Location of Gene Product |
|---|---|---|---|
| MNSI | A. nidulans | α-1,2-mannosidase | ER |
| MNSI | A. niger | α-1,2-mannosidase | ER |
| MNSI | S. cerevisiae | α-1,2-mannosidase | ER |
| GLSI | S. cerevisiae | glucosidase | ER |
| GLSI | A. niger | glucosidase | ER |
| GLSI | A. nidulans | glucosidase | ER |
| HDEL at C-terminus | Universal in fungi | retrieval signal | ER |
| SEC12 | S. cerevisiae | COPII vesicle protein | ER/Golgi |
| SEC12 | A. niger | COPII vesicle protein | ER/Golgi |
| OCH1 | S. cerevisiae | 1,6-mannosyltransferase | Golgi (cis) |
| OCH1 | P. pastoris | 1,6-mannosyltransferase | Golgi (cis) |
| MNN9 | S. cerevisiae | 1,6-mannosyltransferase complex | Golgi |
| MNN9 | A. niger | undetermined | Golgi |
| VAN1 | S. cerevisiae | undetermined | Golgi |
| VAN1 | A. niger | undetermined | Golgi |
| ANP1 | S. cerevisiae | undetermined | Golgi |
| HOCI | S. cerevisiae | undetermined | Golgi |
| MNN10 | S. cerevisiae | undetermined | Golgi |
| MNN10 | A. niger | undetermined | Golgi |
| MNN11 | S. cerevisiae | undetermined | Golgi (cis) |
| MNN11 | A. niger | undetermined | Golgi (cis) |
| MNT1 | S. cerevisiae | 1,2-mannosyltransferase | Golgi (cis, medial) |
| KTR1 | P. pastoris | undetermined | Golgi (medial) |
| KRE2 | P. pastoris | undetermined | Golgi (medial) |
| KTR3 | P. pastoris | undetermined | Golgi (medial) |

TABLE 1-continued

Sources of useful compartmental targeting sequences

| Gene or Sequence | Organism | Function | Location of Gene Product |
|---|---|---|---|
| MNN2 | S. cerevisiae | 1,2-mannosyltransferase | Golgi (medial) |
| KTR1 | S. cerevisiae | undetermined | Golgi (medial) |
| KTR2 | S. cerevisiae | undetermined | Golgi (medial) |
| MNN1 | S. cerevisiae | 1,3-mannosyltransferase | Golgi (trans) |
| MNN6 | S. cerevisiae | Phosphomannosyltransferase | Golgi (trans) |
| 2,6 ST | H. sapiens | 2,6-sialyltransferase | trans Golgi network |
| UDP-Gal T | S. pombe | UDP-Gal transporter | Golgi |

Endomannosidase Fusion Constructs

A representative example of an endomannosidase fusion construct derived from a combinatorial DNA library of the invention inserted into a plasmid is pSH280, which comprises a truncated *Saccharomyces* MNN1(m) targeting peptide (1-303 nucleotides of MNN11 from SwissProt P46985), constructed from primers SEQ ID NO: 5 and SEQ ID NO: 6, ligated in-frame to a 48 N-terminal amino acid deletion of a rat endo-α1,2-mannosidase (Genbank AF 023657). The nomenclature used herein, thus, refers to the targeting peptide/catalytic domain region of a glycosylation enzyme as *Saccharomyces* MNN11(m)/rat endomannosidase Δ48. The encoded fusion protein localizes in the Golgi by means of the MNN111 targeting peptide sequence while retaining its endomannosidase catalytic domain activity and is capable of producing unglucosylated N-glycans such as Man$_4$GlcNAc$_2$ in a lower eukaryote. The glycan profile from a reporter glycoprotein K3 expressed in a strain of *P. pastoris* RDP25 (och1 alg3) transformed with pSH280 exhibits a peak, among others, at 1099 m/z [c] corresponding to the mass of Man$_4$GlcNAc$_2$ and 1424 m/z [a] corresponding to the mass of hexose 6 (FIG. 10B; see Examples 11 and 12). This new *P. pastoris* strain, designated as YSH97, shows greater than about 95% endomannosidase activity evidenced by the extent to which the glucosylated hexose 6 structure is removed from the reporter glycoprotein.

Figure 10A:
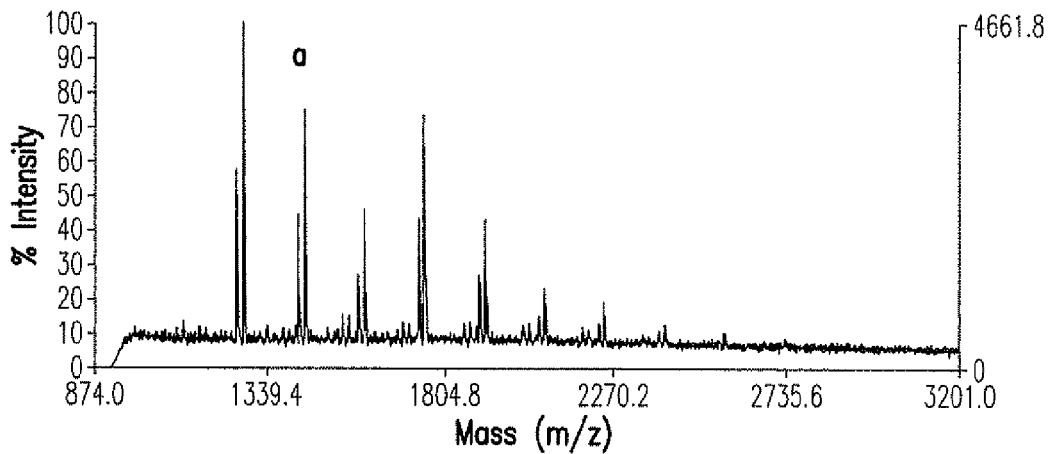
FIG. 10A shows a MALDI-TOF MS analysis of N-glycans isolated from a kringle 3 glycoprotein produced in *P. pastoris* RDP-25 (och1 alg3).
Figure 10B:
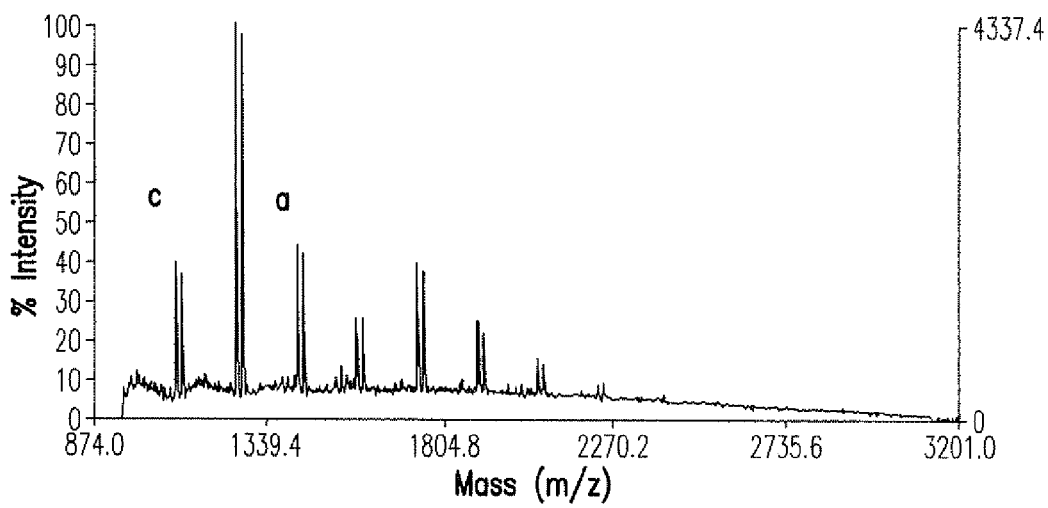
FIG. 10B shows a MALDI-TOF MS analysis of N-glycans isolated from a kringle 3 glycoprotein produced in *P. pastoris* RDP-25 (och1 alg3) transformed with pSH280 (rat endomannosidaseΔ48/Mnn11(m)) showing, a peak, among others, at 1099 m/z [c] corresponding to the mass of $Man_4GlcNAc_2$ and 1424 m/z [a] corresponding to the mass of hexose 6. This strain was designated as YSH97.

The structure of hexose 6 [a] expressed in a host cell (e.g., *P. pastoris* RDP25) comprises a mixture of glycans comprising GlcMan$_5$GlcNAc$_2$ and Man$_6$GlcNAc$_2$ and its isomers (FIG. 10A). By introduction and expression of the endomannosidase of the present invention in a host cell, a composition comprising at least one glucose residue and mannose residue is removed from the hexose 6 structure (FIG. 10B). The glucosylated structure GlcMan$_5$GlcNAc$_2$ is readily converted to Man$_4$GlcNAc$_2$, which is then subsequently converted to Man$_3$GlcNAc$_2$ with α1,2-mannosidase in vitro digestion. The hexose 6 species comprising the glucosylated mannans is not cleaved by α1,2-mannosidase. The predominant peak corresponding to the structure Man$_3$GlcNAc$_2$ [b] (FIG. 10C) shown after the α1,2-mannosidase digestion confirms the apparent removal of the glucose-mannose dimer from GlcMan$_5$GlcNAc$_2$ exposing a terminal Manα1,2 on Man$_4$GlcNAc$_2$ for hydrolysis producing Man$_3$GlcNAc$_2$.

Figure 10C:
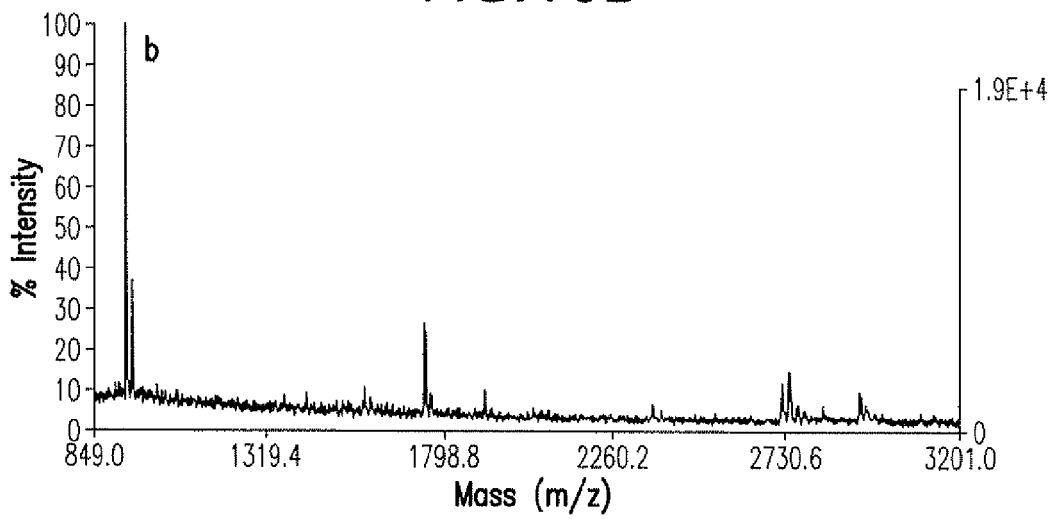
FIG. 10C shows a MALDI-TOF MS analysis of N-glycans isolated from a kringle 3 glycoprotein produced in *P. pastoris* YSH97 after in vitro digestion with α1,2-mannosidase, exhibiting a peak at 938 m/z [b] ($Na^+$ adduct) corresponding to the mass of $Man_3GlcNAc_2$.

The other species of hexose 6: Man$_6$GlcNAc$_2$ is not readily affected by the endomannosidase of the present invention and accordingly, is contemplated as un-glucosylated structures. A skilled artisan would appreciate that this species of hexose 6: Man$_6$GlcNAc$_2$ comprises Manα1,2 additions, which is evidenced by the subsequent α1,2-mannosidase in vitro digestion producing Man$_3$GlcNAc$_2$ (FIG. 10C).

Another example of an endomannosidase fusion construct derived from a combinatorial DNA library of the invention inserted into a plasmid is pSH279, which is a truncated *Saccharomyces* VAN1(s) targeting peptide (1-279 nucleotides of VAN1 from SwissProt P23642) constructed from primers SEQ ID NO: 7 and SEQ ID NO: 8, ligated in-frame to a 48 N-terminal amino acid deletion of a rat endo-α1,2-mannosidase (Genbank AF 023657). The nomenclature used herein, thus, refers to the targeting peptide/catalytic domain region of a glycosylation enzyme as *Saccharomyces* VAN1(s)/rat endomannosidase Δ48. The encoded fusion protein localizes in the Golgi by means of the VAN1 targeting peptide sequence while retaining its endomannosidase catalytic domain activity and is capable of producing N-glycans having a Man$_4$GlcNAc$_2$ structure in *P. pastoris* (RDP25). The glycan profile from a reporter glycoprotein K3 expressed in a strain of *P. pastoris* RDP-25 (och1 alg3) transformed with pSH279 exhibits a peak, among others, at 1116 m/z [c] corresponding to the mass of Man$_4$GlcNAc$_2$ and 1441 m/z [a] corresponding to the mass of hexose 6 (FIG. 11; examples 11 and 12). FIG. 11B shows a residual hexose 6 [a] peak indicating only partial activity of the endomannosidase. This strain, designated as YSH96, shows greater than about 40% endomannosidase activity, evidenced by the extent to which the glucosylated hexose 6 structure is removed from the reporter glycoprotein.

Figure 11A:
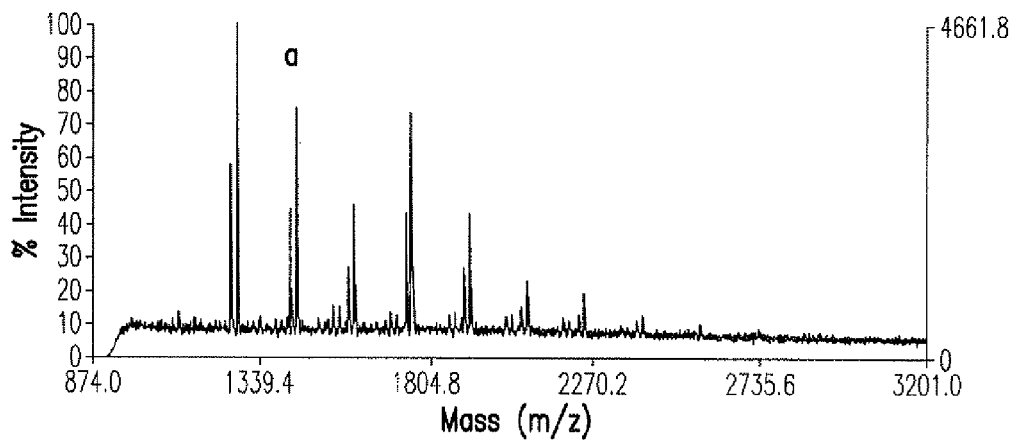
FIG. 11A shows a MALDI-TOF MS analysis of N-glycans isolated from a kringle 3 glycoprotein produced in *P. pastoris* RDP-25 (och1 alg3).
Figure 11B:
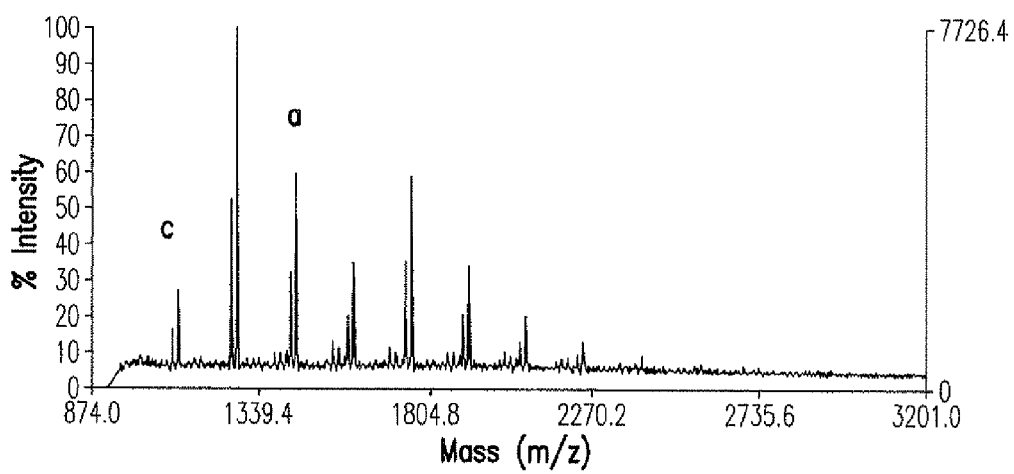
FIG. 11B shows a MALDI-TOF MS analysis of N-glycans isolated from a kringle 3 glycoprotein produced in *P. pastoris* RDP-25 (och1 alg3) transformed with pSH279 (rat endomannosidaseΔ48/Van1(s)) showing among others, a peak at 1116 m/z [c] corresponding to the mass of $Man_4GlcNAc_2$ and 1441 m/z [a] corresponding to the mass of hexose 6. This strain was designated YSH96.

The structure of hexose 6 [a] expressed in a host cell (e.g., *P. pastoris* RDP25) comprises a mixture of glycans comprising GlcMan$_5$GlcNAc$_2$ and Man$_6$GlcNAc$_2$ and its isomers (FIG. 11A). By introduction and expression of the endomannosidase of the present invention in a host cell, a composition comprising at least one glucose residue and mannose residue is removed from the hexose 6 structure (FIG. 11B). The glucosylated structure GlcMan$_5$GlcNAc$_2$ is readily converted to Man$_4$GlcNAc$_2$, which is then subsequently converted to Man$_3$GlcNAc2 with α1,2-mannosidase in vitro digestion. The hexose 6 species comprising the glucosylated mannans is not cleaved by α1,2-mannosidase. The predominant peak corresponding to the structure Man$_3$GlcNAc$_2$ [b] (FIG. 11C) shown after the α1,2-mannosidase digestion confirms the apparent removal of the glucose-mannose dimer from GlcMan$_5$GlcNAc$_2$ exposing a terminal Manα1,2 on Man$_4$GlcNAc$_2$ for hydrolysis producing Man$_3$GlcNAc$_2$.

Figure 11C:
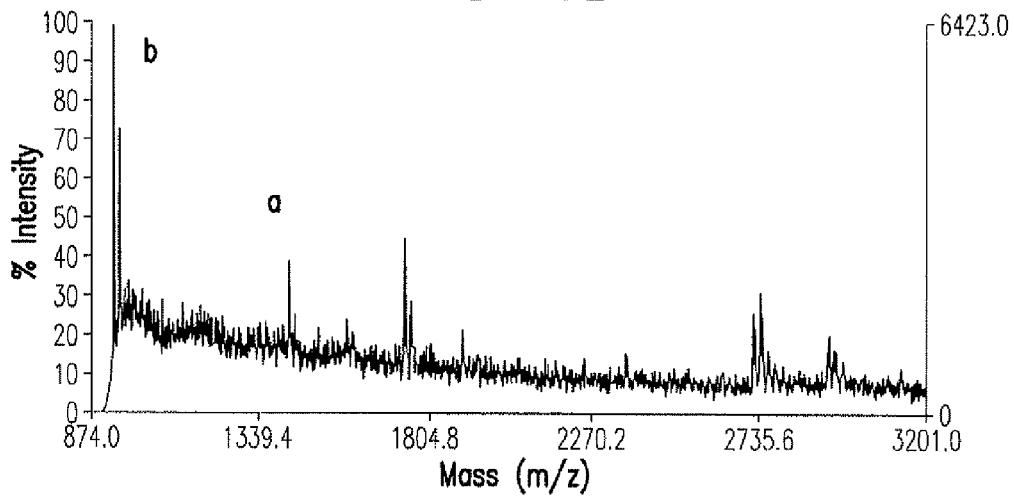
FIG. 11C shows a MALDI-TOF MS analysis of N-glycans isolated from a kringle 3 glycoprotein produced in *P. pastoris* YSH96 after in vitro digestion with α1,2-mannosidase, exhibiting a peak at 938 m/z [b] ($Na^+$ adduct) corresponding to the mass of $Man_3GlcNAc_2$ and a second peak at 1425 m/z [a] showing a decrease in hexose 6.

The other species of hexose 6: Man$_6$GlcNAc$_2$ is not readily affected by the endomannosidase of the present invention and accordingly, is contemplated as un-glucosylated structures. A skilled artisan would appreciate that this species of hexose 6: Man$_6$GlcNAc$_2$ comprises Manα1,2 additions, which is evidenced by the subsequent α1,2-mannosidase in vitro digestion producing Man$_3$GlcNAc$_2$ (FIG. 11C).

Figure 12A:
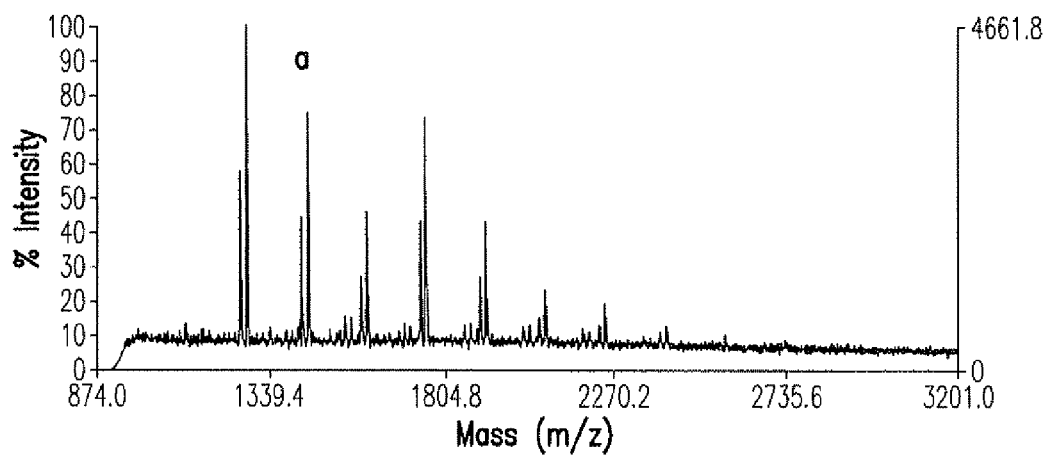
FIG. 12A shows a MALDI-TOF MS analysis of N-glycans isolated from a kringle 3 glycoprotein produced in *P. pastoris* RDP-25 (och1 alg3).
Figure 12B:
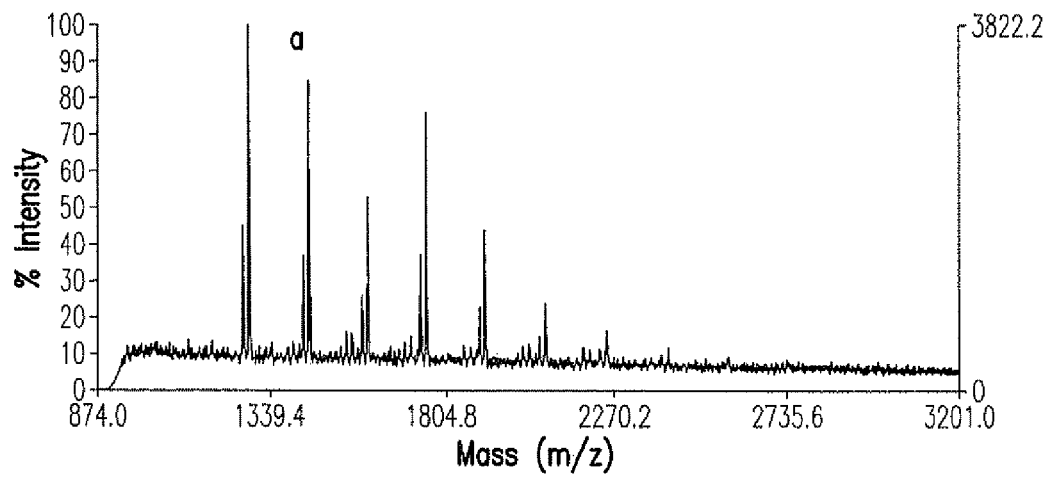
FIG. 12B shows a MALDI-TOF MS analysis of N-glycans isolated from a kringle 3 glycoprotein produced in *P. pastoris* RDP-25 (och1 alg3) transformed with pSH278 (rat endomannosidaseΔ48/Gls1(s)) showing, a peak, among others, at 1439 m/z ($K^+$ adduct) [c] and a peak at 1422 m/z ($Na^+$ adduct) corresponding to the mass of hexose 6 [a]. This strain was designated YSH95.
Figure 12C:
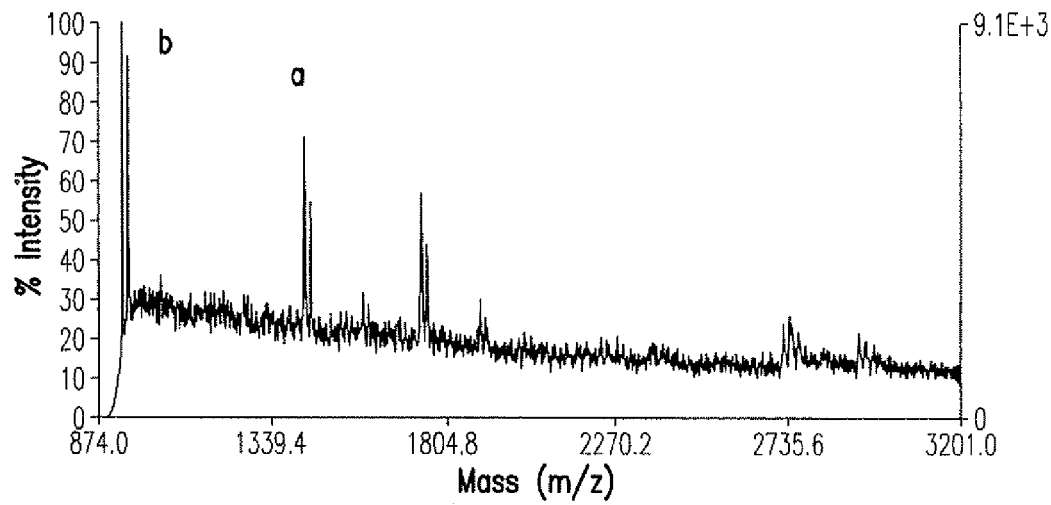
FIG. 12C shows a MALDI-TOF MS analysis of N-glycans isolated from a kringle 3 glycoprotein produced in *P. pastoris* YSH95 after in vitro digestion with α1,2-mannosidase, exhibiting a peak at 936 m/z [b] ($Na^+$ adduct) corresponding to the mass of $Man_3GlcNAc_2$ and a peak at 1423 m/z [a] showing a decrease in hexose 6.

Additionally, an example of an endomannosidase fusion construct inserted into a plasmid that does not show apparent catalytic activity derived from a combinatorial DNA library of the invention is pSH278, which a truncated *Saccharomyces* GLS1(s) targeting peptide (1-102 nucleotides of GLS1from SwissProt P53008) constructed from primers SEQ ID NO: 9 and SEQ ID NO: 10, ligated in-frame to a 48 N-terminal amino acid deletion of a rat endo-α1,2-mannosidase (Genbank AF 023657). The nomenclature used herein, thus, refers to the targeting peptide/catalytic domain region of a glycosylation enzyme as *Saccharomyces* GLS1(s)/rat endomannosidase Δ48. The glycan profile from a reporter glycoprotein K3 expressed in a strain of a *P. pastoris* RDP-25 (och1 alg3) transformed with pSH278 exhibits, a peak, among others, at 1439 m/z ($K^+$ adduct) [c] and a peak at 1422 m/z ($Na^+$ adduct) corresponding to the mass of hexose 6 [a] (FIG. 12; examples 11 and 12). This strain, designated as YSH95, shows less than about 10% endomannosidase activity as evidenced by the extent to which the glucosylated hexose 6 structure is removed from the reporter glycoprotein.

Unlike the previous two glycan profiles shown in FIGS. 10 and 11, the endomannosidase construct pSH278 expressed in *P. pastoris* RDP25 shows relatively low endomannosidase activity (FIG. 12). Subsequent digestion with α1,2 mannosidase, however, reveals a peak corresponding to the mass of $Man_3GlcNAc_2$ [b]. A skilled artisan would appreciate that the hexose 6 species comprising $Man_6GlcNAc_2$ have been converted to $Man_3GlcNAc_2$ by introduction of α1,2 mannosidase whereas the other hexose 6 species comprising $GlcMan_5GlcNAc_2$ are still present, which, in effect, are still glucosylated.

By creating a combinatorial DNA library of these and other such endomannosidase fusion constructs according to the invention, a skilled artisan may distinguish and select those constructs having optimal intracellular endomannosidase trimming activity from those having relatively low or no activity. Methods using combinatorial DNA libraries of the invention are advantageous because only a select few endomannosidase fusion constructs may produce a particularly desired N-glycan in vivo. In addition, endomannosidase trimming activity may be specific to a particular protein of interest. Thus, it is to be further understood that not all targeting peptide/mannosidase catalytic domain fusion constructs may function equally well to produce the proper glycosylation on a glycoprotein of interest. Accordingly, a protein of interest may be introduced into a host cell transformed with a combinatorial DNA library to identify one or more fusion constructs which express a mannosidase activity optimal for the protein of interest. One skilled in the art will be able to produce and select optimal fusion construct(s) using the combinatorial DNA library approach described herein.

It is apparent, moreover, that other such fusion constructs exhibiting localized active endomannosidase catalytic domains may be made using techniques such as those exemplified in WO 02/00879 and described herein. It will be a matter of routine experimentation for one skilled in the art to make and use the combinatorial DNA library of the present invention to optimize non-glucosylated N-glycans (for example $Man_4GlcNAc_2$) production from a library of fusion constructs in a particular expression vector introduced into a particular host cell.

Recombinant Expression of Genes Encoding Endomannosidase

Another feature of the invention is the recombinant expression of the nucleic acid sequences encoding the endomannosidase. The nucleic acid sequences are operatively linked to an expression control sequence in an appropriate expression vector and transformed in an appropriate host cell (Example 3). A wide variety of suitable vectors readily available in the art are used to express the fusion constructs of the present invention in a variety of host cells. The vectors pSH278, pSH279 and pSH280 (Example 4) are a select few examples described herein suitable for expression of endomannosidase activity in a lower eukarote, *Pichia pastoris*. It is to be understood that a wide variety of vectors suitable for expression of endomannosidase activity in a selected host cell are encompassed within the present invention.

In one aspect of the invention, a lower eukaryotic host cell producing glucosylated high mannose structures is modified by introduction and expression of the endomannosidase of the present invention. For example, a host cell *P. pastoris* RDP25 (och1 alg3) producing hexose 6 is modified by introduction and expression of the endomannosidase of the present invention. The host cell of the present invention produces a modified glycan converting $GlcMan_5GlcNAc_2$ to $Man_4GlcNAc_2$. Accordingly, in one embodiment, a lower eukaryotic host cell expressing the endomannosidase of the present invention catalyzes the removal of a molecule comprising at least one glucose residue and a mannose residue.

The activity of the recombinant nucleic acid molecules encoding the endomannosidase of the invention are described herein. Varied expression levels are quantified by the conversion of a glucosylated glycan $GlcMan_5GlcNAc_2$ to a deglucosylated glycan $Man_4GlcNAc_2$. In one embodiment, the conversion of $GlcMan_5GlcNAc_2$ to $Man_4GlcNAc_2$ is partial (FIG. 10, 11).

In another embodiment, the conversion of $GlcMan_5GlcNAc_2$ to $Man_4GlcNAc_2$ is complete. In a preferred embodiment, at least 30% of $GlcMan_5GlcNAc_2$ is converted to $Man_4GlcNAc_2$. In a more preferred embodiment, at least 60% of $GlcMan_5GlcNAc_2$ is converted to $Man_4GlcNAc_2$. In an even more preferred embodiment, at least 90% of $GlcMan_5GlcNAc_2$ is converted to $Man_4GlcNAc_2$. Furthermore, it is contemplated that other glucose containing glycans are removed by the endomannosidase of the present invention. For example, the endomannosidase of the present invention further comprises the activity of truncating a glycan $Glc_{1-3}Man_{9-5}GlcNAc_2$ to $Man_{8-4}GlcNAc_2$.

Additionally, a gene encoding a catalytically active endomannosidase is expressed in a lower eukaryotic host cell (e.g. *Pichia pastoris*) modifying the glycosylation on a protein of interest. In one embodiment, the endomannosidase of the present invention modifies glucosylated N-linked oligosaccharides on a protein of interest. The resulting protein produces a more human-like glycoprotein. A lower eukaryotic host cell modified by the endomannosidase of the invention produces a $Man_{8-4}GlcNAc_2$ glycoform from a glucosylated glycoform on a protein of interest (FIG. 2). For example, a strain of *P. pastoris* modified by the endomannosidae of the invention produces a $Man_4GlcNAc_2$ glycoform and decreased moiety of the glucosylated hexose 6 glycoform on a protein of interest (FIG. 10B). Subsequent α1,2-mannosidase digestion of the $Man_4GlcNAc_2$ glycoform results in a trimannosyl core (FIG. 10C). Accordingly, the present invention provides a catalytically active endomannosidase in a lower eukaryotic host cell that converts a glucosylated glycoform to a desired glycoform on a therapeutic protein of interest.

Therapeutic proteins are typically administered by injection, orally, pulmonary, or other means. Examples of suitable target glycoproteins which may be produced according to the invention include, without limitation: erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin and α-feto proteins.

Promoters

In another aspect of the invention, the rat liver endomannosidase (Genbank gi:2642186), the human endomannosidase (Genbank gi:20547442) or the mouse mannosidase (Genbank AK030141) is cloned into a yeast integration plasmid under the control of a constitutive promoter to optimize the amount of endomannosidase activity while restricting adverse effects on the cell. This involves altering promoter strength and optionally includes using an inducible promoter to better control the expression of these proteins.

In addition to expressing the wild-type endomannosidase, modified forms of the endomannosidase are expressed to enhance cellular localization and activity. Varying lengths of the catalytic domain of endomannosidase is fused to endogenous yeast targeting regions as described in WO 02/00879. The catalytically active fragment encoding the endomannosidase genes are cloned into a yeast integration plasmid under the control of a constitutive promoter. This involves altering the promoter strength and may include using an inducible promoter to better control the expression of these proteins. Furthermore, to increase enzyme activity, the protein is mutated to generate new characteristics. The skilled artisan recognizes the routine modifications of the procedures disclosed herein may provide improved results in the production of unglucosylated glycoprotein of interest.

Codon Optimization

It is also contemplated that the nucleic acids of the present invention may be codon optimized resulting in one or more changes in the primary amino acid sequence, such as a conservative amino acid substitution, addition, deletion or combination thereof.

Secreted Endomannosidase

In another feature of the invention, a soluble secreted endomannosidase is expressed in a host cell. In a preferred embodiment, a soluble mouse or human endomannosidase is recombinantly expressed. A soluble endomannosidase lacks cellular localization signal that normally localizes to the Golgi apparatus or bind to the cell membrane. Expression of the catalytic domain of the endomannosidase to produce a soluble recombinant enzyme, which lacks the transmembrane domain, can be fused in-frame to a second domain or a tag that facilitates its purification. The secreted rat and human endomannosidase of the present invention from $P.$ $pastoris$ is shown in FIG. 9 (Example 8).

Expressed endomannosidase is particularly useful for in vitro modification of glucosylated glycan structures. In a more preferred embodiment, the recombinant endomannosidase is used to produce unglucosylated glycan intermediates in large scale glycoprotein production. FIG. 13 shows the activity of the rat (FIG. 13B) and human (FIG. 13C) endomannosidase that have cleaved the glucose-α1,3-mannose dimer on the glycan intermediate GlcMan$_5$GlcNAc$_2$ converting it to Man$_4$GlcNAc$_2$. (See FIG. 14). Accordingly, the endomannosidase of the present invention is used to modify glucosylated glycans in vitro. In addition, such soluble endomannosidase are purified according to methods well-known in the art.

Figure 14:
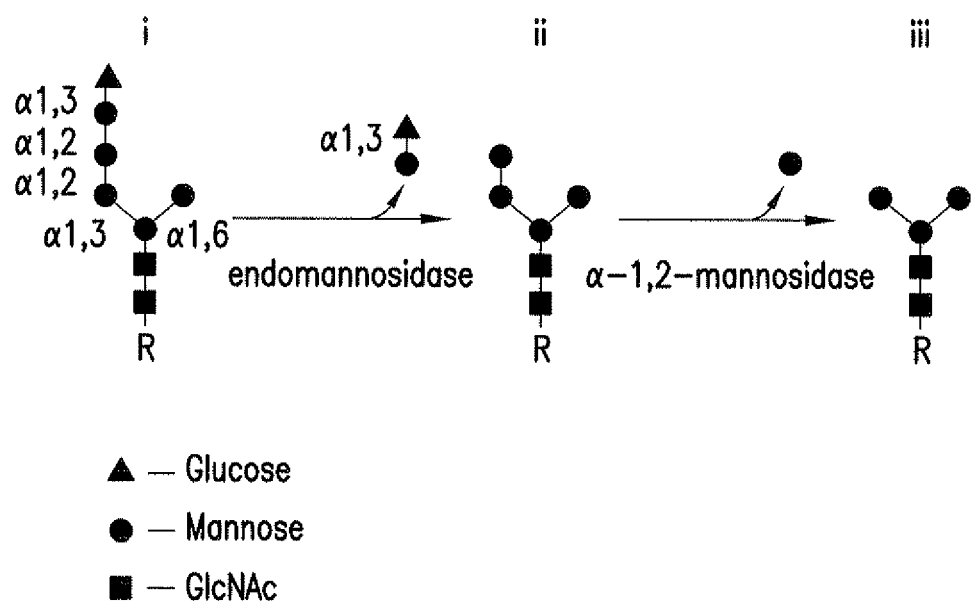
FIG. 14 represents substrate glycan modification by endomannosidase and subsequent confirmation of product structure by α1,2-mannosidase digestion and analysis. Structures illustrated are GlcMan$_5$GlcNAc$_2$ (i), Man$_4$GlcNAc$_2$ (ii) and Man$_3$GlcNAc$_2$ (iii). R represents the reducing terminus of the glycan. The substrate GlcMan$_5$GlcNAc$_2$ (i) is modified by an endomannosidase converting it to Man$_4$GlcNAc$_2$ (ii) (hydrolyzing Glcα1,3Man). Subsequent α1,2-mannosidase digestion results in Man$_3$GlcNAc$_2$ (iii).

The secreted endomannosidases converts glucosylated structures (e.g., GlcMan$_5$GlcNAc$_2$) FIG. 14($i$) to deglucosylated structures (e.g., Man$_4$GlcNAc$_2$) FIG. 14($ii$) by hydrolyzing at least one glucose residue and one mannose residue on an oligosaccharide. For example, a glucose-α1,3-mannose dimer is cleaved from the glucosylated oligosaccharide by the endomannosidase as shown in FIG. 14. Subsequent α1,2-mannosidase digestion FIG. 14($iii$) results in the structure: Man$_3$GlcNAc$_2$ indicating an additional Manα1,2 on the trimannosyl core.

Host Cells

A number of host cells can be used to express the endomannosidase of the present invention. For example, the endomannosidase can be expressed in mammalian, plant, insect, fungal, yeast, algal or bacterial cells. For the modification of glucosylation on a protein of interest, preferred host cells are lower eukaryotes producing Glc$_{1-3}$Man$_{9-5}$GlcNAc$_2$ structures. Additionally, other host cells producing a mixture of glucosylated glycans are selected. For example, a host cell (e.g., $P.$ $pastoris$ RDP25) producing the glucosylated structures such as GlcMan$_5$GlcNAc$_2$ in addition to unglucosylated structures such as Man$_6$GlcNAc$_2$ and its isomers is selected.

Preferably, a lower eukaryotic host cell is selected from the group consisting of $Pichia$ $pastoris$, $Pichia$ $finlandica$, $Pichia$ $trehalophila$, $Pichia$ $koclamae$, $Pichia$ $membranaefaciens$, $Pichia$ $opuntiae$, $Pichia$ $thermotolerans$, $Pichia$ $salictaria$, $Pichia$ $guercuum$, $Pichia$ $pijperi$, $Pichia$ $stiptis$, $Pichia$ $methanolica$, $Pichia$ sp., $Saccharomyces$ $cerevisiae$, $Saccharomyces$ sp., $Hansenula$ $polymorpha$, $Kluyveromyces$ sp., $Kluyveromyces$ $lactis$, $Candida$ $albicans$, $Aspergillus$ $nidulans$, $Aspergillus$ $niger$, $Aspergillus$ $oryzae$, $Trichoderma$ $reesei$, $Chrysosporium$ $lucknowense$, $Fusarium$ sp., $Fusarium$ $gramineum$, $Fusarium$ $venenatum$ and $Neurospora$ $crassa$.

Other hosts may include well-known eukaryotic and prokaryotic hosts, such as strains of $E.$ $coli$, $Pseudomonas$, $Bacillus$, $Streptomyces$, and animal cells, such as Chinese Hamster Ovary (CHO; e.g., the alpha-glucosidase I deficient strain Lec-23), R1.1, B-W and L-M cells, African Green Monkey kidney cells (e.g., COS 1, COS-7, BSC1, BSC40, and BMT10), insect cells (e.g., Sf9), and human cells (e.g., HepG2) and plant cells in culture.

Methods for Modifying Glucosylated N-Glycans

In another aspect of the invention, herein is provided a method for modifying the glucosylated glycans by introducing and expressing the endomannosidase of the present invention. FIG. 1, as highlighted, shows the endomannosidase cleavage of the mono-, di-, and tri-glucosylated glycans, represented by the second and third glucose residues. Accordingly, the endomannosidase enzyme of the present invention is introduced into the Golgi of host (e.g. yeast) to enhance the efficiency of deglucosylation, and thus enhancing subsequent trimming of the mannan structure prior to the addition of further sugars to produce a more human-like N-linked glycosylation structure (FIG. 2).

In a further aspect of the invention, introduction of the endomannosidase into the Golgi (e.g. yeast) provides a method of recovering glucosylated glycoproteins that have entered the Golgi and are thus no longer accessible to the ER glucosidase I and II enzymes. The endomannosidase of the present invention can process such glucosylated structures; for example, Glc$_{1-3}$Man$_{9-5}$GlcNAc$_2$ to Man$_{8-4}$GlcNAc$_2$, highlighted by the four mannose residues as shown in FIG. 2.

Accordingly, the present invention provides a quality control mechanism wherein the recovered glucosylated oligosaccharides are deglucosylated.

Moreover, it is contemplated that the use of the endomannosidase obviates the need for the glucosidase I and II enzymes required in the early steps of glycan trimming. In one embodiment, a host cell of the present invention may be deficient in glucosidase I and/or II activity. In the absence of glucosidase I or II activities, a host cell of the present invention may still exhibit a glucose catalyzing activity through the endomannosidase. Accordingly, herein is provided a method of introducing a nucleic acid encoding an endomannosidase into a host (e.g. yeast), upon expression, modifies glucosylated glycoproteins that have entered the Golgi, which are are no longer accessible to the ER glucosidase I and glucosidase II enzymes. Preferably, the nucleic acid encoding the enzyme of the present invention cleaves a composition comprising at least one glucose residue and one mannose residue linked to an oligosaccharide (FIG. 2). More preferably, a Glcα1,3Man dimer, Glc$_2$α1,3Man trimer or Glc$_3$α1,3Man tetramer are cleaved according to the method of the present invention.

It will be a matter of routine experimentation for one skilled in the art to use the method described herein to optimize production of deglucosylated glycans (e.g. Man4GlcNAc$_2$) using a selected fusion construct in a particular expression vector and host cell line. Accordingly, routine modifications can be made in the lower eukaryotic host cell expressing the endomannosidase of the present invention, which converts glucosylated glycans to deglucosylated glycans (e.g. Man$_4$GlcNAc$_2$) and subsequently to a desired intermediate for the production of therapeutic glycoproteins.

Introduction of Other Glycosylation Enzymes in Host Cells

Additionally, a set of modified glycosylation enzymes are introduced into host cells to enhance cellular localization and activity in producing glycoproteins of interest. This involves the fusion of varying lengths of the catalytic domains to yeast endogenous targeting regions as described in WO 02/00879. In one embodiment, a host cell P. pastoris YSH97 (och1 alg3 endmannosidase) is modified by introduction and expression of glycosylation enzymes or catalytically active fragment thereof selected from the group consisting of α1,2-mannosidase I and II, GnT I (N-acetylglucosaminyltransferase I), GnT II, GnT III, GnT IV, GnT V, GnT VI, galactosyltransferase, sialyltransferase and fucosyltransferase. Similarly, the enzymes' respective transporters and their substrates (e.g. UDP-GlcNAc, UDP-Gal, CMP-NANA) are introduced and expressed in the host cells. See WO 02/00879.

Endomannosidase pH Optimum

Figure 15:
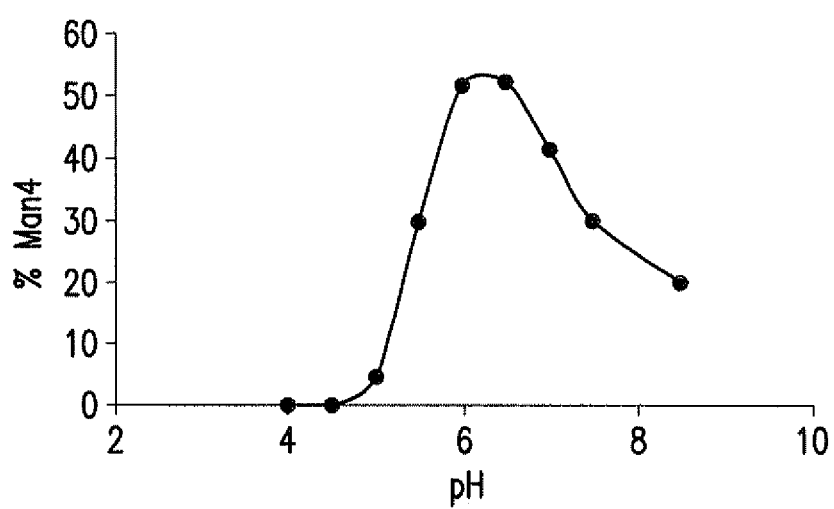
FIG. 15 shows a pH profile of the activity of human endomannosidase, indicated as % of GlcMan$_5$GlcNAc$_2$ substrate converted to Man$_4$GlcNAc$_2$ as a function of pH.

In another aspect of the invention, the encoded endomannosidase has a pH optimum between about 5.0 and about 8.5, preferably between about 5.2 and about 7.2 and more preferably about 6.2. In another embodiment, the encoded enzyme is targeted to the endoplasmic reticulum, the Golgi apparatus or the transport vesicles between ER, Golgi or the trans Golgi network of the host organism, where it removes glucosylated structures present on oligosaccharides. FIG. 15 shows a pH optimum profile of the human endomannosidase (SEQ ID NO:2) (Example 9).

The following are examples which illustrate the compositions and methods of this invention. These examples should not be construed as limiting: the examples are included for the purposes of illustration only.

EXAMPLE 1

Strains, Culture Conditions, and Reagents

Escherichia coli strains TOP10 or DH5α were used for recombinant DNA work. Protein expression in yeast strains were carried out at room temperature in a 96-well plate format with buffered glycerol-complex medium (BMGY) consisting of 1% yeast extract, 2% peptone, 100 mM potassium phosphate buffer, pH 6.0, 1.34% yeast nitrogen base, 4×10$^{-5}$% biotin, and 1% glycerol as a growth medium. The induction medium was buffered methanol-complex medium (BMMY) consisting of 1.5% methanol instead of glycerol in BMGY. Minimal medium is 1.4% yeast nitrogen base, 2% dextrose, 1.5% agar and 4×10$^{-5}$% biotin and amino acids supplemented as appropriate. Restriction and modification enzymes were from New England BioLabs (Beverly, Mass.). Oligonucleotides were obtained from the Dartmouth College Core facility (Hanover, N.H.) or Integrated DNA Technologies (Coralville, Iowa). MOPS, sodium cacodylate, manganese chloride were from Sigma (St. Louis, Mo.). Trifluoroacetic acid (TFA) was from Sigma/Aldrich, Saint Louis, Mo. The enzymes N-glycosidase F, mannosidases, and oligosaccharides were obtained from Glyko (San Rafael, Calif.). DEAE ToyoPearl resin was from TosoHaas. Metal chelating "His-Bind" resin was from Novagen (Madison, Wiss.). 96-well lysate-clearing plates were from Promega (Madison, Wis.). Protein-binding 96-well plates were from Millipore (Bedford, Mass.). Salts and buffering agents were from Sigma (St. Louis, Mo.). MALDI matrices were from Aldrich (Milwaukee, Wiss.).

EXAMPLE 2

Cloning of Human and Mouse Endomannosidases

As a positive control, we amplified the region homologous to the putative catalytic domain of the rat mannosidase gene using specific primers 5'-gaattcgccaccatggatttccaaaagagtgacagaatcaacag-3' (SEQ ID NO: 11) and 5'-gaattccagaaacaggcagctggcgatc-3' (SEQ ID NO: 12) and subcloned the resultant region into a yeast integration plasmid using standard recombinant DNA techniques (See, e.g., Sambrook et al. (1989) *Molecular Cloning, A Laboratory Manual* (2$^{nd}$ ed.), Cold Spring Harbor Laboratory, Cold Spring Harbor, N.Y. and references cited therein, all incorporated reference; see also Example 3).

To identify the sequence of and isolate the ORF of the human endomannosidase, we performed a protein BLAST search using the rat endomannosidase protein sequence (Genbank gi:2642187) and identified a hypothetical human protein (Genbank gi:20547442) of 290 amino acids in length which shows 88% identity and 94% similarity to amino acids 162 to 451 of the rat ORF (FIG. 3A). The DNA 5'-terminus of this human sequence was analyzed using translated BLAST and another hypothetical human protein (Genbank gi:18031878) was identified that possessed 95% identity over the first 22 amino acids of the search sequence but then terminates in a stop codon (FIG. 3B). Reading-frame analysis of this second sequence indicated that 172 amino acids were in-frame upstream of the homologus region (FIG. 3C). Combining both these 5' and 3' regions produced a putative sequence with an ORF of 462 amino acids (FIG. 4) and a predicted molecular mass of 54 kDa.

To confirm that the two human sequences are one entire ORF, we designed primers specific to the 5'-terminus of the gi:18031877 ORF and the 3'-terminus of the gi: 20547441

ORF (5'-atggcaaagtttcggagaaggacttgc-3' (SEQ ID NO: 13) and 5'-ttaagaaacaggcagctggcgatctaatgc-3' (SEQ ID NO: 14) respectively). These primers were used to amplify a 1389 bp fragment from human liver cDNA (Clontech, Palo Alto, Calif.) using Pfu Turbo DNA polymerase (Stratagene, La Jolla, Calif.) as recommended by the manufacturers, under the cycling conditions: 95° C. for 1 min, 1 cycle: 95° C. for 30 sec, 60° C. for 1 min, 72° C. for 2.5 min, 30 cycles; 72° C. for 5 min, 1 cycle. The DNA fragment produced was incubated with Taq DNA polymerase for 10 min at 68° C. and TOPO cloned into pCR2.1 (Invitrogen, Carlsbad, Calif.). ABI DNA sequencing confirmed that both of the human sequences identified by BLAST searching produced one complete ORF, this confirmed construct was named pSH131.

The endomannosidase gene from mouse may be similarly amplified and isolated. (See also, e.g., Sambrook et al. (1989) *Molecular Cloning, A Laboratory Manual* ($2^{nd}$ ed.), Cold Spring Harbor Laboratory, Cold Spring Harbor, N.Y., Innis et al. (1990) *PCR Protocols: A Guide to Methods and Applications*, Academic Press, New York, N.Y. and references cited therein, all incorporated reference). The primers 5'-atggcaaaatttcgaagaaggacctgcatc-3' mEndo forward (SEQ ID NO: 15) and 5'-ttatgaagcaggctgctgttgatccaatgc-3' mEndo reverse (SEQ ID NO: 16) are used to generate the mouse full-length endomannosidase open reading frame.

EXAMPLE 3

Generation of Recombinant Endomannosidase Constructs and Expression

To generate a yeast secreted form of the human endomannosidase, a region encoding the putative catalytic domain was expressed in the EasySelect *Pichia* Expression kit (Invitrogen) as recommended by the manufacturer. Briefly, PCR was used to amplify the ORF fragment from 178 to 1386 bases from pSH131 using the primers hEndo Δ59 forward and hEndo Δstop reverse (5'-gaattcgccaccatggatttccaaaagagtgacagaatcaacag-3' (SEQ ID NO: 11) and 5'-gaattccagaaacaggcagctggcgatc-3' (SEQ ID NO: 12), respectively, with an EcoRI restriction site engineered into each). The conditions used with Pfu Turbo were: 95° C. for 1 min, 1 cycle; 95° C. for 30 sec, 55° C. for 30 sec, 72° C. for 3 min, 25 cycles; 72° C. for 3 min, 1 cycle. The product was incubated with Taq DNA polymerase, TOPO cloned and ABI sequenced as described above. The resulting clone was designated pSH178. From this construct, the human endomannosidase fragment was excised by digestion with EcoRI and subcloned into pPicZαA (Invitrogen, Carlsbad, Calif.) digested with the same enzyme, producing pAW105. This construct was transformed into the *Pichia pastoris* yeast strain GS115 supplied with the EasySelect *Pichia* Expression kit (Invitrogen, Carlsbad, Calif.), producing the strain YSH16. Subsequently, the strain was grown in BMGY to an $OD_{600}$ of 2 and induced in BMMY for 48 h at 30° C., as recommended by the kit manufacturers.

To confirm that the isolated ORF was an endomannosidase, the previously reported rat liver endomannosidase was amplified and expressed in parallel as a positive control. Briefly, the fragment encoding amino acids 49 to 451 of the rat endomannosidase, corresponding to the putative catalytic domain, was amplified from rat liver cDNA (Clontech) using the same conditions as described for the human endomannosidase above. The primers used were rEndo Δ48 forward and rEndo Δstop reverse (5'-gaattcgccaccatggacttccaaag-gagtgatcgaatcgacatgg-3' (SEQ ID NO: 17) and 5'-gaattcct-gaagcaggcagagttgatcc-3' (SEQ ID NO: 18), respectively, with an EcoRI restriction site engineered into each). The PCR product was cloned into pCR2.1, sequenced and the resultant construct named pSH179. Subsequently, the rat endomannosidase was subcloned into pPicZαA (Invitrogen, Carlsbad, Calif.) and expressed in GS115 (Invitrogen, Carlsbad, Calif.) as described above, producing pAW106 and YSH13.

To N-terminal tag recombinant human and rat endomannosidases, a double FLAG tag was engineered 3' to the Kex2 cleavage site of the alpha mating factor and 5' to the EcoRI restriction used for endomannosidase cloning in pPicZαA, as follows. Briefly, the phosphorylated oligonucleotides FLAG tag forward and FLAG tag reverse (5'-P-aatttatggactacaag-gatgacgacgacaagg-3' (SEQ ID NO: 19) and 5'-P-aattcct-tgtcgtcgtcatccttgtagtccata-3' (SEQ ID NO: 20)) were annealed as described in Sambrook et al. (1989), supra, and ligated into pPicZαA digested with EcoRI and dephosphorylated with calf alkaline phosphatase. A construct containing two tandem FLAG tags in the correct orientation was named pSH241. Subsequently, rat and human endomannosidases were digested from pSH179 and pSH178 with EcoRI and ligated into pSH241, digested with the same enzyme. The resultant rat and human endomannosidase constructs were named pSH245 and pSH246, respectively. Transformation of these constructs into GS115 (Invitrogen, Carlsbad, Calif.) produced the strains YSH89 and YSH90, respectively. Expression of endomannosidase activities in these strains was studied as described above.

EXAMPLE 4

Expression of Rat Endomannosidases in *P. pastoris*

The catalytic domain of rat endomannosidase was amplified from pSH179 using the primers rat Endomannosidase Δ48 AscI and rEndo PacI (5'-ggcgcgccgacttccaaaggagtgatc-gaatcgacatgg-3' (SEQ ID NO: 21) and 5'-ccttaattaattatgaag-caggcagctgttgatccaatgc-3' (SEQ ID NO: 22), encoding AscI and PacI restriction sites respectively). These primers were used to amplify a 1212 bp fragment from pSH179 using Pfu Turbo DNA polymerase (Stratagene) as recommended by the manufacturers, under the cycling conditions: 95° C. for 1 min, 1 cycle: 95° C. for 30 sec, 60° C. for 1 min, 72° C. for 2.5 min, 30 cycles; 72° C. for 5 min, 1 cycle. The DNA fragment produced was incubated with Taq DNA polymerase for 10 min at 68° C. and TOPO cloned into pCR2.1 (Invitrogen, Carlsbad, Calif.). ABI DNA sequencing confirmed that both of the human sequences identified by BLAST searching produced one complete ORF. This confirmed construct was named pSH223. Subsequently, the rat endomannosidase fragment was digested from this construct and ligated into the yeast expression vector pRCD259, giving the construct pSH229. The expression construct contains the hygromycin selection marker; GAPDH promoter and CYC1 terminator, with the cloning sites NotI, AscI and PacI located between these two regions; URA3 targeting integration region; and a fragment of the pUC19 plasmid to facilitate bacterial replication.

EXAMPLE 5

Expression Vectors and Integration

To express the rat endomannosidase proteins in yeast, the cDNA encoding the catalytic domain was cloned into the expression vector pRCD259 producing the vector pSH229 (See Example 4). Subsequently, cDNAs encoding Gls1(s), Van1(s) and Mnn11(m) leaders were cloned 5' to the cDNA encoding the rat endomannosidase catalytic domain producing the plasmids pSH278 (rEndo Δ48 Gls1s leader), pSH279 (rEndo Δ48 Van1s leader) and pSH280 (rEndo Δ48 Mnn11m leader). Integration was confirmed by colony PCR with the resultant positive clones being analyzed to determine the N-glycan structure of a secreted reporter protein.

EXAMPLE 6

Northern Blot Analysis

Figure 8:
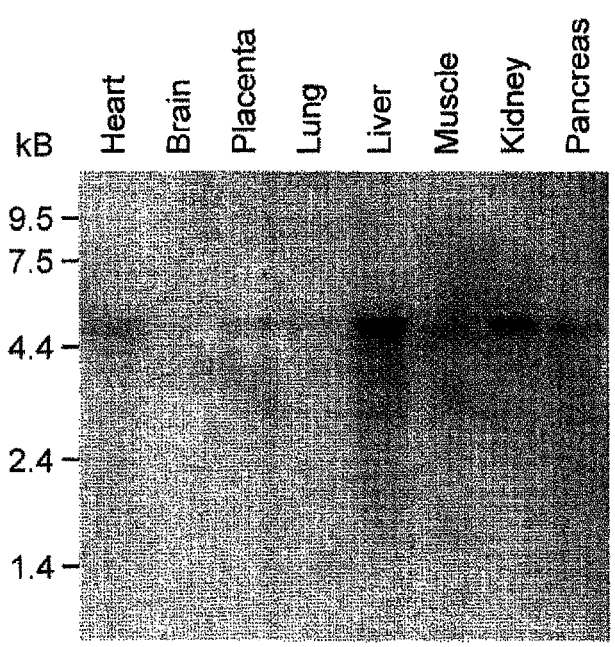
FIG. 8 depicts a Northern blot analysis of RNAs from a variety of human tissues hybridized with a labeled human endomannosidase nucleic acid probe.

Tissue distribution of human endomannosidase transcript was determined with a human Multiple Tissue Northern blot (Clontech) representing 2 μg of purified poly A$^+$ RNA from each of the tissues according to the instructions of the manufacturer. The 547 bp human endomannosidase DNA probe (843-1389) used was generated using the RadPrime DNA Labeling System (Invitrogen, Carlsbad, Calif.) and [$^{32}$P] dCTP. The results are shown in FIG. 8.

EXAMPLE 7

SDS-PAGE and Western Blotting

Media from the *P. pastoris* cultures were analyzed for endomannosidase secretion by running samples on a 10% SDS-PAGE (Laemmli, U.K. (1970) Cleavage of structural proteins during the assembly of the head of bacteriophage T4. Nature, 227, 680-685) using the Bio-Rad Mini-Protean II apparatus. The proteins were then transferred onto a nitrocellulose membrane (Schleicher & Schuell, Keene, N.H.). Recombinant endomannosidase was detected using the anti-FLAG M2 monoclonal antibody in combination with a goat anti-mouse HRP-conjugated secondary antibody and visualized with the ECL Western detection system (Amersham Biosciences) according to the manufacturer's instructions. Media from GS115 (Invitrogen, Carlsbad, Calif.) was used as a control. The results are shown in FIG. 9.

EXAMPLE 8

In Vitro Characterization of Recombinant Endomannosidase

GlcMan$_5$GlcNAc$_2$, a substrate for endomannosidase assays, was isolated from the och1 alg3 mutant strains RDP25 (WO 03/056914A1) (Davidson et al, 2003 in preparation). 2-aminobenzamide-labeled GlcMan$_5$GlcNAc$_2$ was added to 10 μl of culture supernatant and incubated at 37° C. for 8 h or overnight. 10 μl of water was then added and subsequently the glycans were separated by size and charge using an Econosil NH$_2$ 4.6×250 mm, 5 micron bead, amino-bound silica column (Altech, Avondale, Pa.) following the protocol of Choi et al, *Proc. Natl. Acad Sci. U.S.A.* 100(9):5022-5027 (2003).

EXAMPLE 9 pH and Temperature Optima Assays of Engineered Endo α-1,2-mannosidase

Fluorescence-labeled GlcMan$_5$GlcNAc$_2$ (0.5 μg) was added to 20 μL of supernatant adjusted to various pH (Table 2) and incubated for 8 hours at room temperature. Following incubation the sample was analyzed by HPLC using an Econosil NH2 4.6×250 mm, 5 micron bead, amino-bound silica column (Altech, Avondale, Pa.). The flow rate was 1.0 ml/min for 40 min and the column was maintained to 30° C. After eluting isocratically (68% A:32% B) for 3 min, a linear solvent gradient (68% A:32% B to 40% A:60% B) was employed over 27 min to elute the glycans (18). Solvent A (acetonitrile) and solvent B (ammonium formate, 50 mM, pH 4.5. The column was equilibrated with solvent (68% A:32% B) for 20 min between runs. The following table shows the amount (%) of Man$_4$GlcNAc$_2$ produced from GlcMan$_5$GlcNAc$_2$ at various pHs (FIG. 15, Table 2).

TABLE 2

| pH Optimum of Human Endomannosidase | |
|---|---|
| pH | % of Man4 |
| 4 | 0 |
| 4.5 | 0 |
| 5 | 4.5 |
| 5.5 | 29.6 |
| 6 | 51.4 |
| 6.5 | 52 |
| 7 | 41.3 |
| 7.5 | 30 |
| 8.5 | 20 |

The temperature optimum for human endomannosidase was similarly examined by incubating the enzyme substrate with culture supernatant at different temperatures (room temperature, 30° C. and 37° C.), 37° C. being the optimum.

EXAMPLE 10

Reporter Protein Expression, Purification and Release of N-Linked Glycans

Protein Purification

Kringle 3 (K3) domain, under the control of the alcohol oxidase 1 (AOX1) promoter, was used as a model protein. Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag (Choi et al. 2003, supra). The robotic purification is an adaptation of the protocol provided by Novagen for their HisBind resin. Briefly, a 150 uL (μL) settled volume of resin is poured into the wells of a 96-well lysate-binding plate, washed with 3 volumes of water and charged with 5 volumes of 50 mM NiSO4 and washed with 3 volumes of binding buffer (5 mM imidazole, 0.5M NaCl, 20 mM Tris-HCL pH 7.9). The protein expression media is diluted 3:2, media/PBS (60 mM PO4, 16 mM KCl, 822 mM NaCl pH 7.4) and loaded onto the columns. After draining, the columns are washed with 10 volumes of binding buffer and 6 volumes of wash buffer (30 mM imidazole, 0.5M NaCl, 20 mM Tris-HCl pH 7.9) and the protein is eluted with 6 volumes of elution buffer (1M imidazole, 0.5M NaCl, 20 mM Tris-HCl pH 7.9). The eluted glycoproteins are evaporated to dryness by lyophilyzation.

Release of N-Linked Glycans

The glycans are released and separated from the glycoproteins by a modification of a previously reported method (Papac et al., *Glycobiology* 8(5):445-54 (1998)). The wells of a 96-well MultiScreen IP (Immobilon-P membrane) plate (Millipore) were wetted with 100 uL of methanol, washed with 3×150 uL of water and 50 uL of RCM buffer (8M urea, 360 mM Tris, 3.2 mM EDTA pH 8.6), drained with gentle vacuum after each addition. The dried protein samples were dissolved in 30 uL of RCM buffer and transferred to the wells containing 10 uL of RCM buffer. The wells were drained and washed twice with RCM buffer. The proteins were reduced by addition of 60 uL of 0.1M DTT in RCM buffer for 1 hr at 37° C. The wells were washed three times with 300 uL of water and carboxymethylated by addition of 6 uL of 0.1M iodoacetic acid for 30 min in the dark at room temperature. The wells were again washed three times with water and the membranes blocked by the addition of 100 uL of 1% PVP 360 in water for 1 hr at room temperature. The wells were drained and washed three times with 300 uL of water and deglycosylated by the addition of 30 uL of 10 mM $NH_4HCO_3$ pH 8.3 containing one milliunit of N-glycanase (Glyko). After incubting for 16 hours at 37° C., the solution containing the glycans was removed by centrifugation and evaporated to dryness.

Miscellaneous:

Proteins were separated by SDS/PAGE according to Laemmli (Laemmli 1970).

EXAMPLE 11

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than $5\times10^{-7}$ torr, and the low mass gate was 875 Da. Spectra were generated from the sum of 100-200 laser pulses and acquired with a 2 GHz digitizer. $Man_5GlcNAc_2$ oligosaccharide was used as an external molecular weight standard. All spectra were generated with the instrument in the positive ion mode. The estimated mass accuracy of the spectra was 0.5%.

EXAMPLE 12

A Combinatorial Library to Produce a Chimeric Endomannosidase Protein

A library of human, mouse, rat and/or any combination of mixed endomannosidases characterized by catalytic domains having a range of temperature and pH optima is generated following published procedures (see, e.g., WO 02/00879; Choi et al. 2003, supra and the publication of U.S. application Ser. No. 10/371,877 (filed Feb. 20, 2003)). This library will be useful for selecting one or more sequences which encode a protein having endomannosidase activity that performs optimally in modifying the glycosylation pattern of a reporter protein to produce a desired glycan structure when expressed in a lower eukaryotic host cell such as a yeast. It is expected to be advantageous to target the catalytic domain of the endomannosidase to a specific cellular compartment. The DNA combinatorial library approach (in-frame fusion between a targeting peptide and an enzymatic domain) enables one to identify a chimeric molecule which expresses an endomannosidase activity in a desired or an efficient way in the host cell used for the seletion. An endomannosidase sequence is expressed in a number of expression systems— including bacterial, yeast and mammalian cells, to characterize the encoded protein.

To generate a human-like glycoform in a host, e.g., a microorganism, the host is engineered to express an endomannosidase enzyme (such as the human or mouse endomannosidase described herein) which hydrolyzes mono-, di- and tri-glucosylated high mannose glycoforms, removing the glucose residue(s) present and the juxta-positioned mannose (see FIG. 1). A DNA library comprising sequences encoding cis and medial Golgi localization signals (and optionally comprising ER localization signals) is fused in-frame to a library encoding one or more endomannosidase catalytic domains. The host organism is a strain, e.g. a yeast, that is deficient in hypermannosylation (e.g. an och1 mutant) and preferably, provides N-glycans having the structure $GlcNAcMan_5GlcNAc_2$ in the Golgi and/or ER. (Endomannosidase can hydrolyze $Glc_{1-3}Man_{9-5}GlcNAc_2$ to $Man_{8-4}GlcNAc_2$, so the preferred $GlcNAcMan_5GlcNAc_2$ structure is not essential). After transformation, organisms having the desired glycosylation phenotype are selected. Preferably, the endomannosidase activity removes a composition comprising at least a glucose residue and one mannose residue on an oligosaccharide. An in vitro assay is used in one method. The desired structure is a substrate for the enzyme alpha 1,2-mannosidase (see FIG. 2). Accordingly, single colonies may be assayed using this enzyme in vitro The foregoing in vitro assays are conveniently performed on individual colonies using high-throughput screening equipment. Alternatively, a lectin binding assay is used. In this case the reduced binding of lectins specific for terminal mannoses allows the selection of transformants having the desired phenotype. For example, *Galantus nivalis* lectin binds specifically to terminal α-1,3-mannose, the concentration of which is reduced in the presence of operatively expressed endomannosidase activity. In one suitable method, *G. nivalis* lectin attached to a solid agarose support (available from Sigma Chemical, St. Louis, Mo.) is used to deplete the transformed population of cells having high levels of terminal α-1,3-mannose.

What is claimed is:

1. An isolated polynucleotide encoding a fusion protein comprising an endomannosidase catalytic domain and a cellular targeting signal peptide, wherein the endomannosidase catalytic domain is encoded by a nucleic acid selected from the group consisting of:
   (a) a nucleic acid encoding a catalytically active domain of SEQ ID NO:2, and
   (b) a nucleic acid encoding a catalytically active domain of SEQ ID NO:4.

2. A vector comprising the polynucleotide of claim 1.

3. A host cell comprising the polynucleotide of claim 1.

4. The host cell of claim 3 wherein the host cell is a mammalian, plant, insect, fungal, yeast, algal or bacterial cell.

5. The host cell of claim 3, wherein the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum* and *Neurospora crassa.*

* * * * *